US007214663B2

(12) United States Patent
Bebbington et al.

(10) Patent No.: US 7,214,663 B2
(45) Date of Patent: May 8, 2007

(54) TRIPEPTIDE PRODRUG COMPOUNDS

(75) Inventors: Christopher R. Bebbington, San Mateo, CA (US); Vincent Dubois, Fleurus (BE); Sanjeev Gangwar, Alameda, CA (US); Thomas J. Lobl, Valencia, CA (US); Matthew H. Nieder, Seattle, WA (US); Lesley B. Pickford, Menlo Park, CA (US); Andre Trouet, Herent (BE); Geoffrey T. Yarranton, Burlingame, CA (US)

(73) Assignee: Medarex, Inc., Princeton, NJ (US)

( * ) Notice: Subject to any disclaimer, the term of this patent is extended or adjusted under 35 U.S.C. 154(b) by 450 days.

(21) Appl. No.: 10/311,519

(22) PCT Filed: Jun. 11, 2001

(86) PCT No.: PCT/US01/40925

§ 371 (c)(1),
(2), (4) Date: Dec. 13, 2002

(87) PCT Pub. No.: WO02/00263

PCT Pub. Date: Jan. 3, 2002

(65) Prior Publication Data

US 2003/0181359 A1 Sep. 25, 2003

(51) Int. Cl.
C07K 5/083 (2006.01)
A61K 38/06 (2006.01)
(52) U.S. Cl. .......................... 514/18; 530/331
(58) Field of Classification Search ............... None
See application file for complete search history.

(56) References Cited

U.S. PATENT DOCUMENTS

| 5,962,216 A | 10/1999 | Trouet et al. |
| 6,342,480 B1 | 1/2002 | Trouet et al. |
| 2002/0142955 A1* | 10/2002 | Dubois et al. ............ 514/12 |

FOREIGN PATENT DOCUMENTS

| WO | WO 92/07068 | 4/1992 |
| WO | WO 96/05863 A1 | 2/1996 |
| WO | WO 00/33888 A1 | 6/2000 |

OTHER PUBLICATIONS

Marre De A et al., "Evaluation of the Hydrolytic and Enzymatic Stability of Macromolecular Mitomycin C Derivatives." J. Controlled Release, 31(1):89-97 (1994).
Masquelier et al., "Antitumor activity of daunorubicin linked to proteins: biological and antitumor properties of peptidic derivatives of daunorubicin used as intermediates," (Abstract) Database: CHEMABS Acc. No. 97:150635 HCA, Chemical Abstract Service, Columbus. Ohio (1981).

Masquelier M et al., "Amino Acid and Dipeptide Derivatives of Daunorubicin. 1. Synthesis, Physicochemical Properties, and Lysosomal Digestion." J. Medicinal Chem.. 23(11):1166-1170 (1980).
Subr V "Polymers Containing Enzymatically Degradable Bonds XII Effect of Spacer Structure on the Rate of Release of Daunomycin and Adriamycin from Poly(N-(2-Hydroxypropyl)-Methacrylamide) Copolymer Drug Carriers Invitro and Antitumour Activity Measured in Vivo." J. Controlled Release, 18(2):123-132 (1992).
Barrett AJ, and Brown MA, "Chicken liver Pz-peptidase, a thiol-dependent metallo-endopeptidase." Biochem J. Nov. 1;271(3):701-6 (1990).
Bricout H, et al., "Synthetic and Kinetic Aspects of Nickel-Catalysed Amination of Allylic Alcohol Derivatives," Tet. Lett., 54:1073 (1998).
Casimir JR, et al., "First Application of the Dakin-West Reaction to Fmoc Chemistry: Synthesis of the ketomethylene tripeptide Fmox-Nα-Asp(tBu)-(R,S)Tyr(tBu) Ψ(CO-CH$_2$)Gly-OH," Tet. Lett. 36(27):4797-4800 (1995).
Chaires JB, et al., "Self-association of daunomycin." Biochemistry. Aug. 17;21(17):3927-32 (1982).
Crack PJ, et al., "The association of metalloendopeptidase EC 3.4.24.15 at the extracellular surface of the AtT-20 cell plasma membrane." Brain Res. Jul. 24;835(2):113-24 (1999).
Dando PM, et al., "Human thimet oligopeptidase." Biochem J. Sep. 1;294 (Pt 2);451-7 (1993).
Ferro ES, et al., "Secretion of metalloendopeptidase 24.15 (EC 3.4.24.15)." DNA Cell Biol. Oct.;18(10):781-9 (1999).
Garrido PA, et al., "Confocal microscopy reveals thimet oligopeptidase (EC 3.4.24.15) and neurolysin (EC 3.4.24.16) in the classical secretory pathway." DNA Cell Biol. Apr.;18(4):323-31 (1999).
Genet J-P, et al., "Practical Palladium-Mediated Deprotective Method of Allyloxycarbonyl in Aqueous Media," *Tetrahedron*, 50(2):497-503 (1994).
Genet J-P, et al., "A General and Simple Removal of the Allyloxycarbonyl Protecting Group by Palladium-Catalyzed Reactions Using Nitrogen and Sulfur Necleophiles," Synlett, 680-682 (1993).
Hayakawa E, et al., "Viscosity Study on the Self-Association of Doxorubicin in Aqueous Solution," Chem. Pharm. Bull., 39:1282-6(1991).

(Continued)

*Primary Examiner*—Anish Gupta
(74) *Attorney, Agent, or Firm*—Lahive & Cockfield, LLP; Jane E. Remillard, Esq.; Cynthia M. Soroos, Esq.

(57) ABSTRACT

The prodrug of the invention is a modified form of a therapeutic agent and comprises a therapeutic agent, an oligopeptide of three amino acids, a stabilizing group and, optionally, a linker group. The prodrug is cleavable by a trouase enzyme such as Thimet oligopeptidase. Also disclosed are methods of making and using the prodrug compounds.

26 Claims, 20 Drawing Sheets

OTHER PUBLICATIONS

Kato A, "Cloning, amino acid sequence and tissue distribution of porcine thimetoligopeptidase. A comparison with soluble angiotensin-binding protein." Eur J Biochem. Apr. 1;221(1);159-65. (1994).

Krause DR, et al., "Characterization and localization of mitochondrial oligopeptidase (MOP) (EC3.4-.24.16) activity in the human cervical adenocarinoma cell line HeLa." J Cell Biochem. Sep. 1;66(3):297-308 (1997).

Lew RA, et al., "Substrate specificity differences between recombinant rat testes endopeptidase EC 3.4.24.15 and the native brain enzyme." Biochem Biophys Res Commun. Apr. 26;209(3):788-95 (1995).

Matzanke BF, et al., "Evidence for polynuclear aggregates of ferric daunomycin," Eur. J. Biochem., 207:747-55 (1992).

Moody TW, et al., "Neurotensin is metabolized by endogenous proteases in prostate cancer cell lines." Peptides. 19(2):253-8. (1998).

Morales, et al., "PZ-peptidase from chick embryos. Purification, properties and action on collagen peptides." J. Biol. Chem. Jul. 25;252(14):4855-4860 (1977).

Oliveira V, et al., "Characterization of thiol-, aspartyl-, and thiol-metallo-peptidase activities in Madin-Darby canine kidney cells." J Cell Biochem. Jan.;76(3):478-88. (2000).

Orlowski. et al., "Endopeptidse 24.15 from rat testes. Isolation of the enzyme and its specificity toward synthetic and natural peptides, including enkephalin-containing peptides." Biochem. J. Aug. 1,261(3).951-958 (1989).

Pierotti AR, et al., "Endopeptidase-24.15 in rat hypothalamic/pituitary/gonadal axis." Mol Cell Endocrinol Apr.;76(1-3):95-103 (1991).

Pozsgay M et al., "Substrate and inhibitor studies of thermolysin-like neutral metalloendopeptidase from kidney membrane fraction. Comparison with bacterial thermolysin." Biochemistry Mar. 25;25(6):1292-9 (1986).

Schmittberger, T. and Waldmann, H., et al., "Synthesis of the Palmitoylated and Prenylated C-terminal Lipopeptides of the Human R- and N-*Ras* Proteins." Bioorg. Med. Chem., 7:749-752 (1999).

Shapiro G. and Buechler D., "Mild and Rapid Azide-Mediated, Palladium Catalyzed Cleavage of Allylester Based Protecting Groups," Tet. Lett., 35(30):5421-5424 (1994).

Shrimpton CN, et al., "Thiol activation of endopeptidase EC 3.4.24.15. A novel mechanism for the regulation of catalytic activity." J Biol Chem. Jul. 11;272(28):17395-9 (1997).

Tabrizi-Fard, et al., "Evaluation of the Pharmacokinetic Properties of a Doxorubicin Prodrug in Female ICR (CDI®) Mice following intravenous adminstration." Proc. American Association for Cancer Research, 42:324 (2001).

Turner AJ, "Neprilysin," in *Handbook of proteolytic enzymes*, Barret AJ et al. eds, pp. 1080-1085, Academic Press, San. Diego (1998).

* cited by examiner

| Symbol | Name | Structure |
|---|---|---|
| Aib | Aminoisobutyric Acid | $H_2N-C(CH_3)_2-COOH$ |
| Amb | 4-(Aminomethyl)benzoic Acid | $H_2N-CH_2-C_6H_4-COOH$ |
| APP | 3-Amino-3-phenylpropionic Acid | 3-amino-3-phenylpropionic acid structure |
| Dg | Diglycolic Acid | $HOOC-CH_2-O-CH_2-COOH$ |
| Gl | Glutaric Acid | $HOOC-(CH_2)_3-COOH$ |

FIG. 1A

| Symbol | Name | Structure |
|---|---|---|
| Mal | Maleic Acid | 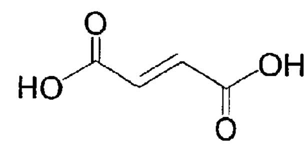 |
| NAA | 3-Amino-4,4-diphenylbutyric Acid | 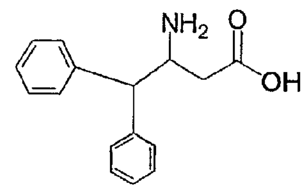 |
| Nal | 2-Naphthylalanine | 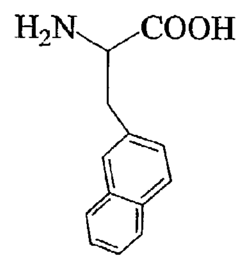 |
| Naph | 1,8-Naphthalene dicarboxylic Acid | 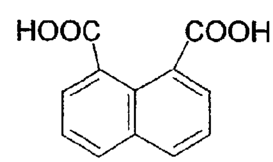 |
| Phg | Phenylglycine | 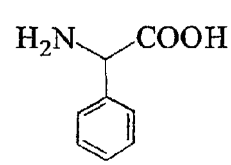 |

| Symbol | Name | Structure |
|---|---|---|
| PEG | Polyethylene Glycol$_{5000}$ Hemisuccinyl Ester |  n=4-110 |
| Pyg | Pyroglutamic Acid | 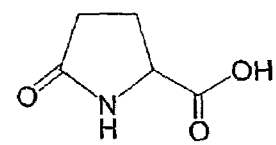 |
| Pyr | 3-Pyridylalanine | 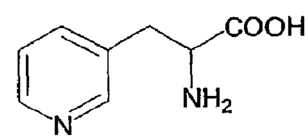 |
| Suc | Succinic Acid | 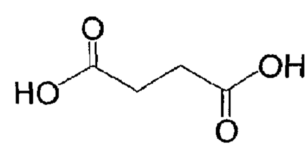 |
| Thi | 2-Thienylalanine | 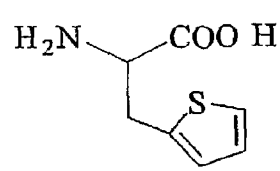 |

| Symbol | Name | Structure |
|---|---|---|
| Thz | 3-Thioproline or Thiazolidine-4-carboxylic Acid | 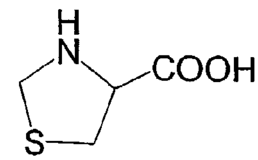 |
| Tic | Tetrahydroisoquinoline-3-carboxylic Acid | 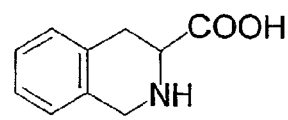 |

TRIPEPTIDE PRODRUG COMPOUNDS

INTRODUCTION

1. Technical Field

The present invention is directed to new compounds useful as prodrugs, and methods for making them. Such prodrugs may be used for treatment of disease, especially tumors, in patients.

2. Background

Many therapeutic agents, such as anthracyclines and vinca alkaloids, are especially effective for the treatment of cancers. However, these molecules are often characterized in vivo by an acute toxicity, especially a bone marrow and mucosal toxicity, as well as a chronic cardiac toxicity in the case of the anthracyclines and chronic neurological toxicity in the case of the vinca alkaloids. Similarly, methotrexate may be used for the treatment of inflammatory reactions, such as rheumatic diseases, but its high toxicity limits its applications. Development of more and safer specific antitumor agents is desirable for greater effectiveness against tumor cells and a decrease in the number and severity of the side effects of these products (toxicity, destruction of non-tumor cells, etc.). Development of more specific anti-inflammatory agents is also desirable.

In order to minimize toxicity problems, therapeutic agents are advantageously presented to patients in the form of prodrugs. Prodrugs are molecules capable of being converted to drugs (active therapeutic compounds) in vivo by certain chemical or enzymatic modifications of their structure. For purposes of reducing toxicity, this conversion should be confined to the site of action or target tissue rather than the circulatory system or non-target tissue. Prodrugs are often characterized by a low stability in blood and serum, however. This is due to the presence of enzymes in blood and serum that degrade, and consequently may activate, the prodrugs before the prodrugs can reach the desired sites within the patient's body.

A desirable class of prodrugs that overcomes such problems has been disclosed in Patent Cooperation Treaty International Publication No. WO 96/05863 and in U.S. Pat. No. 5,962,216, both incorporated herein by reference. Further useful prodrug compounds and methods of making such prodrugs are desirable, however, as are methods of making the prodrugs.

Prodrugs that display a high specificity of action, a reduced toxicity, and an improved stability in blood especially relative to prodrugs of similar structure (especially the closest structure) that have existed in the public domain are particularly desirable.

SUMMARY OF THE INVENTION

The compound of the invention is a prodrug form of a therapeutic agent, in which the therapeutic agent is linked directly or indirectly to an oligopeptide of three amino acids, which in turn, is linked to a stabilizing group. The prodrugs of the invention display a high specificity of action, a reduced toxicity, an improved stability in serum and blood, and move into target cells minimally unless activated by a target cell associated enzyme. Additionally, the compounds are preferably cleaved by a trouase, such as TOP, at a rate of cleavage that is a fractional portion of the rate of cleavage of Suc-βAla-Leu-Ala-Leu-Dox.

The present invention also relates to a pharmaceutical composition comprising the compound according to the invention and optionally a pharmaceutically acceptable carrier, adjuvant, vehicle or the like. Articles of manufacture comprising the prodrugs of the invention are also described. Thus, the invention includes a diagnosis or assay kit employing a compound of the invention.

Further methods of designing a prodrug and of decreasing toxicity and improving safety index by modifying a therapeutic agent to create a prodrug are disclosed. Such modification provides an improved therapeutic index of the prodrug as compared to the free therapeutic agent. Several methods of making prodrugs of the invention are also described.

The present invention further includes methods of treating a medical condition by administering the prodrug of the invention to a patient in a therapeutically effective amount.

BRIEF DESCRIPTION OF THE DRAWINGS

FIGS. 1A–1D are a table of abbreviations, names, and structures.

DETAILED DESCRIPTION

Figure 1B:
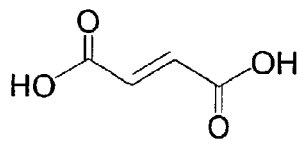
Figure 1B:
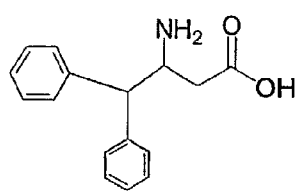
Figure 1B:
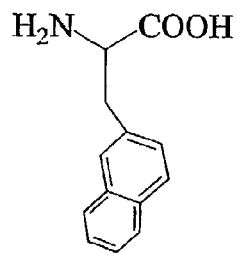
Figure 1B:
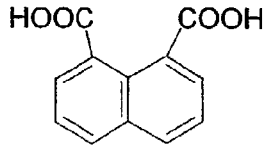
Figure 1B:
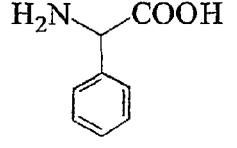
Figure 1C:
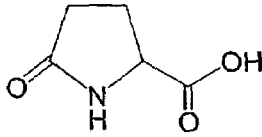
Figure 1C:
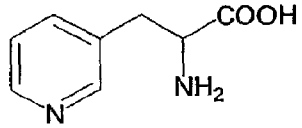
Figure 1C:
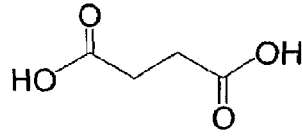
Figure 1C:
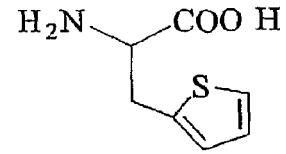
Figure 1D:
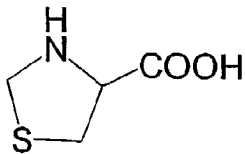
Figure 1D:
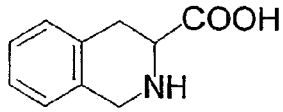

Abbreviations
ACN=Acetonitrile
Aib=Aminoisobutyric acid
All=Allyl
Aloc=Allyloxycarbonyl
Amb=4-(Aminomethyl)benzoic acid
APP=3-Amino-3-phenylpropionic acid
DCC=N,N'-Dicyclohexylcarbodiimide
Boc=t-butyloxycarbonyl
Cap=amino caproic acid
DBN=1,5 Diazabicyclo[4.3.0]non-5-ene
DBO=1,4 Diazabicyclo[2.2.2]octane
DBU=1,8-Diazabicyclo[5.4.0]undec-7-ene
DCM=Dichloromethane
DIC=N,N'-Diisopropylcarbodiimide
DIEA=Diisopropylethylamine
Dg=Diglycolic Acid
DMF=Dimethylformamide
Dnr=Daunorubicin
Dox=Doxorubicin
$Et_2O$=diethyl ether
Fmoc=9-Fluorenylmethyloxycarbonyl
Gl=Glutaric Acid
HATU=O-(7-Azabenzotriazol-1-yl)-1,1,3,3-tetramethyluronium-hexafluorophosphate
HBTU=2-(1H-Benzotriazole-1-yl)1,1,3,3-tetramethyluronium-hexafluorophosphate
HEPES=Hydroxethylpiperidine
HOBt=N-Hydroxybenzotriazole
HPLC=High pressure liquid chromatography
MeOH=Methanol
MeOSuc=Methyl hemisuccinate or methyl hemisuccinyl
MTD=Maximum tolerated dose
NAA=3-Amino-4,4-diphenylbutyric Acid
Nal=2-Naphthylalanine
Naph=1,8-Naphthalene dicarboxylic acid
Nle=Norleucine
NMP=N-methylpyrrolidine
Nva=Norvaline
PAM resin=4-hydroxymethylphenylacetamidomethyl
PEG=Polyethylene glycol
Pyg=Pyroglutamic acid
Pyr=3-Pyridylalanine
RD=repeat dose
RD-MTD=repeat dose maximum tolerated dose
RT, rt=Room temperature
SD=single dose
SD-MTD=single dose maximum tolerated dose
Suc=Succinyl Acid/Succinyl
TCE=trichloroethyl
TFA=trifluoroacetic acid
THF=Tetrahydrofuran
Thi=2-Thienylalanine
Thz=Thiazolidine-4-carboxylic acid
Tic=Tetrahydroisoquinoline-3-carboxylic acid
TOP=Thimet oligopeptidase Compounds of the invention are prodrug forms of therapeutic agents. The therapeutic agent is linked directly or indirectly to an oligopeptide of three amino acids, which in turn, is linked to a stabilizing group. The prodrugs of the invention display a high specificity of action, a reduced toxicity, an improved stability in serum and blood, and move into target cells minimally unless activated by a target cell associated enzyme. The enzyme associated with the target cell is preferably a trouase, and more preferably is Thimet oligopeptidase or "TOP."

Prodrug

The prodrug of the invention is a modified form of a therapeutic agent and comprises several portions, including:
 (1) a therapeutic agent,
 (2) an oligopeptide, and
 (3) a stabilizing group, and
 (4) optionally, a linker group.

Each of the portions of the prodrug are discussed in greater detail below. The typical orientation of these portions of the prodrug is as follows:

(stabilizing group)-(oligopeptide)-(optional linker group)-(therapeutic agent).

The stabilizing group is directly linked to the oligopeptide at a first attachment site of the oligopeptide. The oligopeptide is directly or indirectly linked to the therapeutic agent at a second attachment site of the oligopeptide. If the oligopeptide and the therapeutic agent are indirectly linked, then a linker group is present.

Direct linkage of two portions of the prodrug means a covalent bond exists between the two portions. The stabilizing group and the oligopeptide are therefore directly linked via a covalent chemical bond at the first attachment site of the oligopeptide, typically the N-terminus of the oligopeptide. When the oligopeptide and the therapeutic agent are directly linked then they are covalently bound to one another at the second attachment site of the oligopeptide. The second attachment site of the oligopeptide is typically the C-terminus of the oligopeptide, but may be elsewhere on the oligopeptide.

Indirect linkage of two portions of the prodrug means each of the two portions is covalently bound to a linker group. In an alternative embodiment, the prodrug has indirect linkage of the oligopeptide to the therapeutic agent. Thus, typically, the oligopeptide is covalently bound to the linker group which, in turn, is covalently bound to the therapeutic agent.

The prodrug of the invention is cleavable within its oligopeptide portion. In order for the prodrug to be effective, the prodrug typically undergoes in vivo modification and an active portion, i.e., a transport-competent portion, of the prodrug enters the target cell. A first cleavage within the oligopeptide portion of the prodrug may leave an active or transport-competent portion of the prodrug as one of the cleavage products. Alternatively, further cleavage by one or more peptidases may be required to result in a portion of the prodrug that is capable of entering the cell. The active portion of the prodrug has at least the therapeutic agent and is that part of the prodrug that can enter the target cell to exert a therapeutic effect directly or upon further conversion within the target cell. Thus, the compound has an active portion, and the active portion is more capable of entering the target cell after cleavage by an enzyme associated with the target cell than prior to cleavage by an enzyme associated with a target cell.

The structures of the stabilizing group and oligopeptide are selected to limit clearance and metabolism of the prodrug by enzymes that may be present in blood or non-target tissue and are further selected to limit transport of the prodrug into the cells. The stabilizing group blocks degradation of the prodrug and may act in providing preferable charge or other physical characteristics of the prodrug. The amino acid sequence of the oligopeptide is designed to ensure specific cleavage by an enzyme associated with a target cell, more specifically by a trouase enzyme, and even more specifically by TOP.

It is desirable to make a therapeutic agent, especially an antitumor and/or anti-inflammatory therapeutic agent, inactive by modification of the therapeutic agent to a prodrug form. According to the invention, the target cells are usually tumor cells or cells participating in inflammatory reactions, especially those associated with rheumatic diseases, such as macrophages, neutrophils, and monocytes. Modification of the therapeutic agent to a prodrug form also reduces some of the side effects of the therapeutic agents.

In the target cell, the therapeutic agent (optionally attached to one or two amino acids and possibly also a linker group) acts either directly on its specific intracellular action site or, after a modification by intracellular proteases, kills the target cell or blocks its proliferation. Since normal cells release little to no trouase in vivo, the compound according to the invention is maintained inactive and does not enter the normal cells or does so to a relatively minor extent. Although TOP is believed to be widely distributed in the body, it is typically present as an intracellular enzyme. Therefore it is generally inaccessible to peptide prodrugs in the circulation. In the environment of the tumor, TOP is believed to be released from necrotic tissue.

Figure 2:
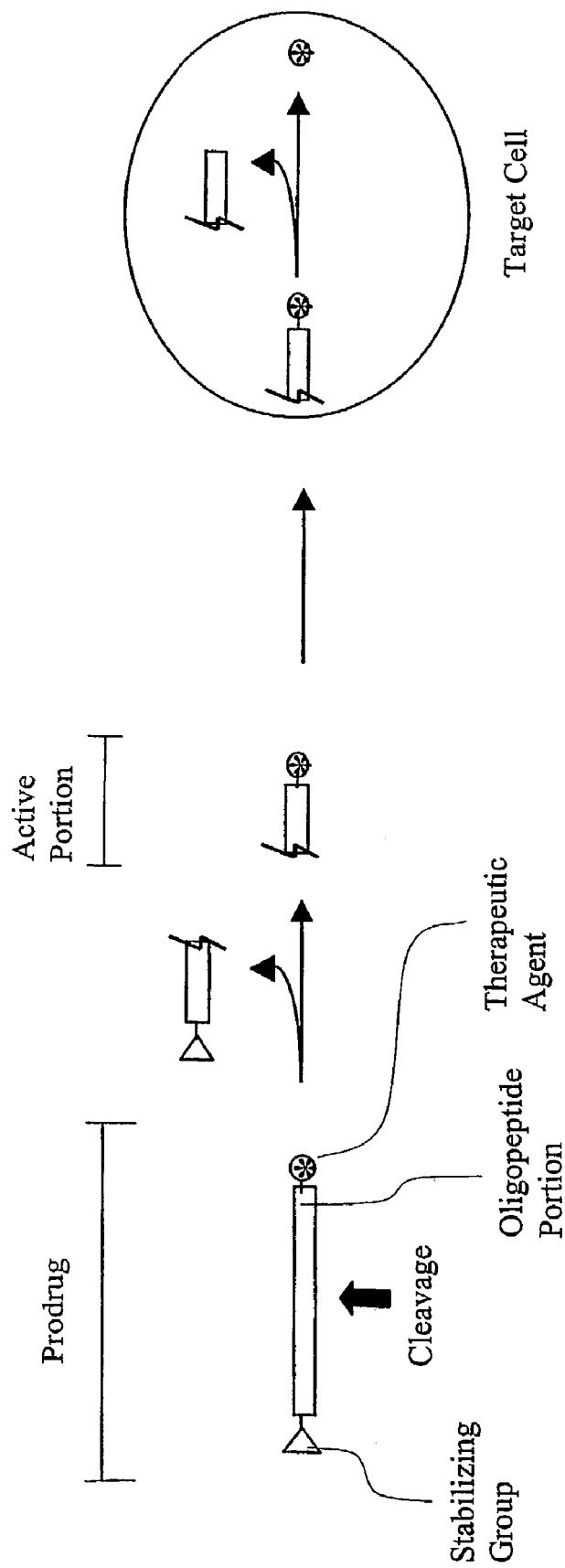
FIG. 2 is an exemplary scheme of cleavage of a prodrug of the invention in the extracellular vicinity of the target cell and within the target cell.

The prodrug is administered to the patient, carried through the blood stream in a stable form, and when in the vicinity of a target cell, is acted upon by a trouase, such as TOP. Since the enzyme activity is only minimally present within the extracellular vicinity of normal cells, the prodrug is maintained and its active portion (including the therapeutic agent) gains entry into the normal cells only minimally. In the vicinity of tumor or other target cells, however, the presence of the relevant enzyme in the local environment causes cleavage of the prodrug. The example shown in FIG. 2 depicts an N-capped prodrug being cleaved extracellularly and the transport-competent or active portion gaining entry into the target cell. Once within the target cell, it may be further modified to provide therapeutic effect, such as by killing the target cell or blocking its proliferation. While a portion of the prodrug may occasionally gain access to, and possibly harm normal cells, the transport-competent portion of the drug is freed primarily in the vicinity of target cells. Thus, toxicity to normal cells is minimized.

This process is particularly useful for, and is designed for, target cell destruction when the target tissue releases an enzyme that is not released by normal cells or tissue. Here "normal cells" means non-target cells that would be encountered by the prodrug upon administration of the prodrug in the manner appropriate for its intended use.

In an alternative embodiment, the orientation of the prodrug may be reversed so that the stabilizing group is attached to the C-terminus of the oligopeptide and the therapeutic agent is directly or indirectly linked to the N-terminus of the oligopeptide. Thus, in the alternative embodiment, the first attachment site may be the C-terminus of the oligopeptide and the second attachment site of the oligopeptide may be the N-terminus of the oligopeptide. The alternative embodiment of the invention functions in the same manner as does the primary embodiment.

In Patent Cooperation Treaty International Publication No. WO 96/05863 and in U.S. Pat. No. 5,962,216, certain useful prodrugs were disclosed. The present invention is distinct from the prodrugs disclosed therein. Thus, if the oligopeptide is Leu-Ala-Leu, then the stabilizing group is not succinyl or the therapeutic agent is not daunorubicin.

As described in greater detail below, the prodrugs of the invention are compounds comprising:
(1) a therapeutic agent capable of entering a target cell,
(2) an oligopeptide having the formula $AA^3$-$AA^2$-$AA^1$ wherein each AA independently represents an amino acid,
(3) a stabilizing group, and
(4) optionally, a linker group not cleavable by TOP,
wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
wherein the stabilizing group hinders cleavage of the oligopeptide by enzymes present in whole blood, and
wherein the compound is cleaved by TOP.

Prodrugs of the invention that are cleaved by TOP under an experimental condition at a test rate of cleavage of 10–80% of a standard rate of cleavage are especially useful. The standard rate of cleavage is tested on a test standard by TOP under the experimental condition, the test standard consisting of a conjugate of Suc-βAla-Leu-Ala-Leu and the therapeutic agent. As used herein, "cleavable by" means cleavable under physiological conditions.

For purposes of this discussion, a compound is resistant to cleavage by a given enzyme if the rate of cleavage by a purified preparation of the given enzyme is no more than 15%, preferably no more than 5%, and ideally no more than 1% of the rate of cleavage of Suc-βAla-Leu-Ala-Leu conjugated via the carboxyl terminus to the same therapeutic agent as the compound of interest. The rates should be compared under the same assay conditions. A compound is cleavable by a given enzyme if greater than 10% per hour, preferably greater than 50% per hour, is cleaved by a mixture of the compound and the enzyme under experimental conditions which model physiological conditions, particularly those outside of the target cell. The concentration of the given enzyme in the experiment is representative of the concentration of the given enzyme in the extracellular milieu of the target tissue.

Target Cell Associated Enzymes

The prodrugs of the invention are designed to take advantage of preferential activation through interaction with an enzyme associated with the target cell, at or near the site targeted within the body of the patient. Trouase, described in greater detail in PCT/US99/30393, incorporated herein by reference, is a class of target cell associated enzymes.

It is believed that a trouase activates the prodrug of the invention at the target tissue. Trouase is a class of endopeptidases that show a remarkable degree of discrimination between leucine and isoleucine at the carboxyl side of the oligopeptide cleavage site. A defining characteristic is that under appropriate assay conditions, a trouase readily cleaves Suc-βAla-Leu-Ala-Leu-Dnr while it is at least twenty-fold less active with Suc-βAla-Ile-Ala-Leu-Dnr.

Trouase is believed to be associated with target cells. Most likely trouase is generated either by target cells or by normal cells that are associated with the target cells, such as stromal tissue, neutrophils, macrophages, or B cells. So, for example, the trouase may be associated with or bound on (at least the active site) the outer cell surface, secreted, released or present in come manner in the extracellular vicinity of the target cell. In many cases, the prodrug of the invention includes a therapeutic agent for the treatment of cancer and the target cell is a tumor cell. Thus, the trouase may be released extracellularly by the tumor cell or it may be present extracellularly, e.g., because cell lysis is often associated with tumors. Cell lysis is also associated with inflammatory tissue, another target site.

Trouase activity is low in human plasma, however. Trouase activity has been observed in carcinoma cell extracts and conditioned media from cultured carcinoma cells, red blood cells and various human tissues, especially kidney. A partial purification scheme of trouase from HeLa (cervical carcinoma) cell homogenate ultracentrifugation (145,000×g for 30 min) supernatant consists of four steps as follows:

1. Anion exchange chromatography using a 15Q column (Pharmacia) eluted with a 0 to 0.5 M NaCl linear gradient in 20 mM triethylamine chloride pH 7.2, 0.01% Triton X-100,
2. Affinity chromatography using Chelating Sepharose Fast Flow (Pharmacia) pre-loaded with $CoCl_2$ and eluted with a 0 to 200 mM imidazole linear gradient in 10 mM sodium phosphate, 0.5 M NaCl, pH 7.2, 0.01% Triton X-100, 0.02% $NaN_3$,
3. Preparative native electrophoresis, and
4. Gel filtration high performance liquid chromatography using a 7.8 mm×60 cm TSK Gel G-3000SWXL (Toso-Haas) column eluted with 0.3 mL/min 50 mM potassium phosphate, 200 mM potassium sulfate, pH 7.0.

Further cleavage of the portion of the prodrug released after trouase cleavage may occur intracellularly or extracellularly, possibly by amino-exopeptidases. In vitro experiments indicate that amino-exopeptidases of broad specificities are present in human blood as well as the carcinoma cell environment.

Evidence now suggests that TOP is an example of a trouase. The trouase isolated from HeLa cell extracts and studied in conditioned media or homogenates from MCF-7/6 human carcinoma cells, catalyzes the initial cleavage of Suc-βAla-Leu-Ala-Leu-Dox. The trouase isolated from these sources is believed to be TOP. Both structural and functional evidence indicate that TOP is a trouase found in carcinoma cells.

According to the literature, TOP, or EC 3.4.24.15, is a thiol-activated zinc metallopeptidase which catalyzes internal (endo) cleavage of various oligopeptides having 6 to 17 amino acids (Dando, et al., "Human thimet oligopeptidase," *Biochem J* 294:451–457 (1993)). TOP is also is referred to as Pz-peptidase, collagenase-like peptidase, kininase A, amyloidin protease, and metalloendopeptidase 24.15. The enzyme has been isolated from chicken embryo (Morales, et al., "PZ-peptidase from chick embryos. Purification, properties, and action on collagen peptides," *J Biol Chem* 252: 4855–4860 (1977)), chicken liver (Barrett, et al., "Chicken liver Pz-peptidase, a thiol-dependent metallo-endopeptidase," *Biochem J* 271:701–706 (1990)), rat testis (Orlowski, et al., "Endopeptidase 24.15 from rat testes. Isolation of the enzyme and its specificity toward synthetic and natural peptides, including enkephalin-containing peptides," *Biochem J* 261: 951–958 (1989)), and human erythrocytes (Dando, et al., "Human thimet oligopeptidase," *Biochem J* 294:451–457 (1993)). The gene for this enzyme has been cloned and DNA sequence obtained from human brain (Dovey et al., WO 92/07068), rat testis (Pierotti, et al., "Endopeptidase-24.15 in rat hypothalamic/pituitary/gonadal axis," *Mol Cell Endocrinol* 76:95–103 (1991)) and pig liver (Kato, et al., "Cloning, amino acid sequence and tissue distribution of porcine thimet oligopeptidase. A comparison with soluble angiotensin-binding protein," *Eur J Biochem* 221:159–165 (1994)). TOP has been immunologically or functionally identified in extracts of HeLa (Krause, et al., "Characterization and localization of mitochondrial oligopeptidase (MOP) (EC 3.4.24.16) activity in the human cervical adenocarcinoma cell line HeLa," *J Cell Biochem* 66:297–308 (1997); AT-20 cells (Crack, et al., "The association of metalloendopeptidase EC 3.4.24.15 at the extracellular surface of the AtT-20 cell plasma membrane," *Brain Res* 835:113–124 (1999); Ferro, et al., "Secretion of metalloendopeptidase 24.15 (EC 3.4.24.15)," *DNA Cell Biol* 18:781–789 (1999); Garrido, et al., "Confocal microscopy reveals thimet oligopeptidase (EC 3.4.24.15) and neurolysin (EC 3.4.24.16) in the classical secretory pathway," *DNA Cell Biol* 18:323–331 (1999); Madin-Darby canine kidney cells (Oliveira, et al., "Characterization of thiol-, aspartyl-, and thiol-metallopeptidase activities in Madin-Darby canine kidney cells," *J Cell Biochem* 76:478–488 (2000); and prostate cancer cell lines (Moody, et al., "Neurotensin is metabolized by endogenous proteases in prostate cancer cell lines," *Peptides* 19:253–258 (1998)).

As with TOP (Barrett, et al., "Chicken liver Pz-peptidase, a thiol-dependent metallo-endopeptidase," *Biochem J* 271: 701–706 (1990); Lew, et al. "Substrate specificity differences between recombinant rat testes endopeptidase EC 3.4.24.15 and the native brain enzyme," *Biochem Biophys Res Commun* 209: 788–795 (1995)), carcinoma cell trouase is inhibited by the metallopeptidase inhibitors EDTA and 1,10-phenanthroline but not serine, thiol, or acid proteinase inhibitors such as aminoethylbenzene-sufonate, E64, pepstatin, leupeptin, aprotinin, CA074, or fumagillin. As reported for TOP, EDTA-treated carcinoma cell trouase is reactivated by $Co^{2+}$ (50–100 μM) or $Mn^{2+}$ (50–1000 μM). Although it is also possible to reactivate EDTA-deactivated chicken (Barrett, et al., "Chicken liver Pz-peptidase, a thiol-dependent metallo-endopeptidase," *Biochem J* 271: 701–706 (1990)) or rat (Orlowski, et al., "Endopeptidase 24.15 from rat testes. Isolation of the enzyme and its specificity toward synthetic and natural peptides, including enkephalin-containing peptides," *Biochem J* 261: 951–958 (1989)) TOP with $Zn^{2+}$, $Zn^{2+}$ reactivation is not seen with the EDTA-treated MCF-7/6 cell homogenate. The specific methods used for EDTA treatment and removal may affect the result with the carcinoma cell trouase. The fact that concentrations of $Zn^{2+}$ as low as 100 μM are inhibitory to TOP may also be a factor. $Zn^{2+}$ at 100 μM completely inhibits hydrolysis of Suc-βAla-Leu-Ala-Leu-Dox by HeLa cell Fraction 1. EDTA inactivated carcinoma cell trouase can not be reactivated with cupric ions.

TOP activity is likely to be inhibited in oxygenated solutions (such as blood) and activated in mildly reducing (anoxic) environments, as demonstrated by thiol activation of air inactivated preparations (Shrimpton et al., "Thiol activation of endopeptidase EC 3.4.24.15. A novel mechanism for the regulation of catalytic activity," *J Biol Chem.* 272:17395–17399 (1997)). Accordingly, it is good candidate to select prodrugs that are to be activated in anoxic environments such as tumor tissue. Thus it is an example of a general approach for selection of target cell associated prodrug activating enzymes.

CD10 (CALLA, neprilysin, neutral endopeptidase, EC 3.4.24.11) is an oligopeptidase bound to the outer cell membrane of a number of cells including a limited number of cancer tumor types (Turner A J (1998) Neprilysin. In *Handbook of proteolytic enzymes*, Barrett A J, Rawlings N D, Woessne J F (eds) pp 1108–1111. Academic Press: San Diego). Since it is also present in high concentrations in the brush boarder of the proximal kidney tubule, and at lower levels in some colon tissue and a number of immune system cells such as B-lymphocytes it may contribute to systemic activation of peptidyl prodrugs. This added systemic activation could lead to increased toxicity to normal tissues when compared to a peptidyl prodrug that is not a CD10 substrate. CD10 cleaves poorly when glycine or alanine is present in the P1' cleavage site but cleaves well when Leu is present in the P1' site (Pozsgay et al., "Substrate and inhibitor Studies of Thermolysin-like Neutral Metalloendopeptidase From Kidney Membrane Fractions. Comparison with Bacterial Thermolysin," *Biochemistry*, 25: 1292–1299 (1986)) thus Suc Leu-Ala-Gly-Dox is expected to be poorly cleaved by CD10 compared to Suc-Leu-Ala-Leu-Dox. This result is demonstrated in Example 15. When mice were given equimolar doses, the resulting plasma Dox exposure was much less with the CD10 cleavable compound (Example 10) despite the fact that the rate of hydrolysis by trouase (or TOP) of the two compounds was about the same (Example 2). As expected from the lower plasma Dox exposure, the non-CD10 cleavable peptidyl prodrug was also much safer when tested in a mean tolerated dose study (Examples 5 and 6). Thus, when treating a non-CD10 containing tumor, the preferred embodiment of this invention is a compound that is activated by TOP but not by CD10 such as Suc-Leu-Ala-Gly-Dox.

Stabilizing Group

An important portion of the prodrug is the stabilizing group, which serves to protect the prodrug compound from cleavage in circulating blood when it is administered to the patient and allows the prodrug to reach the vicinity of the target cell relatively intact. The stabilizing group typically protects the prodrug from cleavage by proteinases and peptidases present in blood, blood serum, and normal tissue. Particularly, in the preferred embodiment, where the stabilizing group caps the N-terminus of the oligopeptide, and is therefore sometimes referred to as an N-cap or N-block, the stabilizing group serves to ward against peptidases to which the prodrug may otherwise be susceptible.

Ideally, the stabilizing group is useful in the prodrug of the invention if it serves to protect the prodrug from degradation, i.e., cleavage, when tested by storage of the prodrug compound in human blood at 37° C. for 2 hours and results in less than 20%, preferably less than 2%, cleavage of the prodrug by the enzymes present in the human blood under the given assay conditions.

More particularly, the stabilizing group is either (1) other than an amino acid, or (2) an amino acid that is either (i) a non-genetically-encoded amino acid having four or more carbons or (ii) aspartic acid or glutamic acid attached to the N-terminus of the oligopeptide at the β-carboxyl group of aspartic acid or the γ-carboxyl group of glutamic acid.

For example, dicarboxylic (or a higher order carboxylic) acid or a pharmaceutically acceptable salt thereof may be used as a stabilizing group. Since chemical radicals having more than two carboxylic acids are also acceptable as part of the prodrug, the end group having dicarboxylic (or higher order carboxylic) acids is an exemplary N-cap. The N-cap may thus be a monoamide derivative of a chemical radical containing two or more carboxylic acids where the amide is attached onto the amino terminus of the peptide and the remaining carboxylic acids are free and uncoupled. For this purpose, the N-cap is preferably succinic acid, adipic acid, glutaric acid, or phthalic acid, with adipic acid and succinic acid being most preferred. Other examples of useful N-caps in the prodrug compound of the invention include diglycolic acid, fumaric acid, naphthalene dicarboxylic acid, pyroglutamic acid, acetic acid, 1 or 2, naphthylcarboxylic acid, 1,8-naphthyl dicarboxylic acid, aconitic acid, carboxycinnamic acid, triazole dicarboxylic acid, gluconic acid, 4-carboxyphenyl boronic acid, a $(PEG)_n$-analog such as polyethylene glycolic acid, butane disulfonic acid, maleic acid, isonipecotic acid, and nipecotic acid.

In some instances, intravascular administration of an aggregating positively charged prodrug in mice resulted in acute toxicity. However, no such toxicity was observed when the charge on this prodrug was reversed by derivitization with a negatively charged stabilizing group. Many cytotoxic compounds inherently have low solubility. Positively charged anthracyclines for example may form aggregates at high concentration and these aggregates may induce intravenous coagulation when the aggregates are administered intravenously. Since many oligopeptides have exposed, positively-charged amino termini at physiological pH, these aggregates may form a polypositively charged surface in vivo and induce a coagulation cascade within a few minutes of administration. This has the potential for rendering any positively charged prodrugs that form aggregates unsuitable for therapeutic use.

As described in greater detail in PCT/US99/30393, one way of addressing such a potentially dangerous obstacle is to utilize the stabilizing group on the peptide chain N-terminus of a negatively charged or a neutral functionality. For example, the use of succinyl as a stabilizing group on the prodrug alleviates the prodrug's acute toxicity. It is believed that the stabilizing group reduces interaction between the compound and endothelial cell that line blood vessels. This solves an important problem in the use of peptide prodrugs as practical therapies for intravenous use in humans.

Oligopeptide

Oligopeptides are generally defined as polypeptides of short length. An oligopeptide useful in the prodrug of the invention is three amino acids in length, however.

The oligopeptide has a formula or sequence (shown in the typical amino-terminus to carboxy-terminus orientation) $AA^3$-$AA^2$-$AA^1$ wherein each AA independently represents any amino acid. This corresponds to a position sequence P1-P1'-P2'. The trouase is believed to cleave between the P1 and P1' positions, i.e., the linkage between $AA^3$ and $AA^2$ of the oligopeptide.

The oligopeptide is written in the conventional manner with the carboxyl-terminus (or C-terminus) at the right and the amino-terminus (or N-terminus) at the left. Thus, in the formula described, above, $AA^1$ is the carboxyl-terminus.

In the invention of PCT/US99/30393, the oligopeptide portion of the prodrug described included a blocking, non-genetically-encoded amino acid, as $AA^4$ of the oligopeptide sequence or position P2 of the position sequence, according to the numbering scheme described above. The tripeptide prodrug of the present invention does not require such a blocking amino acid nor any other amino acid at position $AA^4$. Despite the short length of the oligopeptide portion of the prodrug herein described, the selectivity for cleavage of the prodrug by a trouase is maintained.

Preferred Amino Acids

Unless otherwise indicated, all amino acids are in the L configuration. Although any amino acids may be present in the oligopeptide portion of the prodrug, certain amino acids are preferred:

In the P1 or $AA^3$ position, one of the following amino acids is most preferred: Leucine, Sarcosine, Tyrosine, Phenylalanine, p-Cl-Phenylalanine, p-Nitrophenylalanine, Valine, Norleucine, Norvaline, Phenylglycine, Tryptophan, tetrahydroisoquinoline-3-carboxylic acid, 3-Pyridylalanine, Alanine, Glycine, or 2-Thienylalanine. Also preferred are Methionine or Proline in the P1 position.

In the P1' position, $AA^2$ is most preferably selected from one of the following amino acids: Alanine, Leucine, Tyrosine, Glycine, Serine, 3-Pyridylalanine, or 2-Thienylalanine. Also preferred in this position are Aminoisobutyric Acid, Threonine, or Phenylalanine.

In the P2' position or $AA^1$ position, one of the following amino acids is most preferably present: Leucine, Phenylalanine, Isoleucine, Alanine, Glycine, Tyrosine, 2-Naphthylalanine, or Serine.

Oligopeptides useful in the prodrug of the invention include the following, also shown in Table 1: Leu-Ala-Leu, Tyr-Ala-Leu, Met-Ala-Leu, Tyr-Ala-Ile, Phe-Gly-Leu, Met-Gly-Leu, Met-Gly-Ile, Phe-Gly-Ile, Met-Gly-Phe, Leu-Ala-Gly, Nle-Ala-Leu, Phe-Gly-Phe, and Leu-Tyr-Leu.

TABLE 1

| No: | $(AA_3)$ P1 | $(AA_2)$ P1' | $(AA_1)$ P2' |
|---|---|---|---|
| 1 | Leu | Ala | Leu |
| 2 | Tyr | Ala | Leu |
| 3 | Met | Ala | Leu |
| 4 | Tyr | Ala | Ile |
| 5 | Phe | Gly | Leu |
| 6 | Met | Gly | Leu |
| 7 | Met | Gly | Ile |
| 8 | Phe | Gly | Ile |
| 9 | Met | Gly | Phe |
| 10 | Leu | Ala | Gly |
| 11 | Nle | Ala | Leu |
| 12 | Phe | Gly | Phe |
| 13 | Leu | Tyr | Leu |

Screening with TOP

TOP is an important enzyme that may be utilized for selecting oligopeptides for further use and, therefore, another aspect of the invention is an oligopeptide cleavable by TOP of the formula $AA^3$-$AA^2$-$AA^1$ wherein each AA independently represents an amino acid. The oligopeptide may be linked to a therapeutic agent and/or a stabilizing group when testing for cleavability by TOP.

Therapeutic Agents

Therapeutic agents that are particularly advantageous to modify to a prodrug form according to the invention are those with a narrow therapeutic window. A drug or therapeutic agent with a narrow therapeutic window is one in which the dose at which toxicity is evident, by general medical standards, is very close to the dose at which efficacy is evident.

The therapeutic agent conjugated to the stabilizing group and oligopeptide and, optionally, the linker group to form the prodrug of the invention may be useful for treatment of cancer, inflammatory disease, or some other medical condition. Preferably, the therapeutic agent is selected from the following classes of compounds: Alkylating Agents, Antiproliferative agents, Tubulin Binding agents, Vinca Alkaloids, Enediynes, Podophyllotoxins or Podophyllotoxin derivatives, the Pteridine family of drugs, Taxanes, Anthracyclines, Dolastatins, Topoiosomerase inhibitors, Maytanisoids, or Platinum coordination complex chemotherapeutic agents.

Particularly, the therapeutic agent is advantageously selected from the following compounds: or a derivative or analog thereof Doxorubicin, Daunorubicin, Viniblastine, Vincristine, Calicheamicin, Etoposide, Etoposide phosphate, CC-1065, Duocarmycin, KW-2189, Methotrexate, Methopterin, Aminopterin, Dichloromethotrexate, Docetaxel, Paclitaxel, Epithiolone, Combretastatin, Combretastatin $A_4$ Phosphate, Dolastatin 10, Dolastatin 11, Dolastatin 15, Topotecan, Camptothecin, Mitomycin C, Porfiromycin, 5-Fluorouracil, 6-Mercaptopurine, Fludarabine, Tamoxifen, Cytosine arabinoside, Adenosine Arabinoside, Colchicine, Carboplatin, cis-Platin, Maytansine, Mitomycin C, Bleomycin, Melphalan, Chloroquine, or Cyclosporin A. By derivative is intended a compound that results from reacting the named compound with another chemical moiety, and includes a pharmaceutically acceptable salt, acid, base or ester of the named compound. By analog is intended a compound having similar structural and functional properties, such as biological activities, to the named compound.

Linker Groups

A linker group between the oligopeptide and the therapeutic agent may be advantageous for reasons such as the following:

1. As a spacer for steric considerations in order to facilitate enzymatic release of the $AA^1$ amino acid or other enzymatic activation steps.
2. To provide an appropriate attachment chemistry between the therapeutic agent and the oligopeptide.
3. To improve the synthetic process of making the prodrug conjugate (e.g., by pre-derivitizing the therapeutic agent or oligopeptide with the linker group before conjugation to enhance yield or specificity.)
4. To improve physical properties of the prodrug.
5. To provide an additional mechanism for intracellular release of the drug.

Linker structures are dictated by the required functionality. Examples of potential linker chemistries are hydrazide, ester, ether, and sulphydryl. Amino caproic acid is an example of a bifunctional linker group. When amino caproic acid is used in the linker group, it is not counted as an amino acid in the numbering scheme of the oligopeptide.

The optionally present linker group is not cleavable by TOP, i.e. it is not cleavable by TOP under physiological conditions.

Screening of the Prodrug

As mentioned previously, the synthesized prodrug ideally should be tested against a test standard which consists of Suc-βAla-Leu-Ala-Leu conjugated to a therapeutic agent or marker. The same therapeutic agent or marker that was used to make the prodrug compound should be conjugated to the Suc-βAla-Leu-Ala-Leu to make the test standard. The rates of hydrolysis of the synthesized tripeptide prodrug and the test standard by a trouase are compared under common experimental conditions. Example 2 below provides an exemplary scheme for performing this test. The tripeptide prodrugs of the invention are preferably cleaved at a rate that is a fractional portion of the standard rate of cleavage for the test standard. The most useful prodrugs of the present invention cleave at a fractional portion equal to 10–80% of the rate of cleavage of the test standard. Even more preferably, a prodrug of the present invention cleaves at a rate that is 30–65% of the rate of cleavage of the test standard.

The disclosure of making and using tripeptide prodrugs taught herein provides a useful alternative to prior teachings of prodrug design. As illustrated in the examples below, the prodrugs of the invention are efficacious and well-tolerated in vivo in animal models. As such, the prodrugs are advantageously utilized in therapy.

An especially useful embodiment is a compound that is cleavable by a trouase but resistant to cleavage by CD10 or other systemic or blood enzymes.

Prodrug Design

A method of designing a prodrug is another aspect of the invention and entails initially selecting an oligopeptide of three amino acids. Then the oligopeptide is linked at a first attachment site of the oligopeptide to a stabilizing group that hinders cleavage of the oligopeptide by enzymes present in whole blood, and directly or indirectly linked to a therapeutic agent at a second attachment site of the oligopeptide. The linkage of the oligopeptide to the therapeutic agent and the stabilizing group may be performed in any order or concurrently. The resulting conjugate is tested for cleavability by a trouase, such as TOP. Preferably, the resulting conjugate is tested for cleavage under a given experimental condition, and the conjugate is selected as a prodrug if the test rate of cleavage is 10–80%, or more preferably 30–65%, of a standard rate of cleavage. The standard rate of cleavage is tested on a test standard by the trouase under the same given experimental condition. The test standard consists of a conjugate of Suc-βAla-Leu-Ala-Leu and the therapeutic agent (or the marker, in the case of the article of manufacture described below). The resulting conjugate may also be tested for stability in whole blood. Test compounds stable in whole blood are selected. The first attachment site is usually the N-terminus of the oligopeptide but may be the C-terminus of the oligopeptide or another part of the oligopeptide. The second attachment site is usually the C-terminus of the oligopeptide, but may be the N-terminus of the oligopeptide or another part of the oligopeptide. A prodrug designed by such a method is also part of the invention.

Further, the invention includes a method for decreasing toxicity of a therapeutic agent that is intended for administration to a patient. Specifically, a modified, prodrug form of the therapeutic agent is formed by directly or indirectly linking the therapeutic agent to an oligopeptide of three amino acids that is cleavable by a trouase, or more specifically, cleavable by TOP. The oligopeptide is also linked to a stabilizing group. The prodrug thus formed should be selectively cleaved by the trouase at a test rate of cleavage that is 10–80%, or more preferably 30–65%, of a standard rate of cleavage resulting from the test standard, as described. The prodrug provides for decreased toxicity of the therapeutic agent when administered to the patient. The modification of the therapeutic agent in this manner also allows for administration of an increased dosage of the therapeutic agent to the patient relative to the dosage of the therapeutic agent in unconjugated form.

Pharmaceutical Compositions

The invention also includes a pharmaceutical composition comprising a compound, particularly a prodrug compound, according to the invention and, optionally, a pharmaceutically acceptable carrier, for example an adjuvant, vehicle, or the like.

The invention also relates to the use of the pharmaceutical composition for the preparation of a medicinal product intended for the treatment of a medical condition.

The pharmaceutical composition may, for example, be administered to the patient parenterally, especially intravenously, intramuscularly, or intraperitoneally. Pharmaceutical compositions of the invention for parenteral administration comprise sterile, aqueous or nonaqueous solutions, suspensions, or emulsions. As a pharmaceutically acceptable solvent or vehicle, propylene glycol, polyethylene glycol, injectable organic esters, for example ethyl oleate, or cyclo-dextrins may be employed. Isotonic saline may be part of the pharmaceutical composition. These compositions can also comprise wetting, emulsifying and/or dispersing agents.

The sterilization may be carried out in several ways, for example using a bacteriological filter, by incorporating sterilizing agents in the composition or by irradiation. They may also be prepared in the form of sterile solid compositions, which may be dissolved at the time of use in sterile water or any other sterile injectable medium.

The pharmaceutical composition may also comprise adjuvants that are well known in the art (e.g., vitamin C, antioxidant agents, etc.) and capable of being used in combination with the compound of the invention in order to improve and prolong the treatment of the medical condition for which they are administered.

Doses for administration to a patient of the compounds according to the invention are generally at least the usual doses of the therapeutic agents known in the field, described in Bruce A. Chabner and Jerry M. Collins, Cancer Chemotherapy, Lippincott Ed., ISBN 0-397-50900-6 (1990) or they may be adjusted, within the judgment of the treating physician, to accommodate the superior effectiveness of the prodrug formulations or the particular circumstances of the patient being treated. Hence, the doses administered vary in accordance with the therapeutic agent used for the preparation of the compound according to the invention.

Treatment of Patients with Prodrug Compound

A method for the therapeutic treatment of a medical condition that involves administering, preferably parenterally and more preferably intravenously, to the patient a therapeutically effective dose of the pharmaceutical composition is also within the scope of the invention. Thus, the method generally entails administering to the patient a therapeutically effective amount of a compound comprising:

(1) a therapeutic agent capable of entering a target cell,
(2) an oligopeptide of the formula $AA^3$-$AA^2$-$AA^1$ wherein each AA independently represents an amino acid,
(3) a stabilizing group, and
(4) optionally, a linker group not cleavable by a trouase,
wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
wherein the stabilizing group hinders cleavage of the oligopeptide by enzymes present in whole blood, and
wherein the compound is selectively cleaved by the trouase, preferably TOP. The most useful compounds result in a test rate of cleavage of 10–80% of a standard rate of cleavage under a given experimental condition. The standard rate of cleavage is tested on a test standard by the trouase under the same experimental condition and the test standard consists of a conjugate of Suc-βAla-Leu-Ala-Leu and the therapeutic agent. More preferably, the test rate of cleavage of the compound is 30–65% of the standard rate of cleavage.

The prodrug compound is useful for the treatment of many medical conditions including cancer, neoplastic diseases, tumors, inflammatory diseases, and infectious diseases. Examples of preferred diseases are breast cancer, colorectal cancer, liver cancer, lung cancer, prostate cancer, ovarian cancer, brain cancer, and pancreatic cancer. Formulated in pharmaceutically acceptable vehicles (such as isotonic saline), the prodrug compound can be administered to animals or humans in intravenous doses ranging from 0.05 mg/kg/dose/day to 300 mg/kg/dose/day. It can also be administered via intravenous drip or other slow infusion method.

Human patients are the usual recipients of the prodrug of the invention, although veterinary usage is also contemplated.

Diagnosis or Assay

An article of manufacture, such as a kit, for diagnosis or assay is also within the scope of the invention. Such an article of manufacture would preferably utilize a compound as described above, except that a marker, such as coumarin, is conjugated to the oligopeptide and stabilizing group instead of a therapeutic agent. A marker intends any moiety that can be conjugated to the oligopeptide and is readily detectable by any method known in the art. At least one reagent useful in the detection of the marker is typically included as part of the kit. Thus, the article of manufacture would include a compound and optionally a least one reagent useful in the detection of a marker. More particularly, the compound comprises:

(a) a marker,
(b) an oligopeptide of the formula $AA^3$-$AA^2$-$AA^1$ wherein each AA independently represents an amino acid,
(e) a stabilizing group, and
(d) optionally, a linker group not cleavable by TOP or another trouase,
  wherein the oligopeptide is directly linked to the stabilizing group at a first attachment site of the oligopeptide and the oligopeptide is directly linked to the marker or indirectly linked through the linker group to the marker at a second attachment site of the oligopeptide,
  wherein the stabilizing group hinders cleavage of the oligopeptide by enzymes present in whole blood, and
  wherein the compound is selectively cleaved by the trouase. As before, most useful are those compounds that cleave at a test rate of cleavage of 10–80% of a standard rate of cleavage under an experimental condition, the standard rate of cleavage tested on a test standard by the trouase under the same experimental condition, the test standard consisting of a conjugate of Suc-βAla-Leu-Ala-Leu and the marker. The article of manufacture may be used, for example, with patient samples to diagnose tumors or to identify patients susceptible to treatment by prodrug therapy.

Process Chemistry General Procedures

Oligopeptide: General Method for the Synthesis of Peptides

The peptide, or oligopeptide, sequences in the prodrug conjugates of this invention may be synthesized by the solid phase peptide synthesis (using either Boc or Fmoc chemistry) methods or by solution phase synthesis. The general Boc and Fmoc methods are widely used and are described in the following references: Merrifield, *J. A. Chem. Soc.*, 88:2149 (1963); Bodanszky and Bodanszky, *The Practice of Peptide Synthesis*, Springer-Verlag, Berlin, 7–161 (1994); Stewart, *Solid Phase Peptide Synthesis*, Pierce Chemical, Rockford, (1984).

General Fmoc Solid Phase Method

Figure 3:
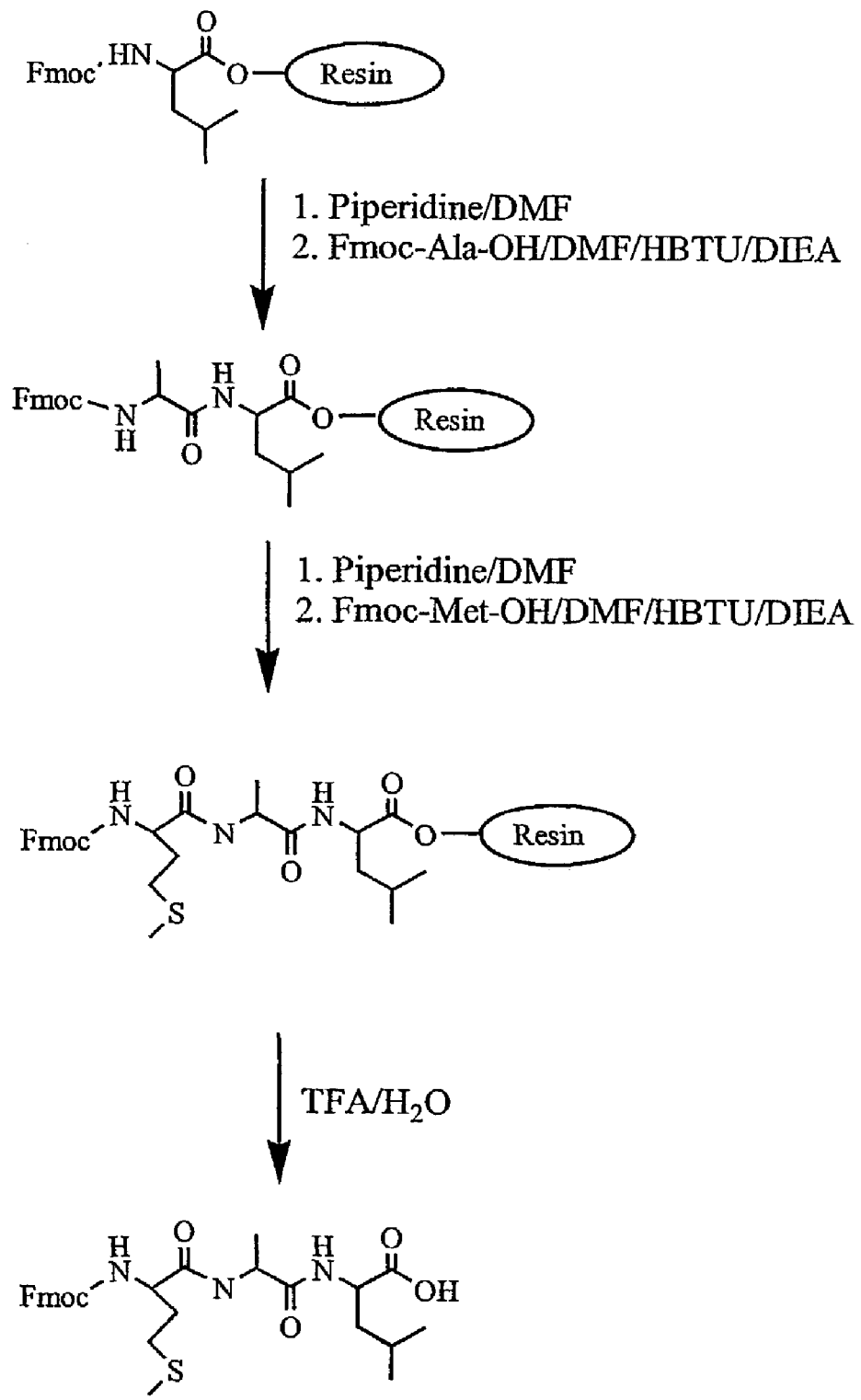
FIG. 3 illustrates a solid phase synthesis of Fmoc-Met-Ala-Leu, a typical intermediate of the invention.

Using the preferred solid phase synthesis method, either automated or manual, a peptide of desired length and sequence is synthesized through the stepwise addition of amino acids to a growing chain which is linked to a solid resin. Examples of useful Fmoc compatible resins include, but are not limited to, Wang resin, HMPA-PEGA resin, Rink acid resin, or a hydroxyethyl-photolinker resin. The C-terminus of the peptide chain is covalently linked to a polymeric resin and protected α-amino acids were added in a stepwise manner with a coupling reagent. A preferred α-amino protecting group is the Fmoc group, which is stable to coupling conditions and can readily be removed under mild alkaline conditions. The reaction solvents are preferably but not limited to DMF, NMP, DCM, MeOH, and EtOH. Examples of coupling agents are: DCC, DIC, HATU, HBTU. Cleavage of the N-terminal protecting group is accomplished in 10–100% piperidine in DMF at 0–40° C., with ambient temperature being preferred. At the end of synthesis, the final Fmoc protecting group is removed using the above N-terminal cleavage procedure. The remaining peptide on resin is cleaved from the resin along with any acid sensitive side chain protecting groups by treating the resin under acidic conditions. For example, an acidic cleavage condition is a mixture of trifluoroacetic acid (TFA) in dichloromethane. If the hydroxyethyl-photolinker resin is used, the appropriate wavelength for inducing cleavage is λ 365 nm ultraviolet light. A diagramatic representation of this process is given in FIG. 3.

General N-Cap Method via Solid Phase Synthesis

The preparation of N-terminus derivatized peptides is conveniently accomplished on solid phase. When the peptide synthesis is complete, the terminal Fmoc is removed while the peptide is still on the solid support. The N-cap of choice is coupled next using standard peptide coupling conditions onto the N-terminus of the peptide. On completion of the N-cap coupling the peptide is cleaved from the resin using the procedure described above.

General Boc Solid Phase Method

For the solid phase method using Boc chemistry, either the Merrifield resin or PAM resin is useful. The amino acids are coupled to the growing chain on solid phase by successive additions of coupling agent activated Boc-protected amino acids. Examples of coupling agents are: DCC, DIC, HATU, HBTU. The reaction solvents may be DMF, DCM, MeOH, and NMP. Cleavage of the Boc protecting group is accomplished in 10–100% TFA in DCM at 0–40° C., with ambient temperature being preferred. On completion of the peptide chain assembly the N-terminus protecting group (usually Boc) is removed as described above. The peptide is removed from the resin using liquid HF or trifluoromethane sulfonic acid in dichloromethane.

General Procedure for the Preparation of Fmoc Oligopeptide by Solution Phase Synthesis Alternatively, the prodrug peptide intermediate may be made via a solution phase synthesis, utilizing either Boc or Fmoc chemistry. In the diagrammatic presentation of the methods (FIG. 4), the C-terminal Leu tripeptide is generally used as an example, but it will be understood that similar reactions may be performed with other C-terminal tripeptides, as well. The peptide can be built up by the stepwise assembly in analogy to the solid phase method (in the N-terminal direction or in the C-terminal direction) or through the coupling of a dipeptide with a single amino acid.

Figure 4:
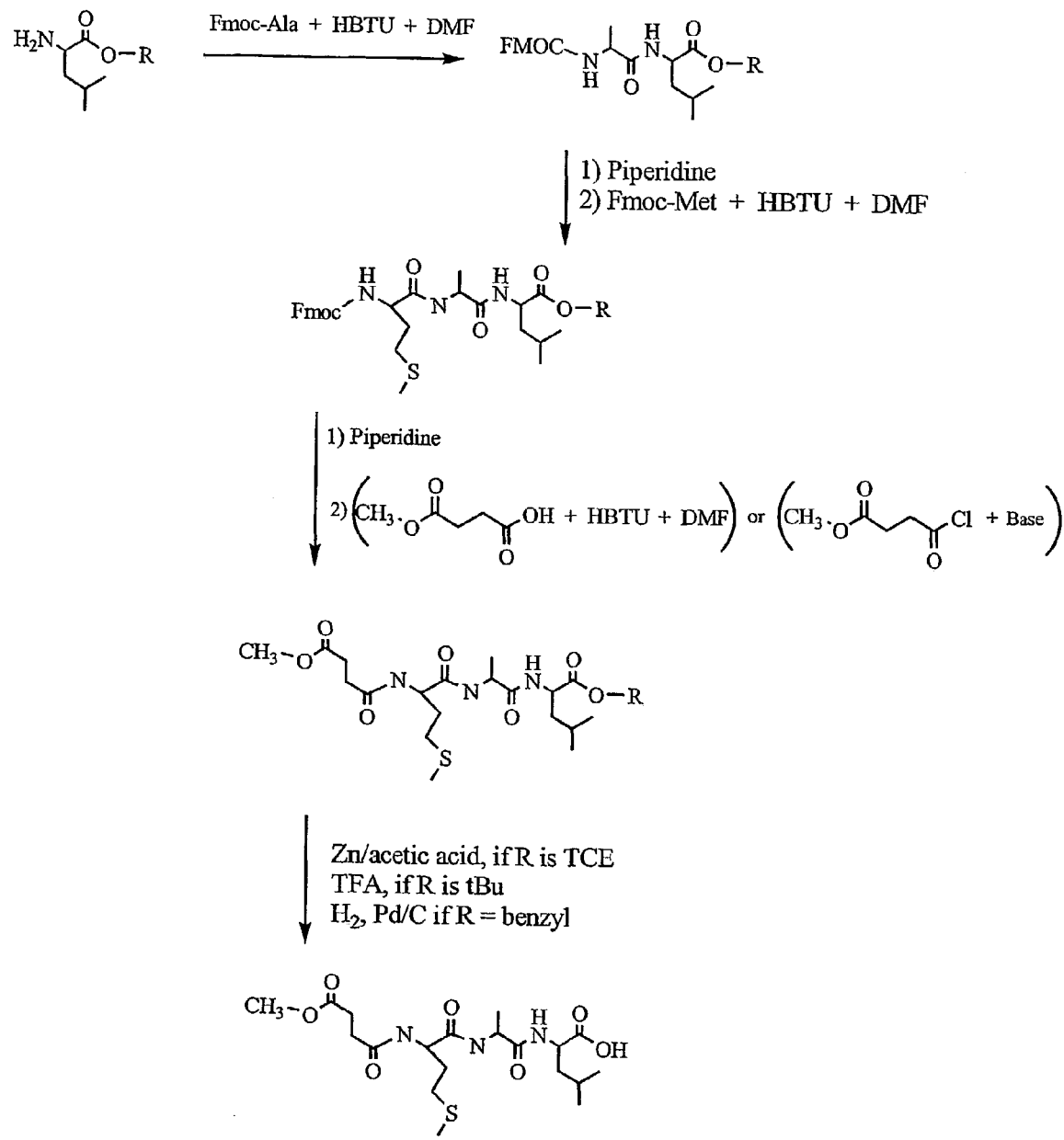
FIG. 4 illustrates a solution phase "Fmoc-route" synthesis of Methyl-succinyl-Met-Ala-Leu, a typical intermediate of the invention.

One method of solution phase synthesis is a stepwise building up of the prodrug peptide intermediate using Fmoc chemistry, shown in FIG. 4. The C-terminus must be protected to reduce the formation of side products. The C-terminal R group in FIG. 4 is Me, tBu, benzyl or TCE. (Note when the N-cap is methyl succinyl the C-terminus R group cannot be methyl.) Although DMF is given as the solvent, other solvents such as DMSO, $CH_3CN$, or NMP (or mixtures thereof) may be substituted therefor. Pyridine, $Et_3N$ or other bases may be substituted for piperidine in deprotecting the growing peptide chain protected amino terminus. Similarly, although HBTU is given in the diagram above as the activating agent, other activating agents such as DCC, DIC, DCC+HOBt, OSu, activated esters, azide, or triphenyl phosphoryl azide may be used. Additionally, the protected peptide acid chloride or acid bromide may be used to couple directly to the amino acid or peptide fragment. On completion of the oligopeptide assembly, the N-terminus is deprotected and the C-terminus protected peptide is ready to accept the desired N-cap.

Figure 5:
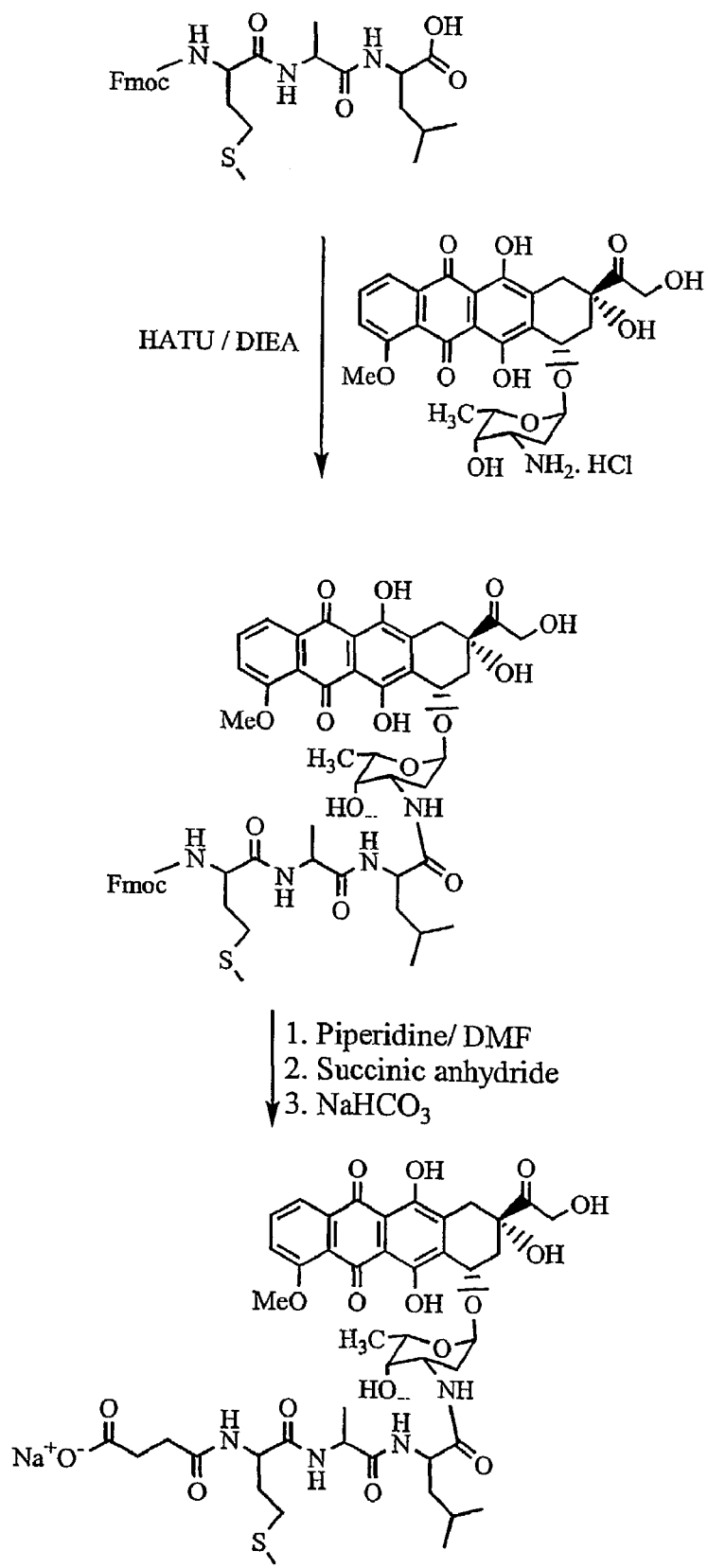
FIG. 5 illustrates an "Fmoc route" synthesis of a salt form of Suc-Met-Ala-Leu-DOX, a typical compound of the invention.

General Procedure for the Preparation of N-Cap Oligopeptide via Solution Phase Synthesis When constructing the N-capped oligopeptide by solution phase synthesis, the N-cap needs to be synthesized by a slightly modified procedure (FIG. 5). First the C-terminus of the Fmoc oligopeptide needs to be protected with an acid labile or hydrogenation sensitive protecting group compatible with the selective deprotection of the C-terminus over the N-cap. Then the Fmoc protecting group needs to be removed from the oligopeptide to reveal the N-terminus. With the N-terminus deprotected and the C-terminus protected, the oligopeptide is reacted with the activated hemiester of the desired N-cap. The N-cap can be activated using methods for activating amino acids such as DCC or HATU in base and an appropriate solvent. Alternatively, where the methyl-hemisuccinate is used, the coupling may also be done via methyl hemisuccinyl chloride (or other acid halide) (FIG. 4) using an inert solvent in the presence of an organic or inorganic base, such as DIEA, triethylamine or $Cs_2CO_3$. One example of such a synthesis can be by reacting methylhemisuccinate and Met-Ala-Leu benzyl ester. The coupling method can be any one of the methods generally used in the art (see for example: Bodanszky, M., *The Practice of Peptide Synthesis*, Springer Verlag, 185 (1984); Bodanszky, M., *Principles of Peptide Synthesis*, Springer Verlag, 159 (1984). The benzyl group then can be removed by catalytic hydrogenation providing the desired N-cap methylsuccinyl form of the oligopeptide. Other examples of suitable, selectively removable C-terminal protecting groups can be, but are not limited to, tBu, alkoxy-methyl and TCE. Other methods of accomplishing this step are described in the literature.

The reaction conditions are well known in the art and detailed in the citations given. The advantage of the above described methods is the facile purification of the product produced by solution phase synthesis.

Prodrug Conjugate

General Methods for the Conjugation and Deprotection Steps

The prodrugs described herein can be synthesized by coupling an Fmoc form (which means Fmoc is attached to the N-terminus of the oligopeptide) of the oligopeptide with daunorubicin, or doxorubicin, or any appropriate therapeutic agent using any of the standard activating reagents used in peptide synthesis (FIG. 5). The solvent may be toluene, ethyl acetate, DMF, DMSO, $CH_3CN$, NMP, THF, DCM or any other suitable inert solvent as is known in the art and the reagents are soluble therein. The preferred solvents are DMF and NMP. The appropriate temperature range is −25 to +25° C., with ambient temperature being preferred. The activating agent may be selected from one of the following: PyBOP, HBTU, HATU, EDC, DIC, DCC, DCC+HOBT, OSu activated esters, azide, or triphenylphosphorylazide. HBTU or HATU is the preferred activating agent. Alternatively, the acid chloride or the acid bromide of the protected peptide can also be used for this coupling reaction. 2–4 equivalents, advantageously 2–2.5 equivalents of a base is required for the coupling reaction. The base can be selected from inorganic bases such as $CsCO_3$, Na- or $K_2CO_3$, or organic bases, such as TEA, DIEA, DBU, DBN, DBO, pyridine, substituted pyridines, N-methyl-morpholine etc., preferably TEA, or DIEA. The reaction can be carried out at temperatures between −15° C. and 50° C., advantageously between −10° C. and 10° C. The reaction time is between 5–90 minutes and is advantageously 20–40 minutes. The product is isolated by pouring the reaction mixture into water and filtering the precipitate formed. The crude product can be further purified by recrystallization from DCM, THF, ethyl acetate, or acetonitrile, preferably from dichloromethane or acetonitrile. The isolated Fmoc form of the (oligopeptide)-(therapeutic agent) conjugate is then deprotected over 2–90 minutes, preferably 3–8 minutes, using a ten- to hundred-fold excess of base at a temperature between −10° C. and 50° C. Ideally, 5–60 equivalents of the base are preferred. Piperidine is the preferred base to deprotect Fmoc groups. The deprotected amino terminus of the (oligopeptide)-(therapeutic agent) conjugate is acylated by a diacid anhydride as an activated hemiester to give the final N-cap form of the oligopeptide-therapeutic agent.

Figure 6:
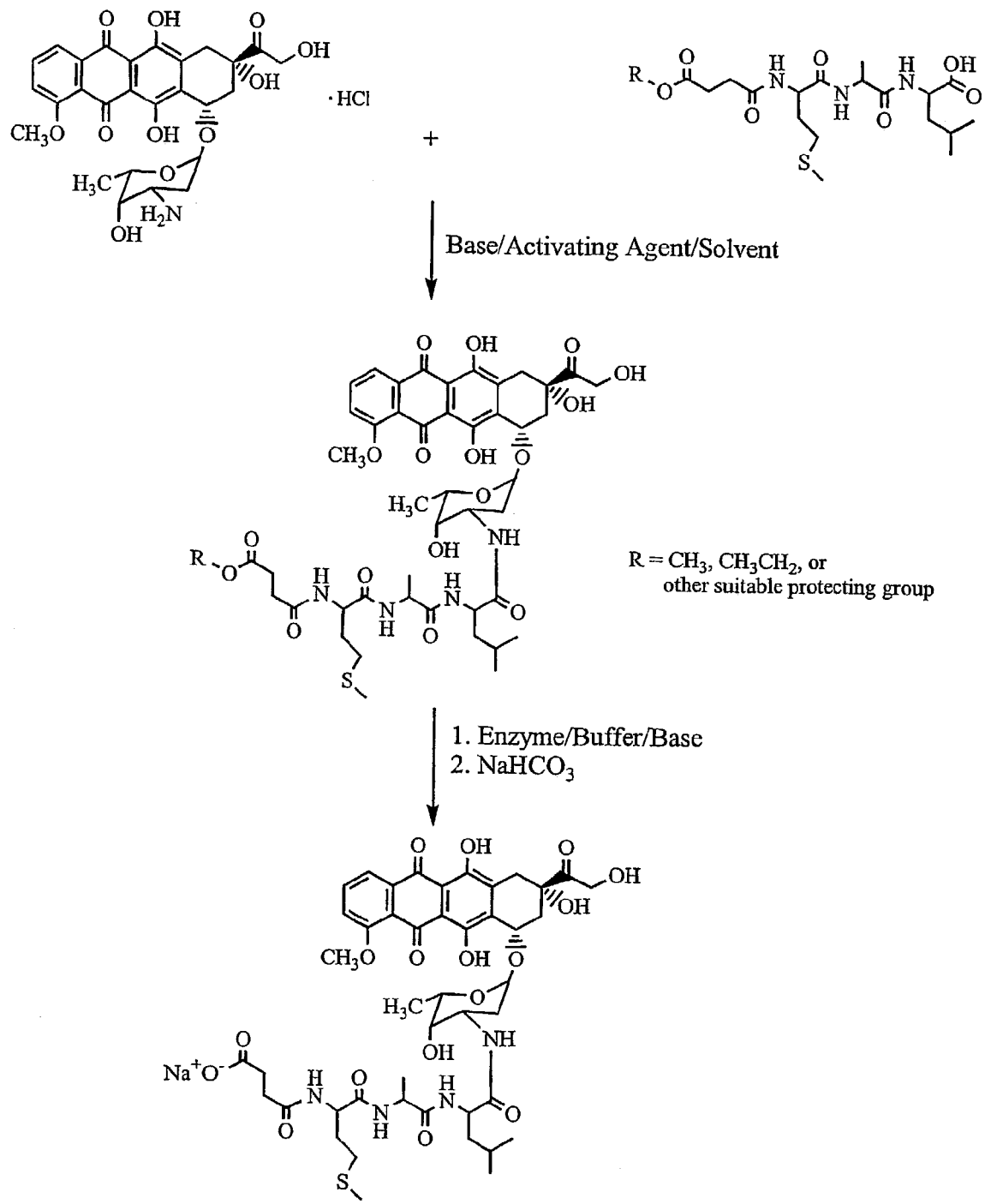
FIG. 6 illustrates an "Ester route" synthesis of a salt form of Suc-Met-Ala-Leu-DOX, a typical compound of the invention.

Alternatively, the final prodrug can be similarly prepared from the protected N-cap form of the oligopeptide such as a methylhemiester form of succinyl-N-cap oligopeptide and conjugated to a therapeutic agent. This method is illustrated in FIG. 6.

The (protected N-Cap)-(oligopeptide)-(therapeutic agent) conjugate is now deprotected by methods compatible to the stability of the therapeutic agent. For example, anthracyclines may be protected with a methyl group and deprotected with an esterase. For other therapeutic agents we might select benzyl protecting groups and catalytic hydrogenation may be chosen to deprotect.

Conversion to the salt form of the negatively charged (N-cap)-(oligopeptide)-(therapeutic agent) is carried out with a solvent selected from the following group: alcohol (including methanol, ethanol, or isopropanol), water, acetonitrile, tetrahydrofuran, diglyme or other polar solvents. The sodium source is one molar equivalent of $NaHCO_3$, NaOH, $Na_2CO_3$, NaOAc, $NaOCH_3$ (in general sodium alkoxide), or NaH. An ion exchange column charged with $Na^+$ (such as strong or weak ion exchangers) is also useful for this last step of making the salt form of the (N-cap)-(oligopeptide)-(therapeutic agent) when appropriate. Sodium is described in this application as an example only.

Generally, the prodrug may be converted to a pharmaceutically acceptable salt form to improve solubility of the prodrug. The (N-cap)-(oligopeptide)-(therapeutic agent) is neutralized with a pharmaceutically acceptable salt, e.g., $NaHCO_3$, $Na_2CO_3$, NaOH tris(hydroxymethyl)aminomethane, $KHCO_3$, $K_2CO_3$, $CaCO_3$, $NH_4OH$, $CH_3NH_2$, $(CH_3)_2NH$, $(CH_3)_3N$, acetyltriethylammonium. The preferred salt form of prodrug is sodium and the preferred neutralizing salt is $NaHCO_3$.

It is well documented that anthracycline type molecules, including doxorubicin and daunorubicin form gels in organic solvents in very low concentrations (Matzanke, B. F., et al., *Eur. J. Biochem.*, 207:747–55 (1992); Chaires, J. B., et al., *Biochemistry*, 21:3927–32 (1982); Hayakawa, E., et al., *Chem. Pharm. Bull.*, 39:1282–6 (1991). This may be a considerable obstacle to getting high yields of clean product when making peptide anthracycline conjugates. The gel formation contributes to the formation of undesirable side reactions. One way to minimize this problem is to use very dilute solutions (1–2%) for the coupling reaction, however it is not practical in a process environment (large amounts of waste, complicated isolation). To overcome this problem, urea or other chaotropic agents may be used to break up the strong hydrophobic and hydrogen bonding forces forming the gel. Thus if the coupling reaction is carried out in a urea-containing solvent, advantageously a 20% to saturated solution of urea in DMF or NMP, the side reactions can be kept below 2% even if the concentration of reactants exceeds 10%. This procedure makes the conjugation step practical at high concentrations and produces good yields.

General Enzyme Method

Hydrolysis of protected N-cap-oligopeptide therapeutic agents to the full N-cap compound catalyzed by acids or bases leads to complex reaction mixtures due to the lability of many therapeutic agents even under moderately acidic or basic conditions. Enzymes can promote the hydrolysis without destroying the substrate or the product. Enzymes suitable for this reaction can be esterases or lipases and can be in their natural, water soluble forms or immobilized by cross coupling, or attachment to commercially available solid support materials. Of the soluble enzymes evaluated, *Candida Antarctica* "B" lipase (Altus Biologics) is especially useful. An example of an enzyme immobilized by cross coupling is ChiroCLEC-PC™ (Altus Biologics). *Candida Antarctica* "B" lipase (Altus Biologics) can be immobilized by reaction with NHS activated Sepharose™ 4 Fast Flow (American Pharmacia Biotech). The pH of the reaction mixture during the hydrolysis is carefully controlled and maintained by a pH-stat between 5.5 and 7.5, advantageously between 5.7 and 6.5, via controlled addition of NaHCO$_3$ solution. When the reaction is completed the product is isolated by lyophilization of the filtered reaction mixture. The immobilized enzymes remain on the filter cake and can be reused if desired.

General Allyl or Alkyl Ester Method

Figure 8:
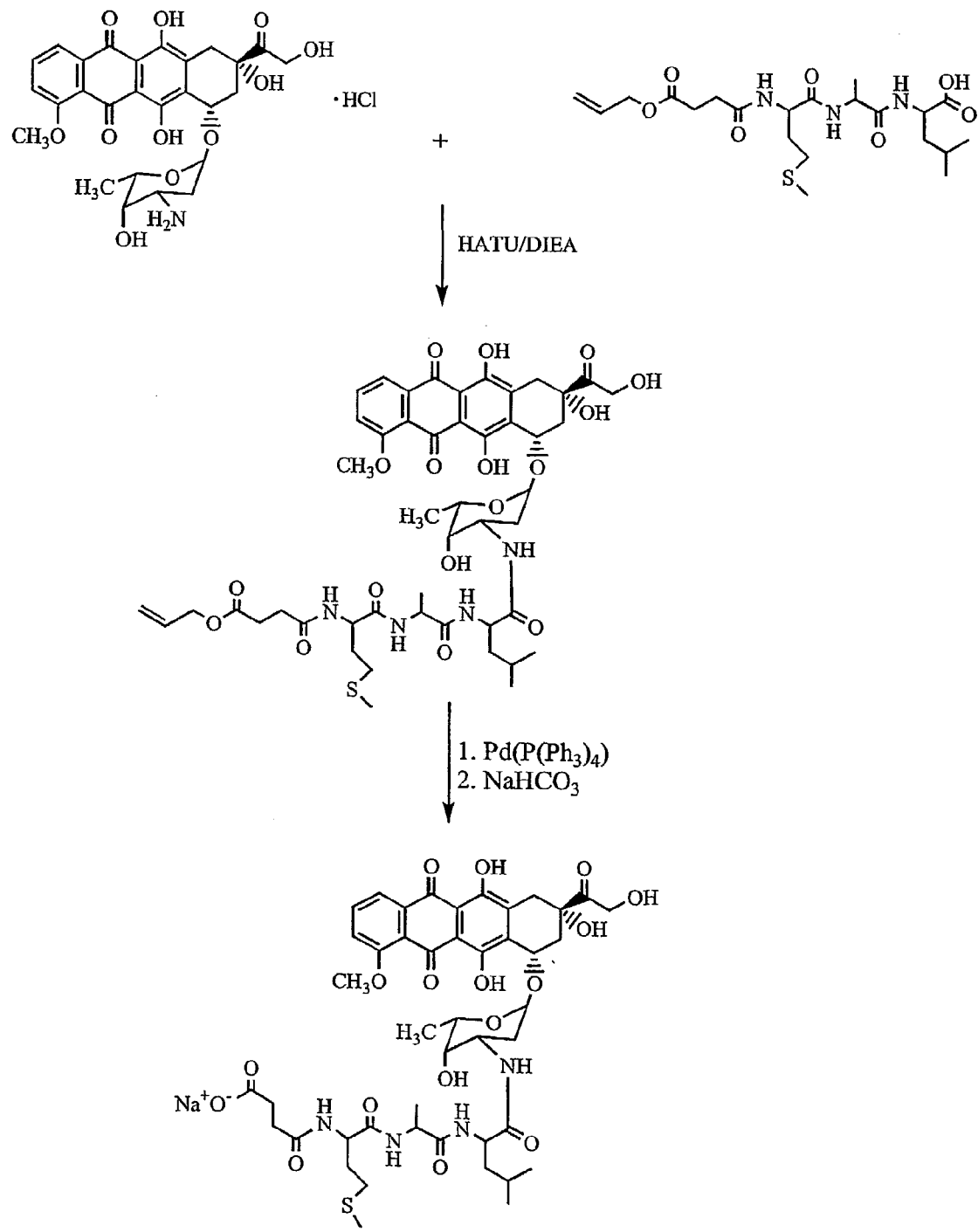
FIG. 8 illustrates an "Allyl ester route" synthesis of a salt form of Suc-Met-Ala-Leu-DOX, a typical compound of the invention.

The prodrug can also be prepared via coupling an allyl-hemiester or alkyl-hemiester form of the N-cap oligopeptide with a therapeutic agent and then liberating the free acid from the conjugate. FIG. 8 illustrates this process with Succinyl-Met-Ala-Leu and doxorubicin.

The coupling of allyl-succinyl-Met-Ala-Leu with doxorubicin can be carried out via any one of the oligopeptide conjugation methods.

Allyl-succinyl-Met-Ala-Leu-doxorubicin can also be synthesized by reacting allyl hemisuccinate, which was prepared via known methods (Casimir, J. R., et al., *Tet. Lett.* 36/19 3409 (1995)), with Met-Ala-Leu-doxorubicin similarly as coupling of the protected tripeptide precursors to doxorubicin was described in the previous methods, shown in FIG. 5. Suitable inert solvents are THF, dichloromethane, ethyl acetate, toluene, preferably THF from which the acid form of the product precipitates as the reaction progresses. The isolated acid is converted to its sodium salt as described earlier. Reaction times vary between 10–180 minutes, advantageously 10–60 minutes, at temperatures between 0–60° C., preferably 15–30° C.

Removal of the allyl or alkyl group can be done with Pd (0), or Ni(0), advantageously Pd(0) promoted transfer of the allyl or alkyl group to acceptor molecules, as it is well known in the art and documented in the professional literature (Genet, J-P, et al., *Tet. Lett.*, 50, 497, 1994; Bricout, H., et.al. *Tet. Lett.*, 54:1073 (1998), Genet, J-P. et.al. Synlett, 680 (1993); Waldmann, H., et.al., *Bioorg. Med. Chem.*, 7:749 (1998); Shaphiro, G., Buechler, D., *Tet. Lett.*, 35:5421 (1994)). The amount of catalyst can be 0.5–25 mol % to the substrate.

General Trityl or Substituted Trityl Method

Figure 7:
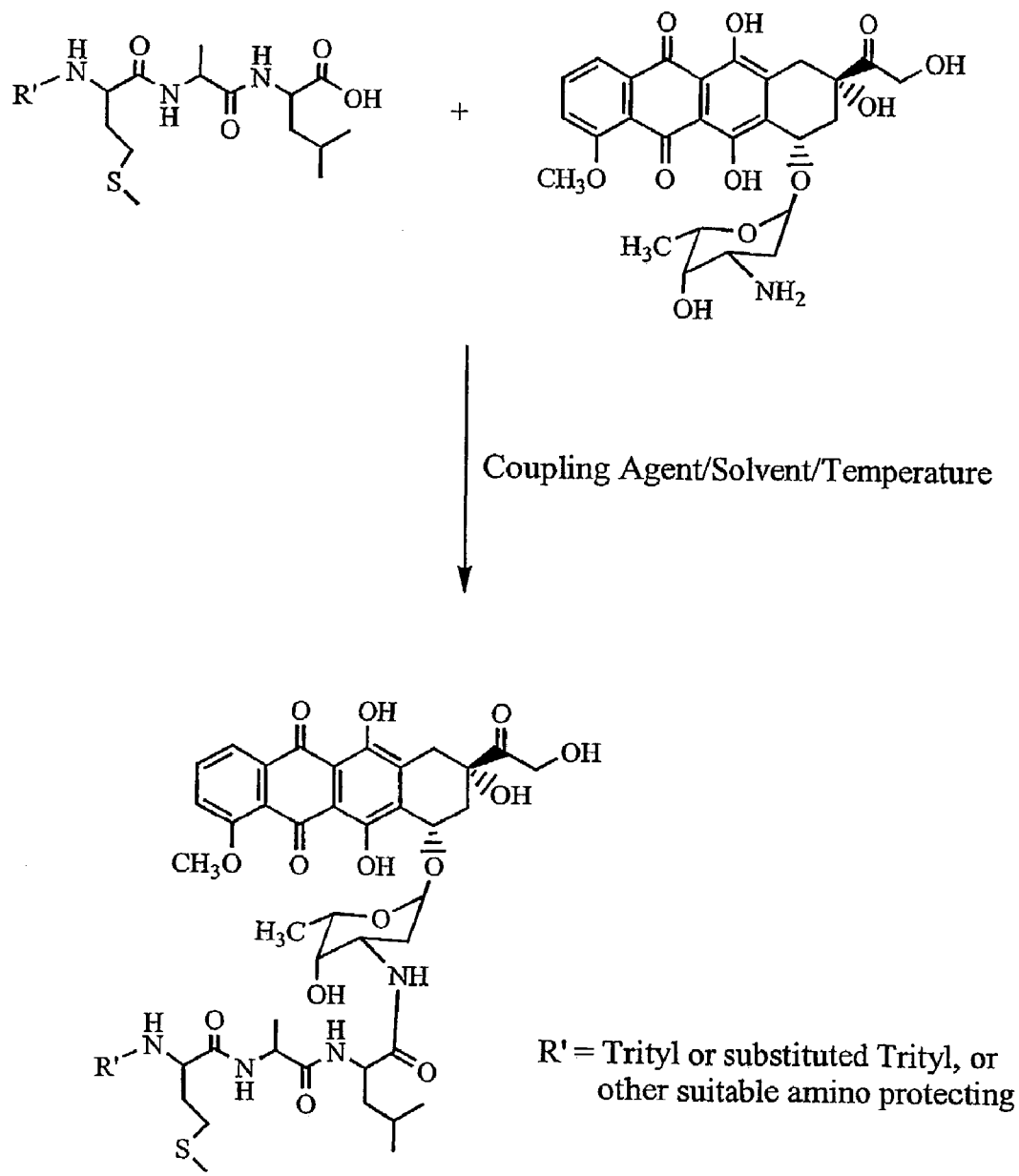
FIG. 7 illustrates a synthesis of an amino-protected Met-Ala-Leu-DOX, a typical intermediate of the invention.

The prodrug may also be synthesized via the method shown in FIG. 7. This approach utilizes an R'-oligopeptide, where R' is trityl or substituted trityl. The coupling of R'-oligopeptide with a therapeutic agent can be carried out via any one of the methods described earlier for conjugation of a protected oligopeptide with a therapeutic agent at 30–120 minutes at 0–20° C.

Removal of trityl or substituted trityl group can be achieved under acidic conditions to give the positively charged prodrug. This positively charged prodrug is N-capped as illustrated in FIG. 4 and described earlier. The trityl deprotection can be accomplished with acetic acid, formic acid and dilute hydrochloric acid.

The prodrug can be converted into (succinyl or glutaryl)-(oligopeptide)-(therapeutic agent) conjugate by reacting with succinic anhydride or glutaric anhydride. The solvent for coupling step DMF, DMSO, CH$_3$CN, NMP, or any other suitable solvent is known in the art. Succinyl or glutaryl oligopeptide therapeutic agents can be converted to any pharmaceutically acceptable salt.

General Inverse Direction Solid Phase Conjugation Method

The prodrug compound of the present invention can be synthesized by using solid phase chemistry via "step wise" inverse (from the N-terminal to the C-terminal) direction methods.

Figure 9:
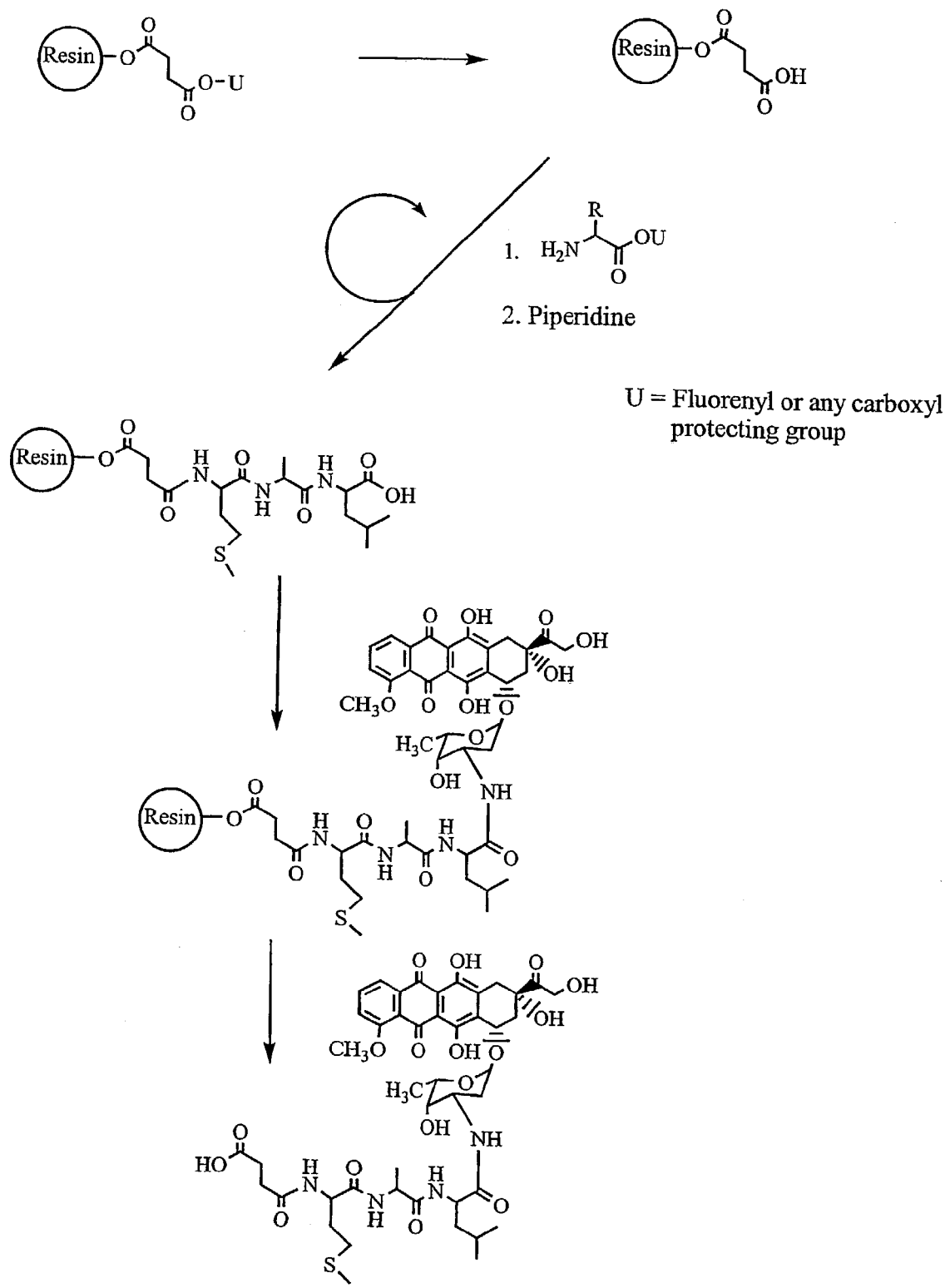
FIG. 9 illustrates a "Resin route" synthesis of Suc-Met-Ala-Leu-DOX, a typical compound of the invention.

One way is to use resins to immobilize a succinyl hemiester, for example succinyl-mono-benzyl ester or -allyl ester. Examples of resins could be selected are "Wang Resins" (Wang, S. S., *J. Am. Chem. Soc.*, 95:1328 (1973); Zhang, C., Mjaili, A. M. M., *Tet. Lett.*, 37:5457(1996)), "Rink Resins" (Rink, H., *Tet. Lett.*, 28:3787 (1987)), "Trityl-, or substituted-trityl Resins" (Chen, C., et.al., *J. Am. Chem. Soc.*, 116:2661 (1994); Bartos, K. et.al., *Peptides, Proc. 22$^{nd}$ European Peptide Symposium* (1992); Schneider, C. H.; Eberle, A. N. (Eds.), *ESCOM, Leiden*, pp. 281 (1993). The immobilized ester is then deprotected and reacted with, for example, a similarly C-terminal protected methionine. These steps are then repeated with alanine, and finally leucine esters, followed by the coupling of doxorubicin to the immobilized succinyl-tripeptide. The molecule is then liberated from the resin by using mildly acidic conditions to form a free prodrug, such as free Suc-Met-Ala-Leu-Dox. This methodology is represented on the scheme of FIG. 9. Another version of phase synthesis utilizes immobilized succinyl oligopeptide ester. This is then C-terminally deprotected, followed by the coupling step to doxorubicin or other therapeutic agent, and finally liberated from the resin as represented on the scheme of FIG. 9. The acid form of the prodrug molecule may then be converted finally into its sodium salt as described above.

General Large Scale Compound Synthesis

The prodrug compound can be synthesized using a simple and efficient three-step process of the invention: (1) coupling an alkyl or allyl ester protected stabilizing group-oligopeptide and a therapeutic agent in the presence of an activating agent to make an alkyl or allyl ester protected stabilizing group-oligopeptide-therapeutic agent conjugate, (2) removing uncoupled therapeutic agent that remains after the coupling step, and (3) deprotecting the alkyl or allyl ester protected stabilizing group-oligopeptide-therapeutic agent conjugate to make the stabilizing group-oligopeptide-therapeutic agent prodrug compound.

The first step involves the coupling of an alkyl-ester protected oligopeptide fragment to a therapeutic agent. A preferred embodiment of the first step involves the coupling of an alkyl or allyl ester protected stabilizing group oligopeptide, such as MeOSuc-Leu-Ala-Leu-OH, with a therapeutic agent, such as doxorubicin, using an activating agent, such as HATU, to give an alkyl or allyl ester protected stabilizing group oligopeptide therapeutic agent conjugate, e.g., MeOSuc-Leu-Ala-Leu-Dox. The focus of this step is on the purity and the yield of the methyl ester, since it was found that the hydrolysis step does not have a significant impact on purity. Preferably the molar ratio of the alkyl or allyl ester protected stabilizing group oligopeptide to the therapeutic agent will be between 2:1 and 1:1. More preferably the molar ratio is between 1.75:1 and 1.5:1. Most preferably the molar ratio is 1.66:1.

The coupling of the alkyl or allyl ester protected stabilizing group oligopeptide and a therapeutic agent is preferably performed by: (a) combining the alkyl or allyl ester protected stabilizing group oligopeptide and the therapeutic agent in DMF, (b) adding DIEA, (c) reacting the alkyl or allyl ester protected stabilizing group oligopeptide and the therapeutic agent in the presence of the activating agent to form the conjugate, and (d) precipitating the conjugate by adding a brine solution to form a precipitate. Preferably the molar ratio of the DIEA and the alkyl or allyl ester protected stabilizing group-oligopeptide is between 3:1 and 1.5:1. More preferably the molar ratio is 2.5:1 and 2:1. Most preferably the molar ratio is 2.18:1. The reacting step is preferably performed at 0° C., for 30 minutes. Preferably the molar ratio of the activating agent and the alkyl or allyl ester protected stabilizing group-oligopeptide is between 1.5:1 and 1:1. More preferably, the molar ratio is 1.1:1. The brine solution is preferably between 20% (w/v) and 40% (w/v) of NaCl in water. More preferably the brine solution is preferably between 25% (w/v) and 35% (w/v) of NaCl in water. Most preferably the brine solution is 30% (w/v) of NaCl in water. The conjugate is preferably precipitated in a brine solution, wherein the pH is between 5.0 and 7.0, inclusive. Most preferably, the conjugate is precipitated at a pH between 5.8 and 6.0.

Since many therapeutic agents are toxic substances, it is preferable to eliminate any free therapeutic agent from the coupled product. The removing step is preferably performed by: (a) dissolving the conjugate in DMF, (b) dissolving a scavenger resin in anhydrous DMF, (c) adding the alkyl or allyl ester protected stabilizing group oligopeptide therapeutic agent conjugate formed in the coupling step to the scavenger resin to form a conjugate-resin mixture, (d) maintaining the mixture at between 0° C. and 30° C. for 2 to 24 hours wherein the uncoupled therapeutic agent reacts with the resin, (e) removing the resin from the mixture, and (f) precipitating the remainder by adding a brine solution to form a precipitate of the alkyl or allyl ester protected stabilizing group oligopeptide therapeutic agent conjugate. Preferably the scavenger resin is polystyrene-isocyanate (PS-isocyanate), PS-methylisocyanate, PS-thioisocyanate, PS-methylthioisocyanate, PS-sulfonyl chloride, PS-methylsulfonyl chloride or PS-benzaldehyde. Most preferably, the scavenger resin is PS-isocyanate. The removing step is preferably performed to remove free therapeutic agent, which is an anthracycline.

The third step is deprotecting the alkyl or allyl ester protected stabilizing group-oligopeptide-therapeutic agent conjugate, preferably via hydrolysis by an enzyme, more preferably via hydrolysis by an esterase, which directly gives the prodrug compound in good yield with a final purity of at least 90%. For example, the third step may be the hydrolysis of the methyl ester group in MeOSuc-Leu-Ala-Leu-Dox by an enzyme, such as CLEC CAB (crosslinked Candida Antartica B Lipase), which directly gives the sodium salt of Suc-Leu-Ala-Leu-Dox in quantitative yields with high purity.

The enzyme is preferably either crosslinked or immobilized on a solid support. The esterase may be pig liver esterase, Candida Antartica B Lipase, Candida Rugosa lipase, Pseudomonas Cepacia lipase, pig liver esterase immobilized on sepharose, Candida antartica B lipase immobilized on sepharose, CLEC-PCTM (Pseudomonas Cepacia lipase), CLEC-CAB (Candida Antartica B lipase), or CLEC-CR (Candida Rugosa lipase). Deprotecting via hydrolysis by an enzyme is preferably performed by: (a) washing the enzyme to remove free enzyme, (b) adding the washed enzyme to the alkyl or allyl ester protected stabilizing group-oligopeptide-therapeutic agent conjugate, (c) reacting the enzyme with the conjugate at between 15° C. and 40° C., inclusive, at a pH between 5.0 and 8.0, inclusive, for at least 18 hours, to create the stabilizing group-oligopeptide-therapeutic agent prodrug compound, and (d) separating the enzyme from the prodrug compound. Most preferably additional washed crosslinked or immobilized enzyme is added after the step of reacting the enzyme with the conjugate, prior to separating the enzyme from the prodrug compound.

Removal of Free Therapeutic Agent

Figure 17:
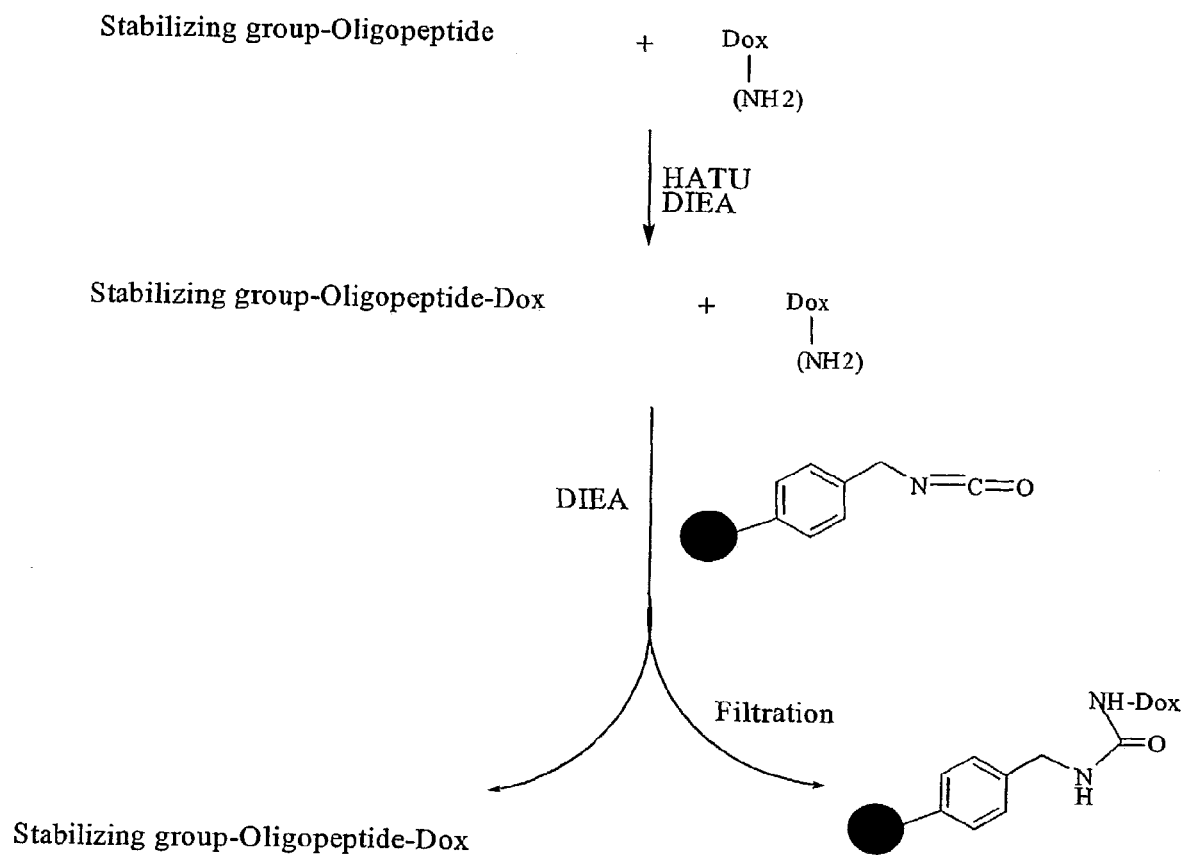
FIG. 17 illustrates the removal of free therapeutic agent through the use of scavenging resin or beads.

Unconjugated therapeutic agent may be present late in the process of making the prodrug. For example, during the coupling step of (stabilizing group)-(oligopeptide) conjugate with doxorubicin as the therapeutic agent, it was found, in some instances, that the reaction did not proceed completely. There was about 2–4% of residual doxorubicin remaining in the coupled product. Initial attempts to remove doxorubicin completely from the product by acidic washes did not result in complete removal. The complete removal of the free therapeutic agent was effected by the process outlined in Example 29 and FIG. 17 that utilizes scavenging resin or beads.

The crude product, which contains the intermediate and residual doxorubicin, were dissolved in DMF and polystyrene methylisocyanate or polystyrene sulfonyl chloride resin or beads were added. The reaction was stirred for 60 minutes. The free amino group of doxorubicin reacts with the isocyanate or sulfonyl chloride group on the beads to form a urea or sulfonamide derivative. The solid beads with doxorubicin attached to them were then separated from the desired product by filtration. The desired product remains in the DMF solution. This approach seems to be a very mild and effective method for removing residual therapeutic agent from the product.

Thus, the invention includes a method of making a compound comprising:

(1) selecting an Fmoc-protected oligopeptide of the formula Fmoc-$AA^3$-$AA^2$-$AA^1$ wherein each AA independently represents an amino acid, (2) coupling the Fmoc-protected oligopeptide to a therapeutic agent by activating the Fmoc-protected oligopeptide with an activating agent in the presence of the therapeutic agent to form an Fmoc-protected oligopeptide-therapeutic agent conjugate, (3) deprotecting the Fmoc-protected oligopeptide-therapeutic agent conjugate by contacting it with a base to form an oligopeptide-therapeutic agent conjugate, and
(4) coupling the oligopeptide-therapeutic agent conjugate to a stabilizing group to form the compound.

Alternatively, a method of making a compound comprises the following steps:
(1) selecting all oligopeptide of the formula $AA^3$-$AA^2$-$AA^1$ wherein each AA independently represents an amino acid,
(2) coupling the oligopeptide to an alkyl ester-protected stabilizing group to form an alkyl ester-protected stabilizing group-oligopeptide conjugate,
(3) coupling the alkyl ester-protected-stabilizing group-oligopeptide conjugate to a therapeutic agent by activating the alkyl ester-protected stabilizing group-oligopeptide conjugate with an activating agent in the presence of a therapeutic agent to form an alkyl ester-protected stabilizing group-oligopeptide-therapeutic agent conjugate, and
(4) deprotecting the alkyl ester-protected stabilizing group-oligopeptide therapeutic agent conjugate to form the compound.

A compound of the invention may also be made via the following steps:
(1) selecting an oligopeptide of the formula $AA^3$-$AA^2$-$AA^1$ wherein each AA independently represents an amino acid,
(2) coupling the oligopeptide to an allyl ester-protected stabilizing group to form an allyl ester-protected stabilizing group-oligopeptide conjugate,
(3) coupling the allyl ester-protected-stabilizing group-oligopeptide conjugate to a therapeutic agent by activating the allyl ester-protected stabilizing group-oligopeptide conjugate with an activating agent in the presence of a therapeutic agent to form an allyl ester-protected stabilizing group-oligopeptide-therapeutic agent conjugate, and
(4) deprotecting the allyl ester-protected stabilizing group-oligopeptide therapeutic agent conjugate to form the compound.

Yet another method for making a compound of the invention comprises the following steps:
(1) selecting a trityl-protected oligopeptide of the formula trityl-$AA^3$-$AA^2$-$AA^1$ wherein each AA independently represents an amino acid,
(2) coupling the trityl-protected oligopeptide to a therapeutic agent by activating the trityl-protected oligopeptide with an activating agent in the presence of a therapeutic agent, thereby making a trityl-protected oligopeptide-therapeutic agent conjugate,
(3) deprotecting the trityl-protected oligopeptide-therapeutic agent conjugate under acidic conditions to form an oligopeptide-therapeutic agent conjugate, and
(4) coupling the oligopeptide-therapeutic agent conjugate with an stabilizing group to form the compound.

Another possible step in connection with any of these methods is removing uncoupled therapeutic agent by use of scavenging resin or beads. Further, the compound may be neutralized with a pharmaceutically acceptable salt if desired.

Specific Compounds

Compounds of the invention include the prodrugs, Suc-Met-Ala-Leu-Dox, Gl-Met-Ala-Leu-Dox, Suc-Phe-Gly-Phe-Dnr, Suc-Phe-Gly-Leu-Dnr, Suc-Phe-Gly-Ile-Dnr, Suc-Leu-Ala-Gly-Dox, Pyg-Leu-Ala-Leu-Dnr, Suc-Leu-Ala-Leu-Dox, Suc-Leu-Thr-Leu-Dnr, Suc-Leu-Tyr-Leu-Dnr, Suc-Leu-Tyr-Leu-Dox, Suc-Met-Ala-Leu-Dnr, Suc-Met-Gly-Phe-Dnr, Suc-Met-Gly-Ile-Dnr, Suc-Met-Gly-Leu-Dnr, Suc-Tyr-Ala-Ile-Dnr, or Suc-Nle-Ala-Leu-Dnr.

Additionally, the following intermediate compounds, important to the process of preparation of the prodrugs of the invention, are part of the invention:
Trityl-Met-Ala-Leu-Dox
Diphenyhnethyl-Met-Ala-Leu-Dox
Benzyloxycarbonyl-Met-Ala-Leu-Dox
Fmoc-Leu-Met-Leu-OBn
Met-Ala-Leu-OBn
Methyl-succinyl-Met-Ala-Leu-OBn
Methyl-succinyl-Met-Ala-Leu
Fmoc-Met-Ala-Leu
Fmoc-Met-Ala-Leu-Dnr
Gl-Met-Ala-Leu-Dox
Met-Ala-Leu-Dox Lactate
Allyl-succinyl-Met-Ala-Leu-Dox
Suc-Met-Ala-Leu
Methyl esters of Suc-Met-Ala-Leu
Fmoc-Met-Ala-Leu-Dox
Methyl-succinyl-Met-Ala-Leu-Dox, and
Allyl-hemi succinate.

EXAMPLES

Example 1

Screening of Potential Prodrugs with Trouase and Human Blood

A good candidate for a prodrug with improved therapeutic index is activated by cancer cells but relatively stable in whole human blood. Three different preparations of carcinoma were used to screen various test compounds. These three preparations were as follows:
(a) MCF 7/6 (breast carcinoma) cell homogenate
(b) MCF 7/6 (breast carcinoma) conditioned media, and
(c) HeLa (cervical carcinoma) cell extract anion exchange fraction pool.

Compounds which could be hydrolyzed to a single and/or di-amino acid toxin conjugate (i.e., $AA^1$-therapeutic agent and/or $AA^2$-$AA^1$-therapeutic agent) were further tested for stability in whole human blood. The whole blood was collected using commercial acid buffered citrate whole blood collection tubes (Becton Dickinson).

(a) Preparation of MCF 7/6 Cell Homogenate

MCF 7/6 cells were grown to confluence in a serum free medium containing DMEM:F12 (1:1), 50 mg/L bovine serum albumin, ITS-X (10 mg/L insulin, 5.5 mg/L transferrin, 6.7 μg/L Na selenite, 2 mg/L ethanolamine), and Lipid Concentrate (Gibco #21900-030). 100 mL of cells were harvested by centrifugation at 4° C. 10,000×g, for 20 min and decanting the supernatant. The pellet was resuspended in 2 mL phosphate buffered saline (Gibco) and centrifuged at 18,000×g for 10 min. After decanting the supernatant, the cells (approximately 300 μL wet) were homogenized by grinding in 1.7 mL 10 mM pH 7.2 HEPES buffer (sodium salt). The homogenate was centrifuged at 18,000×g at 4° C. for 5 min and the supernatant was aliquoted and stored at ≦−20° C. for subsequent use in the compound screen.

(b) Preparation of MCF 7/6 Conditioned Media

MCF 7/6 cells were grown to confluence in DMEM/F12 (1:1) medium containing 10% fetal bovine serum, 0.05% (w/v) L-glutamine, 250 IU/mL penicillin, and 100 μg/mL streptomycin. Cells were then washed twice with phosphate buffered saline and incubated 24 hr at 5% $CO_2$, 37° C., in DMEM/F12 (1:1), 0.02% BSA, ITS-X (10 mg/L insulin, 5.5 mg/L transferrin, 6.7 µg/L Na selenite, 2 mg/L ethanolamine). The conditioned media was then decanted and, using a stirred cell apparatus with a YM10 (10,000 MW cutoff) ultrafiltration membrane(Millipore), exchanged once with 10 mM HEPES buffer, pH 7.2 and concentrated twenty-fold. This solution was stored in aliquots at −20° C. for use in the compound screen.

(c) Preparation of HeLa Cell Anion Exchange Fraction Pool

Thirty billion commercially produced HeLa Cells (human cervical carcinoma, *Computer Cell Culture Ceizter*, Seneffe, Belgium) were homogenized with a sonicator and with a Dounce homogenizer in 108 mL of aqueous lysis solution. The lysis solution contained 0.02% w/v Triton X-100, 0.04% w/v sodium azide, and a cocktail of protease inhibitors (2 tablets/50 mL Complete™, EDTA-free tablets, Roche Molecular Biochemicals). The cell homogenate was centrifuged 30 minutes at 4° C. at 5000×g and the pellet was homogenized in a second 108 mL of lysis solution using a Dounce homogenizer and centrifuged as before. The supernatants were combined and centrifuged for 90 min at 145,000×g at 4° C.

A portion of the ultracentrifugation supernatant was diluted 2-fold with a 20 mM triethanolamine-HCl pH 7.2 buffer containing 0.01% (w/v) Triton X-100 and 0.02% (w/v) sodium azide (equilibration buffer). Thirty mL of the resulting solution, corresponding to approximately 180 mg of protein, was loaded at 4° C. on a 2.6×9.4 cm Source™ 15Q (Amersham Pharmacia Biotech) low pressure anion exchange chromatography column (1 ml/minute). The column was then washed with 250 ml of the equilibration buffer at a flow rate of 1 mL/minute. Proteins were eluted in a NaCl linear concentration gradient (0–0.5 M in the equilibration buffer, total volume of the gradient was 1000 ml) at a flow rate of 3 ml/minute. Two-minute fractions were collected and used for enzyme activity determination using βAla-Leu-Ala-Leu-Dox as the substrate. Its transformation into Ala-Leu-Dox was quantified by reverse phase high performance liquid chromatography utilizing fluorescence detection of the anthracycline moiety. The fractions containing the highest activity levels were pooled (fractions #43–46; ~0.13 M NaCl), supplemented with protease inhibitors (Complete™, EDTA-free tablets, Roche Molecular Biochemicals), and stored as aliquots at −80° C.

(d) Cleavage Assay

Test compounds were incubated for 2 hr at 37° C. at a concentration of 12.5 µg/mL, in pH 7.2, 10 mM HEPES, 1 mM CoCl$_2$ or 100 mM MnCl$_2$, with the three different preparations of carcinoma enzyme and with whole human blood collected over sodium citrate. Following incubation, three volumes of acetonitrile were added to stop the reaction and remove protein from the mixture. The sample was centrifuged at 18,000 g for 5 minutes and 100 µL of supernatant was mixed with 300 µL of water prior to analysis by HPLC. For HPLC analysis 50 µL of sample was injected on a 4.6×50 mm 2µ TSK Super-ODS chromatography column at 40° C. and eluted with a 3 minute linear gradient from 26% to 68% acetonitrile in aqueous 20 mM ammonium acetate pH 4.5 buffer at 2 mL/min. Detection was by fluorescence using an excitation wavelength of 235 nm and an emission wavelength of 560 nm.

Test compounds that were cleaved by the trouase under the given conditions and were stable in human blood are shown in Table 2. With few exceptions, results for carcinoma enzyme cleavage were the same for a partially purified fraction from HeLa cells, MFC 7/6 cell homogenate, and MCF 7/6 conditioned media.

TABLE 2

| No: | Stabilizing Group | (AA$_3$) P1 | (AA$_2$) P1' | (AA$_1$) P2' | Therapeutic Compound |
|---|---|---|---|---|---|
| 1 | Suc | Phe | Gly | Phe | Dnr |
| 2 | Suc | Phe | Gly | Leu | Dnr |
| 3 | Suc | Phe | Gly | Ile | Dnr |
| 4 | Suc | Leu | Ala | Gly | Dox |
| 5 | Pyg | Leu | Ala | Leu | Dnr |
| 6 | Suc | Leu | Ala | Leu | Dnr |
| 7 | Suc | Leu | Ala | Leu | Dox |
| 8 | Suc | Leu | Thr | Leu | Dnr |
| 9 | Suc | Leu | Tyr | Leu | Dnr |
| 10 | Suc | Leu | Tyr | Leu | Dox |
| 11 | Suc | Met | Ala | Leu | Dnr |
| 12 | Suc | Met | Ala | Leu | Dox |
| 13 | Suc | Met | Gly | Phe | Dnr |
| 14 | Suc | Met | Gly | Ile | Dnr |
| 15 | Suc | Met | Gly | Leu | Dnr |
| 16 | Suc | Tyr | Ala | Ile | Dnr |
| 17 | Suc | Nle | Ala | Leu | Dnr |

Example 2

Identification Tripeptide Drugs with Favorable Cleavage Rates

Test compounds were incubated for 2 hr at 37° C. at a concentration of 12.5 µg/mL with HeLa cell anion exchange fraction (F1), as prepared in Example 1(c). Following incubation, three volumes of acetonitrile were added to stop the reaction and remove protein from the mixture. The sample was centrifuged at 18,000 g for 5 minutes and 100 µL of supernatant was mixed with 300 µL of water prior to analysis by HPLC. For HPLC analysis 50 µL of sample was injected on a 4.6×50 mm 2µ TSK Super-ODS chromatography column at 40° C. and eluted with a 3 minute linear gradient from 26% to 68% acetonitrile in aqueous 20 mM ammonium acetate pH 4.5 buffer at 2 mL/min. Detection was by fluorescence using an excitation wavelength of 235 nm and an emission wavelength of 560 nm.

the amount of cleavage of each test compound was compared to the amount of a standard Suc-βAla-Leu-Ala-Leu-therapeutic agent conjugate cleaved by F1 under the same conditions. The therapeutic agent in the standard (Dox or Dnr) was the same as in the test compound. Table 3 provides the relative cleavage rates of several tripeptide prodrugs.

TABLE 3

| Tripeptide analog | Relative Cleavage % |
|---|---|
| Suc-Nle-Gly-Phe-Dnr | 17 |
| Suc-Phe-Gly-Phe-Dnr | 12 |
| Suc-Leu-Tyr-Leu-Dox* | 14 |
| Suc-Phe-Gly-Leu-Dnr | 24 |
| Suc-Tyr-Ala-Ile-Dnr | 25 |
| Suc-Met-Gly-Phe-Dnr | 29 |
| Suc-Leu-Ala-Gly-Dox | 40 |
| Suc-Met-Gly-Ile-Dnr | 46 |
| Suc-Met-Ala-Leu-Dox | 49 |
| Suc-Phe-Gly-Ile-Dnr | 54 |
| Suc-Met-Gly-Leu-Dnr | 55 |
| Suc-Leu-Ala-Leu-Dox | 62 |
| Suc-Met-Ala-Leu-Dnr | 69 |
| Pyg-Leu-Ala-Leu-Dnr | 76 |

TABLE 3-continued

| Tripeptide analog | Relative Cleavage % |
|---|---|
| Suc-Leu-Ala-Leu-Dnr | 76 |
| Suc-Tyr-Ala-Len-Dnr | 77 |

*tested with recombinant rat TOP

Example 3

Tumor-Activated Prodrug Activity on LNCaP, HT-29 and PC-3 Cells

Adherent cells, LNCaP (prostate carcinoma), HT-29 (colon carcinoma) and PC-3 (prostate carcinoma), were cultured in DMEM media containing 10% heat inactivated fetal calf serum (FCS). On the day of the study the cells were detached from the plate with a trypsin solution. The collected cells were washed and resuspended at a concentration of $0.25 \times 10^6$ cells/ml in DMEM containing 10% FCS. 100 µl of cell suspension were added to 96 well plates and the plates were incubated for 3 hours to allow the cells to adhere. Following this incubation, serial dilutions (3-fold increments) of doxorubicin or test compounds were made and 100 µl of compounds were added per well. The plates were then incubated for 24 hours, pulsed with 10 µl of a 100 µCi/ml $^3$H-thymidine and incubated for an additional 24 hours (total incubation time 48 hours). The plates were harvested using a 96 well Harvester (Packard Instruments) and counted on a Packard Top Count Counter. Four parameter logistic curves were fitted to the $^3$H-thymidine incorporation as a function of drug molarity using Prism software to determine $IC_{50}$ values.

TABLE 4

Activity on LNCaP, HT-29 and PC-3 cells.

| | IC50 (µM) | | |
|---|---|---|---|
| Compound | LNCAP | HT29 | PC-3 |
| DOX | 0.016 | 0.052 | 0.075 |
| Suc-Leu-Ala-Leu-Dox | 1.0 | 36 | 50 |
| Suc-Ile-Ala-Leu-Dox | 1.1 | 47 | 88 |
| Suc-Leu-NMeAla-Leu-Dox | 1.2 | 24 | 45 |
| Suc-Ile-Pro-Leu-Dox | 2.0 | 44 | 106 |
| Suc-Leu-Tyr-Leu-Dox | 9.4 | 42 | 51 |
| Suc-Leu-Ala-Gly-Dox | 15 | 32 | 39 |
| Suc-Leu-Tyr-Gly-Dox | 15 | 25 | 64 |

Prostate carcinoma cells, LNCaP and PC-3 cells or colon carcinoma cells HT-29, were incubated with increasing concentration of the indicated compounds for 48 hours and cellular proliferation was measured using the $^3$H-thymidine assay. The $IC_{50}$ of the positive control, doxorubicin, was 0.02–0.08 µM in the cell lines used. The data shows that multiple cells lines such as PC-3 and HT29 do not cleave the above-indicated prodrugs/In contrast, an enzyme present in or on LNCAP cells cleaves several of the tripeptide prodrugs. The most potent analogs are exemplified with Suc-Leu-Ala-Leu-Dox and Suc-Ile-Ala-Leu-Dox, which have an $IC_{50}$ of approximately 1 µM on LNCaP cells.

Example 4

Suc-Leu-Ala-Leu-Dox is Better Tolerated in vivo than Doxorubicin

In a single-dose Maximum Tolerated Dose (MTD) study, groups of 5 healthy young female normal mice were given intravenous doses of the Suc-Leu-Ala-Leu-Dox of either 0, 23, 47, 70, 93 and 117 mg/kg, equivalent to 0, 14, 28, 42, 56, and 70 mg/kg of Doxorubicin, respectively. Suc-Leu-Ala-Leu-Dox was very well tolerated, with no mortalities observed over the 28-day study, and only slight body weight loss initially in the higher dose-groups, followed by recovery. Therefore the prodrug made it possible to safely administer an equivalent dose of doxorubicin of 66 mg/kg, which is approximately 8-fold higher than would be possible with doxorubicin alone, which has an MTD of about 4–8 mg/kg. The single-dose MTD of Suc-Leu-Ala-Leu-Dox was not attained in this experiment, and is therefore greater than 117 mg/kg.

However, post-analysis of the compounds showed that they contained about 47% active compound due to water content and impurity. So the doses mentioned in the above paragraph overestimated the amount of compound administered. Recalculation of the data showed that the prodrug made it possible to safely administer an equivalent dose of doxorubicin of 70 mg/kg, which is approximately 3.3-fold higher than would be possible with doxorubicin alone, which has an MTD of about 16 mg/kg The above experiment was repeated and the following results were obtained. The single dose MTD of Suc-Leu-Ala-Leu-Dox was determined to be approximately 59 mg/kg (35 mg/kg doxorubicin equivalent), which is at least 1.2-fold higher than that of doxorubicin alone (16 mg/kg). The more relevant comparison is the repeat-dose (RD) MTD, as a SD is not efficacious. The repeat dose MTD of Suc-Leu-Ala-Leu-Dox was approximately 52 mg/kg, Q7Dx5 (31 mg/kg doxorubicin equivalent, based on efficacy study in Example 12, which was 6.8-fold higher than the repeat dose MTD of doxorubicin (4 mg/kg).

Example 5

Suc-Leu-Ala-Leu-Dox is Better Tolerated In Vivo than Doxorubicin

Suc-Leu-Ala-Leu-Dox, an exemplary tripeptide prodrug of the invention, is well tolerated in mice. In a second single dose Maximum Tolerated Dose (SD-MTD) study, groups of five normal ICR mice were administered intravenous bolus doses of Suc-Leu-Ala-Leu-Dox. The mice were observed daily for 49 days and body weights measured twice weekly. Dose levels tested were 0, 47, 59, 71, 94, 117, 140 or 164 mg/kg, equivalent to 0, 28, 35, 42, 56, 70, 84 or 98 mg/kg of doxorubicin, respectively. There was no acute toxicity, within 24 hours, at any dose level. Dose and time dependent signs of toxicity were observed during the study. Toxicity, including partial hind-end paralysis and significant body weight loss (>20% of their initial weight), was observed in the 94 mg/kg and higher dose groups. Based on survival and lack of signs of toxicity at Day 49, the SD-MTD for Suc-Leu-Ala-Leu-Dox was determined to be 71 mg/kg (equivalent to 42 mg/kg of doxorubicin). Therefore, the SD-MTD was approximately 2.6-fold higher on a molar basis than the SD-MTD for doxorubicin alone (16 mg/kg). See Table 5. This is an approximate SD-MTD determination based on a range of doses at 7 or 14 mg/kg doxorubicin equivalents increments over the range tested.

TABLE 5

| Compound Name | SD-MTD (mg/kg) | SD-MTD (mg/kg Dox =) | SD-MTD Molar Ratio (Dox =) |
|---|---|---|---|
| Doxorubicin | 16 | 16 | 1 |
| Suc-Leu-Ala-Leu-Dox | 71 | 42 | 2.6 |

Example 6

Suc-Len-Ala-Gly-Dox is Better Tolerated In Vivo than Doxorubicin

In a second single dose Maximum Tolerated Dose (SD-MTD) study, groups of five normal ICR mice were administered intravenous bolus doses of Suc-Leu-Ala-Gly-Dox. The mice were observed daily for 49 days and body weights measured twice weekly. Dose levels tested were 0, 88, 110, 132, 154, 176, 198 or 220 mg/kg, equivalent to 0, 56, 70, 84, 98, 112, 126 or 141 mg/kg of doxorubicin, respectively. There was no acute toxicity, within 24 hours, at any dose level. Suc-Leu-Ala-Gly-Dox was very well tolerated, with no mortalities, morbidity or significant body weight loss observed over the 49 day study at any dose level. Thus, the SD-MTD of Suc-Leu-Ala-Gly-Dox was not attained in this study, and is therefore at least the highest dose tested. Based on survival and lack of signs of toxicity at Day 49, the SD-MTD for Suc-Leu-Ala-Gly-Dox was at least 220 mg/kg (equivalent to 141 mg/kg of doxorubicin), which is 8.8-fold higher on a molar basis than the SD-MTD for doxorubicin alone (16 mg/kg). See Table 6.

TABLE 6

| Compound Name | SD-MTD (mg/kg) | SD-MTD (mg/kg Dox =) | SD-MTD Molar Ratio (Dox =) |
|---|---|---|---|
| Doxorubicin | 16 | 16 | 1 |
| Suc-Leu-Ala-Gly-Dox | >220 | >141 | 8.8 |

Example 7

Suc-Met-Ala-Leu-Dox is Better Tolerated In Vivo than Doxorubicin

In a single dose Maximum Tolerated Dose (MTD) study, groups of 5 healthy young female normal mice were given intravenous doses of the Suc-Met-Ala-Leu-Dox of either 24, 48, 71, 96 and 120 mg/kg, equivalent to 14, 28, 42, 56, and 70 mg/kg of doxorubicin, respectively. Although no acute signs of toxicity were observed following administration of Suc-Met-Ala-Leu-Dox, several animals in the two highest dose groups underwent significant weight loss and morbidity at around 25 days post administration. The group mean body weights of lower dose groups were not significantly different from the vehicle-treated control group. The symptoms of toxicity (paralysis and morbidity) were typical of doxorubicin. The 28-Day survival single-dose MTD value was established at approximately 71 mg/kg (equivalent to about 40 mg/kg doxorubicin). The single dose MTD of Suc-Met-Ala-Leu-Dox provides a dose of doxorubicin about 1.5-fold higher than would be possible with doxorubicin alone.

Example 8

Suc-Leu-Ala-Leu-Dox and its Metabolites are Rapidly Cleared

The metabolism and clearance of the prodrug compounds was studied in healthy young female mice, administered a single intravenous dose at 117 mg/kg Suc-Leu-Ala-Leu-Dox Plasma samples were obtained at 1 and 4 hours. Plasma samples of 100 μl were transferred to microcentrifuge tubes (1.5 mL) and an internal standard of daunorubicin (20 μL at 0.5 mg/ml) was added together with acetonitrile (400 μl). The tubes were capped and briefly vortexed followed by centrifugation at 14,000 rpm. 420 μl from each tube was removed and dried in vacuo. Each sample was reconstituted in 65 μl 20 mM aqueous ammonium formate (AF) pH 4.5 buffer containing acetonitrile (20%) prior to analysis by reverse phase liquid chromatography in combination with tandem mass spectrometry (LC MS/MS).

Urine was collected at 2 and 24 hours post administration from pairs of mice in metabolic cages. Urine samples were diluted with AF buffer containing acetonitrile (20%) to give a target analyte concentration within the practical range of the LC MS/MS assay. 30 μl of each diluted sample was placed in a micro centrifuge tube (1.5 ml) and an internal standard of daunorubicin (20 μL at 0.5 mg/ml) was added together with 50 μl of AF buffer containing acetonitrile (20%). Each sample was then analyzed by LC MS/MS.

An Agilent HP1100 HPLC with DAD detector and Chemstation software was coupled to a PE Sciex API 365 mass spectrometer with an electrospray ion source. HPLC was performed on a TSK-Gel Super ODS, 2 mm, 4.6×50 mm (TosoHaas) reversed phase column equipped with a HAI-GUARD C18 guard disc (Higgins Analytical) and stainless steel frit (Upchurch Scientific). Chromatography was performed at room temperature. The flow rate was 0.5 ml/min. Injection volume was 50 μl. Gradient elution was performed using a mobile phase of AF buffer with increasing amounts of acetonitrile. The API 365 was operated at 365° C. in a multiple reaction monitoring mode, set to monitor specific analyte parent-daughter ion pairs. Integration of chromatograms was performed by MacQuan software (PE Sciex) and quantitation of each analyte obtained by comparison to previously obtained calibration curves. Daunorubicin was used as an internal standard in all cases.

Figure 10:
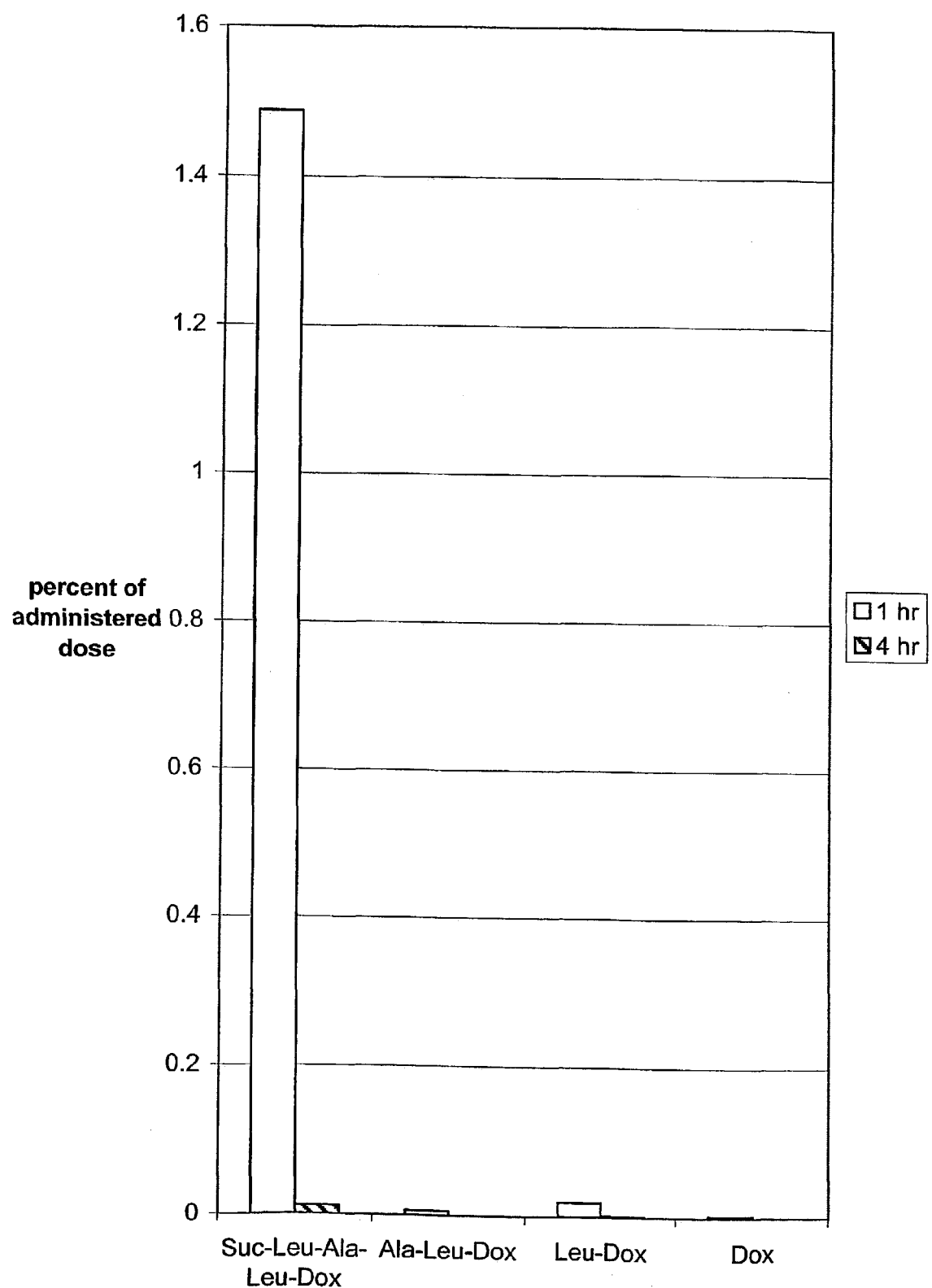
FIG. 10 is a graph of the plasma levels of Suc-Leu-Ala-Leu-Dox and its metabolites at 1 and 4 hours after administration of a single intravenous bolus dose of the prodrug.
Figure 11:
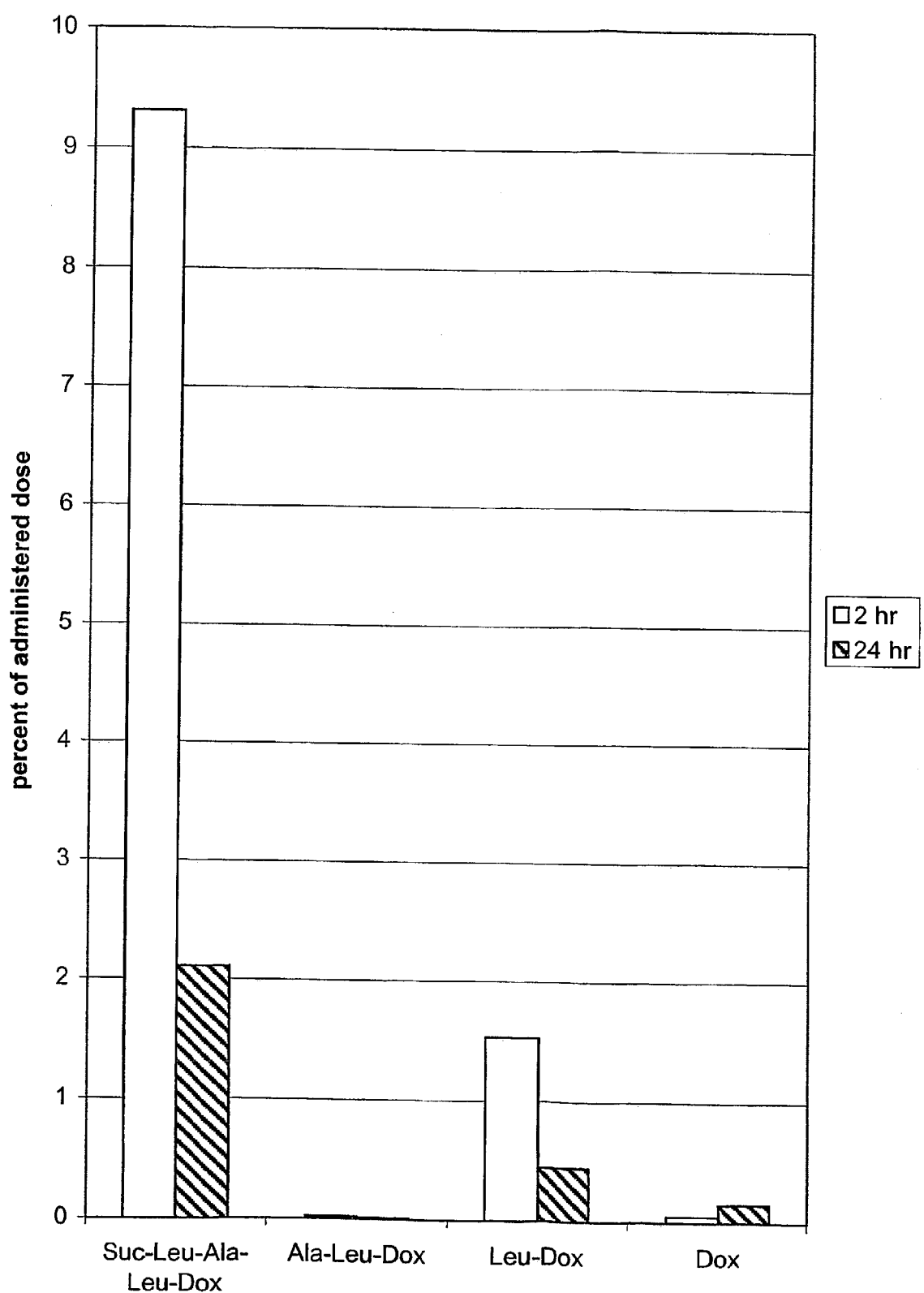
FIG. 11 is a graph of the amount of Suc-Leu-Ala-Leu-Dox and its metabolites present in the urine collected 0–2 and 2–24 hours after the administration of a single intravenous bolus of the prodrug.

The parent compound Suc-Leu-Ala-Leu-Dox was cleared from the circulation very rapidly. After administration, 1.49%, (1 hour) and less than 0.01% (4 hours) of the administered dose could be detected in the plasma (FIG. 10). At 2 and 24 hours, the urine contained 9.31 and 2.11% of the administered dose, respectively (FIG. 11). Low levels of the major peptide metabolites, Ala-Leu-Dox and Leu-Dox, as well as Dox could be detected in plasma. Leu-Dox in particular could be detected in the urine and, as with the other metabolites, was higher at both 2 hours and 24 hours than in plasma at 1 hour or 4 hours. Little free doxorubicin was present in blood or urine at any time point.

TABLE 7

| | Plasma* | | Urine* | |
|---|---|---|---|---|
| | 1 hr | 4 hr | 2 hr | 24 hr |
| Suc-Leu-Ala-Leu-Dox | 1.49 | 0.011 | 9.31 | 2.11 |
| Ala-Leu-Dox | 0.006 | 0.000 | 0.02 | 0.01 |

TABLE 7-continued

|  | Plasma* | | Urine* | |
| --- | --- | --- | --- | --- |
|  | 1 hr | 4 hr | 2 hr | 24 hr |
| Leu-Dox | 0.019 | 0.001 | 1.53 | 0.45 |
| Dox | 0.002 | 0.000 | 0.05 | 0.15 |

*Percent of administered dose

The levels of the prodrug and its metabolites detected in the urine show that the kidney is a major organ of excretion. In contrast, doxorubicin is known to be cleared principally through the hepato-biliary system. The clearance and metabolism profiles of Suc-Leu-Ala-Leu-Dox suggest that there is a very small amount of cleavage and activation of the prodrug in the circulation, or tissues of normal mice. The prodrug and metabolites appear rapidly in the urine, with Leu-Dox being the major metabolite species detected in urine, as well as plasma. In normal animals, clearance of the inactive Suc-Leu-Ala-Leu-Dox and metabolite forms appears to predominate over cleavage to the toxic doxorubicin. The clearance/metabolism results are consistent with the good safety profile observed in the toxicity studies, probably because in normal mice the prodrug, and low levels of metabolites formed, are rapidly cleared from the circulation and excreted via the urine. Thus very little of the prodrug remains available in the circulation to release free doxorubicin, which would be toxic to normal tissues.

Example 9

Suc-Met-Ala-Leu-Dox and its Metabolites are Rapidly Cleared

The metabolism and clearance of the prodrug compounds was studied in healthy young female mice, administered a single intravenous dose at 120 mg/kg Suc-Met-Ala-Leu-Dox. Plasma samples were obtained at 1 or 4 hours, and urine was collected at 2 and 24 hours post administration. Levels of the prodrug and metabolites were measured by LC-MS with UV detection of doxorubicin.

Figure 12:
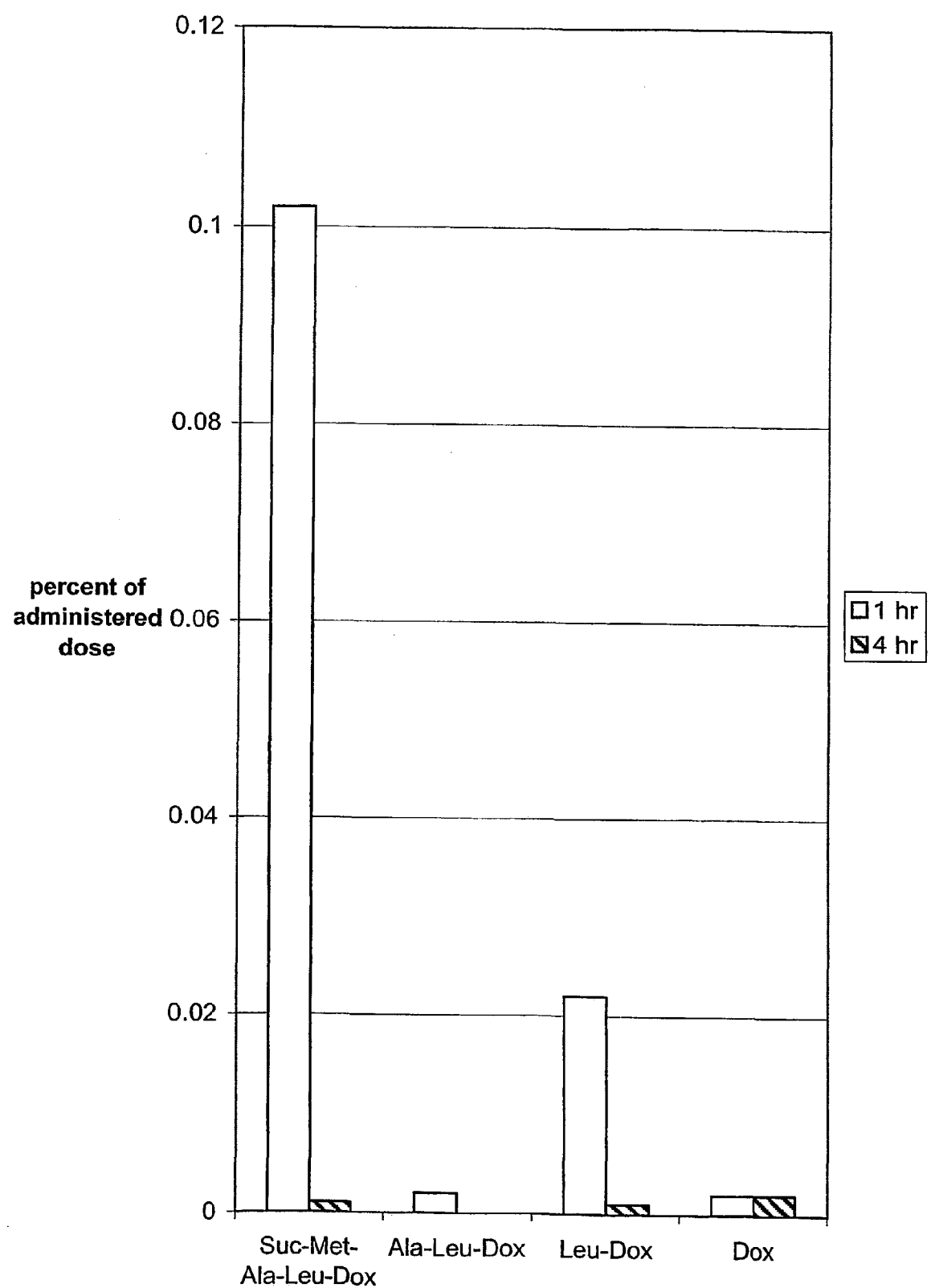
FIG. 12 is a graph of the plasma levels of Suc-Met-Ala-Leu-Dox and its metabolites at 1 and 4 hours after administration of a single intravenous bolus dose of the prodrug.
Figure 13:
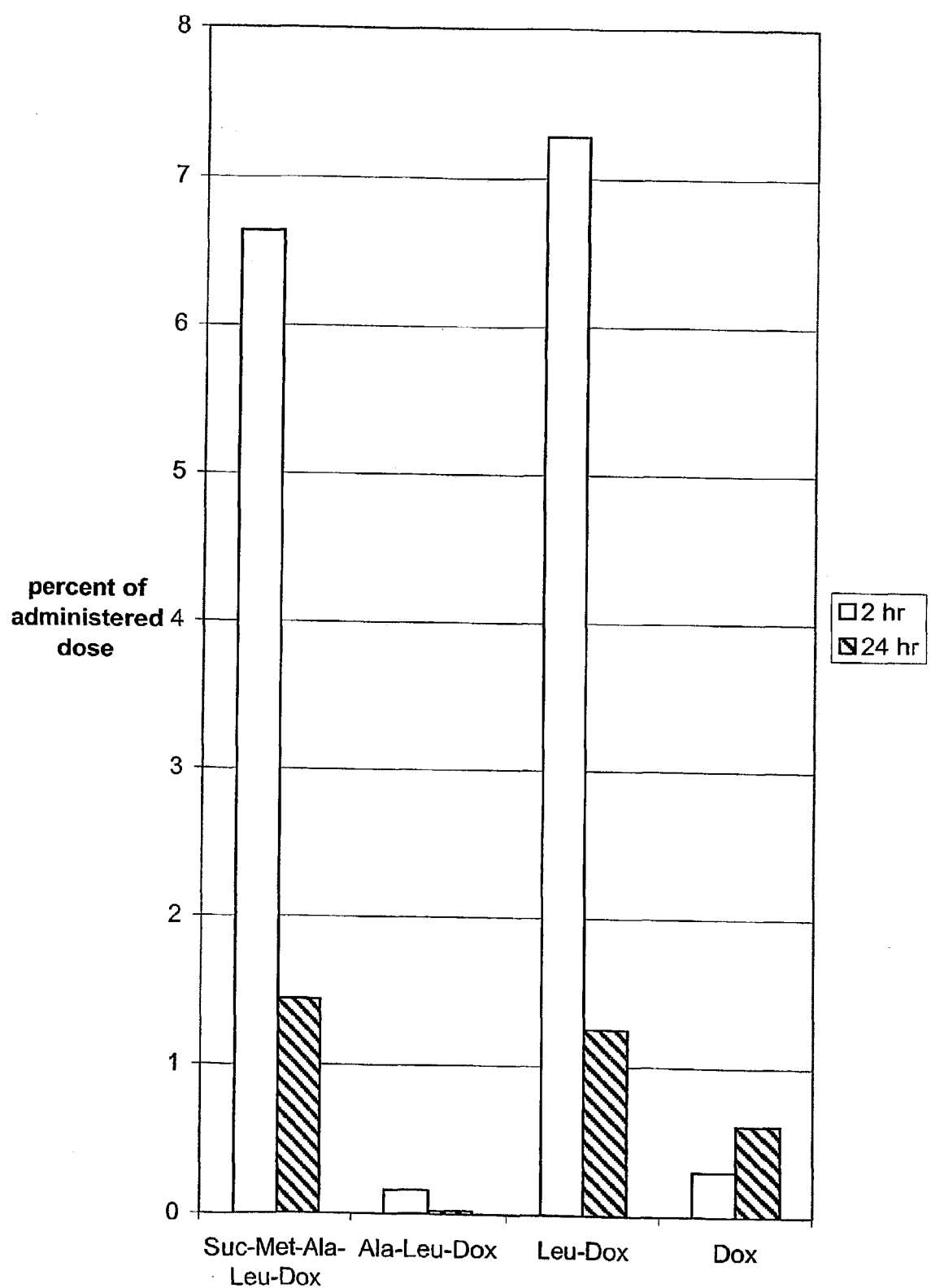
FIG. 13 is a graph of the amount of Suc-Met-Ala-Leu-Dox and its metabolites present in the urine collected 0–2 and 2–24 hours after the administration of a single intravenous bolus of the prodrug.

Suc-Met-Ala-Leu-Dox was detected in plasma at very low levels, with only about 0.1% and 0.001% of the administered dose detected at 1 and 4 hours respectively (FIG. 12). At 2 and 24 hours the urine contained 6.6% and 1.4% of the administered dose of prodrug (FIG. 13). Low levels of the major peptide metabolites, Ala-Leu-Dox and Leu-Dox, as well as Dox could be detected in plasma. In plasma, Leu-Dox levels were about 10 times higher than Ala-Leu-Dox at both 1 and 4 hours and accumulated significantly in the urine by 2 hours. These results suggest that there was significant cleavage of the methionine-containing prodrug. Little free doxorubicin was present in plasma, while urine levels were higher at 2 and 24 hours, suggesting that the rapid disappearance of the prodrug from the plasma may be due in part to cleavage to the active metabolite, doxorubicin.

TABLE 8

|  | Plasma | | Urine | |
| --- | --- | --- | --- | --- |
|  | 1 hr | 4 hr | 2 hr | 24 hr |
| Suc-Met-Ala-Leu-Dox | 0.102 | 0.001 | 6.64 | 1.44 |
| Ala-Leu-Dox | 0.002 | 0.000 | 0.16 | 0.02 |

TABLE 8-continued

|  | Plasma | | Urine | |
| --- | --- | --- | --- | --- |
|  | 1 hr | 4 hr | 2 hr | 24 hr |
| Leu-Dox | 0.022 | 0.001 | 7.28 | 1.25 |
| Dox | 0.002 | 0.002 | 0.30 | 0.61 |

Percent of administered dose

The levels of the prodrug and its metabolites detected in the urine show that the kidney is a major organ of excretion. In contrast, doxorubicin is known to be cleared principally through the hepato-biliary system. The clearance and metabolism studies with Suc-Met-Ala-Leu-Dox suggest that there was considerable systemic or tissue cleavage and activation of the prodrug in normal mice possibly in kidney based on the high urine metabolite values, relative to plasma. Because Leu-Dox is known to be taken up by cells, and cleaved to the active toxic compound doxorubicin, the significant levels of Leu-Dox and doxorubicin are consistent with the less well tolerated safety profile of Suc-Met-Ala-Leu-Dox. The steady levels of doxorubicin in plasma and urine in normal mice are also consistent with slow kinetics of this compound.

Example 10

Comparative Metabolism in Mice

Four groups of ICR normal female mice were administered a single IV bolus dose with approximately 100 μmol/Kg of Suc-βAla-Leu-Ala-Leu-Dox and compared to Suc-Leu-Ala-Leu-Dox, Suc-Leu-Ala-Gly-Dox or 10 μl mol/Kg of doxorubicin (Dox). Plasma was obtained from three individual animals in each group at 5 minutes, 1, 2, 4, or 6 hr. Parent, dipeptidyl-doxorubicin (AL-Dox, AG-Dox), α-aminoacyl-doxorubicin (L-Dox or G-Dox) and doxorubicin concentrations were analyzed in extracts of the plasma samples using a reverse phase gradient HPLC method with fluorescence detection ($\lambda$ex=480 nm, $\lambda$em=560). Peak retention time if G-Dox was not confirmed because a standard was not available. Quantities were determined using a linear standard curve fit to measurements of 10 to 2000 ng/mL doxorubicin solutions in mouse plasma.

Concentration time courses indicate that metabolic patterns were similar for all compounds with the exception of Suc-Leu-Ala-Gly-Dox. In particular, except for Suc-Leu-Ala-Gly-Dox, L-Dox was the major metabolite over the first two hr while the dipeptidyl-conjugate AL-Dox was a more minor product that formed at about the same time as L-Dox. Doxorubicin appeared later with the plasma concentration decreasing more slowly over time than the other metabolites as expected from the current and previously measured doxorubicin pharmacokinetic profiles (Tabrizi-Fard et al., "Evaluation of the Pharmacokinetic Properties of a Doxorubicin Prodrug in Female ICR (CD1® Mice following intravenous administration," *Proc American Association for Cancer Research,* 42: 324 (2001)) and by the doxorubicin control group. The observed cleavage pattern is initial activation of the tripeptide prodrug by an endopeptidase acting between P2-P1, or between the P1 and P1' amino acids. Doxorubicin increases after exopeptidase cleavage of unprotected peptide-doxorubicin metabolic intermediates of the prodrug. Areas under the plasma concentration time curves indicate dosing with Suc-Leu-Ala-Gly-Dox the only peptidyl-conjugate not predicted to be cleaved by CD10, resulted in considerably (ten times) less systemic doxorubicin exposure in normal animals than the two CD10 cleavable tripeptidyl-doxorubicin compounds, or Suc-βAla-Leu-Ala-Leu-Dox. The TOP cleavable tripeptide (Suc-Leu-Ala-Leu-Dox) produced about half the doxorubicin exposure (AUC) as compared to that observed with equimolar doses of the tetrapeptide (Suc-βAla-Leu-Ala-Leu-Dox). It should be noted that relative Doxorubicin exposure after dosing these compounds TABLE 9 is consistent with the relative safety expressed as maximum tolerated dose in a mouse safety study, wherein Suc-Leu-Ala-Gly-Dox was significantly less toxic, when tested up to 3× the molar equivalent dose. Suc-Leu-Ala-Leu-Dox was better tolerated than Suc-βAla-Leu-Ala-Leu-Dox and doxorubicin. Thus, the tripeptide prodrugs significantly protect mice from systemic exposure to doxorubicin after plasma cleavage following administration of 10 times higher molar equivalent doses. The tripeptides, especially Suc-Leu-Ala-Gly, resulted in lower systemic exposures. Thus, the tripeptide, especially Suc-Leu-Ala-Gly, conveys more protection from unwanted systemic toxicities.

TABLE 9

| Dosed Compound | Parent (µM · hr) | AL-Dox or AG-DOX (µM · hr) | L-Dox or G-Dox (µM · hr) | Dox (µM · hr) |
|---|---|---|---|---|
| Suc-βAla-Leu-Ala-Leu-Dox | 806 | 3.2 | 40 | 3.4 |
| Suc-βAla-Ile-Ala-Leu-Dox | 326 | 0.5 | 8.5 | 1.5 |
| Suc-Leu-Ala-Leu-Dox | 634 | 1.6 | 5.1 | 1.6 |
| Suc-Ile-Ala-Leu-Dox | 452 | 1.0 | 6.2 | 0.9 |
| Suc-Leu-Ala-Gly-Dox | 310 | 2.1 | 0.9 | 0.3 |
| Doxorubicin (Dox) | N/A | N/A | N/A | 3.3 |

Example 11

Suc-Leu-Ala-Leu-Dox is Well Tolerated in Tumor Bearing Mice

Figure 14:
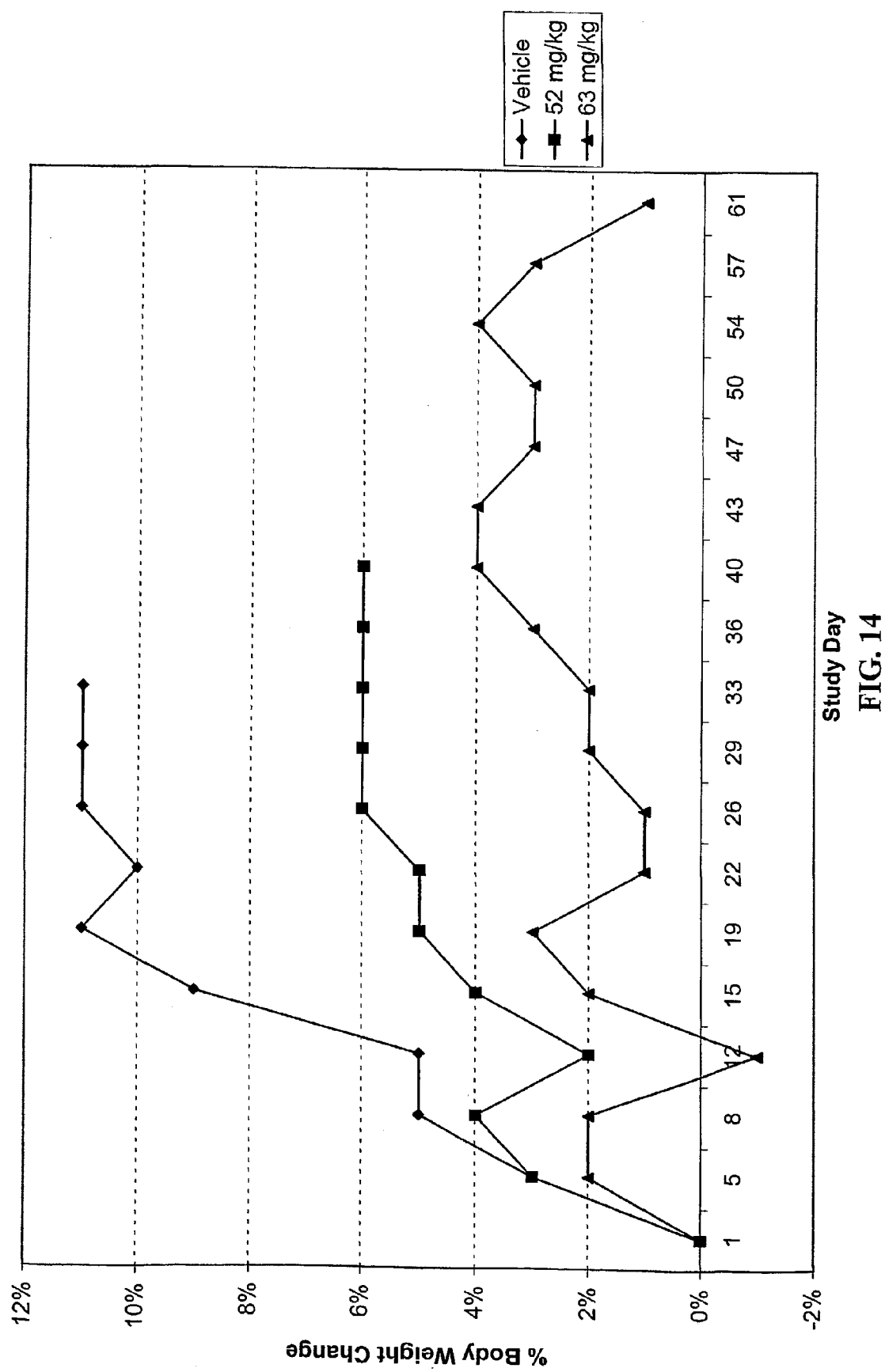
FIG. 14 is a graph of the Percent Body Weight Change of either mice treated with Suc-Leu-Ala-Leu-Dox or mice receiving the vehicle control.

The Suc-Leu-Ala-Leu-Dox prodrug was also safe under repeat-dose conditions, when administered intravenously every 5 days for five doses at either 52 or 63 mg/kg, equivalent to 31 and 38 mg/kg of doxorubicin to tumor-bearing nude mice. In two separate studies with groups of 8 or 10 mice each, no acute signs of toxicity were observed following repeat administration of Suc-Leu-Ala-Leu-Dox. In one study, one animal in each dose group (n=8) was terminated as a possible drug-related toxicity death late in the study, at Days 58 and 57 in the low and high dose-groups respectively. The safety of the compound was evidenced by little body weight loss in either the high or low dose groups (less than 5% of the initial weight) during the 60-day observation period, in surviving animals (FIG. 14). In the other study, both the high and low dose were well tolerated. Only one animal in the high dose group (n=10) had over 15% of body weight loss at the end of the study (Day 61).

Example 12

Suc-Leu-Ala-Leu-Dox is Effective in Tumor Xenograft Models

Two mouse xenograft studies demonstrated the efficacy of Suc-Leu-Ala-Leu-Dox on the growth of human colon carcinoma (LS174T), and the outcome in terms of long-term survival. Healthy young female nude mice were subcutaneously implanted with chunks of LS174T. When the tumors reached approximately 50–100 mg in weight, treatment every 5 days for 5 doses, of groups of 8 or 10 mice with either 0, 52 or 63 mg/kg Suc-Leu-Ala-Leu-Dox was initiated. Tumor size and body weights were measured twice weekly for up to 60 days.

Figure 15:
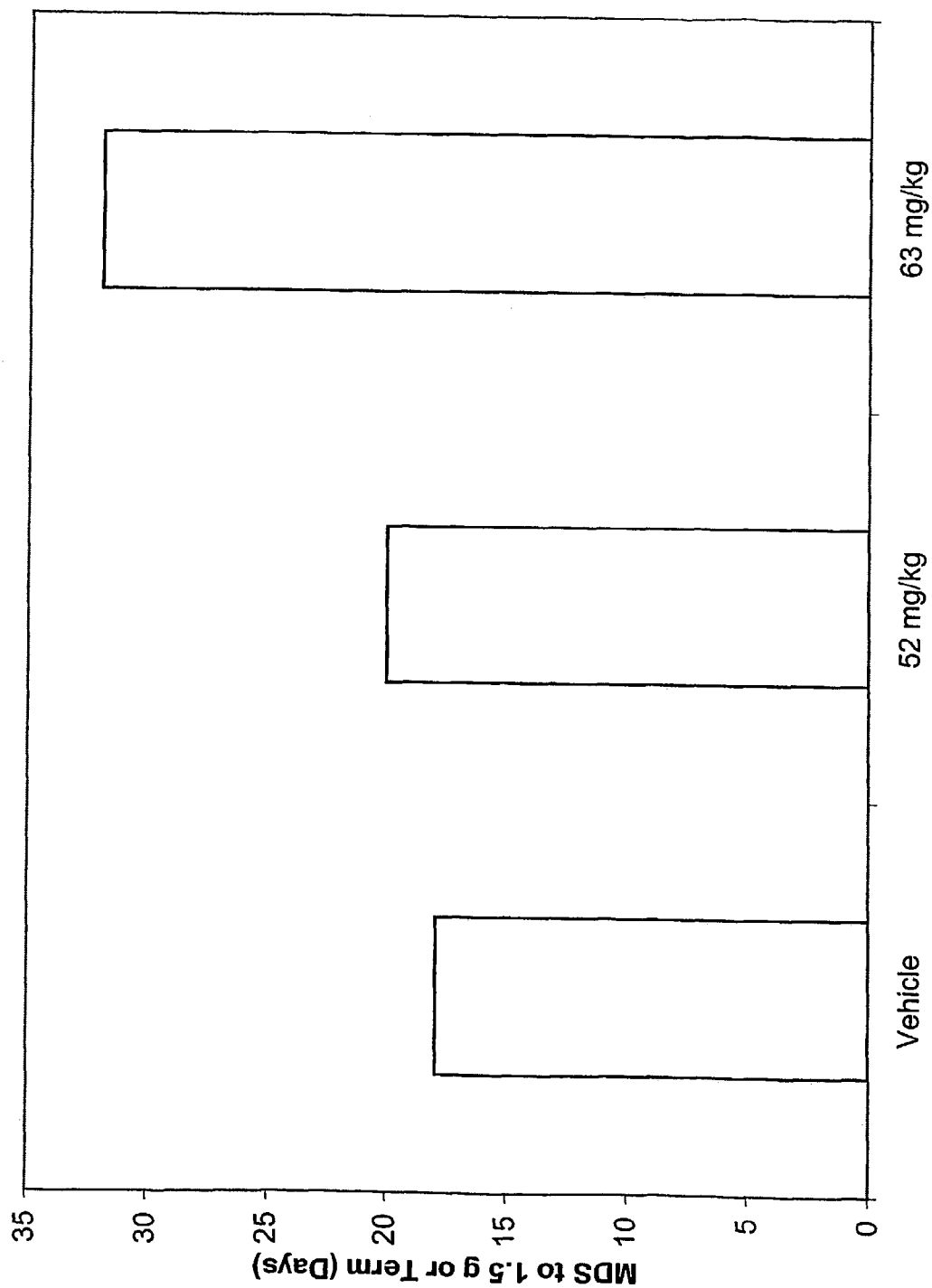
FIG. 15 is a graph illustrating the increase in Mean Days of Survival (MDS) in mice treated with Suc-Leu-Ala-Leu-Dox as compared with mice given the vehicle control.
Figure 16:
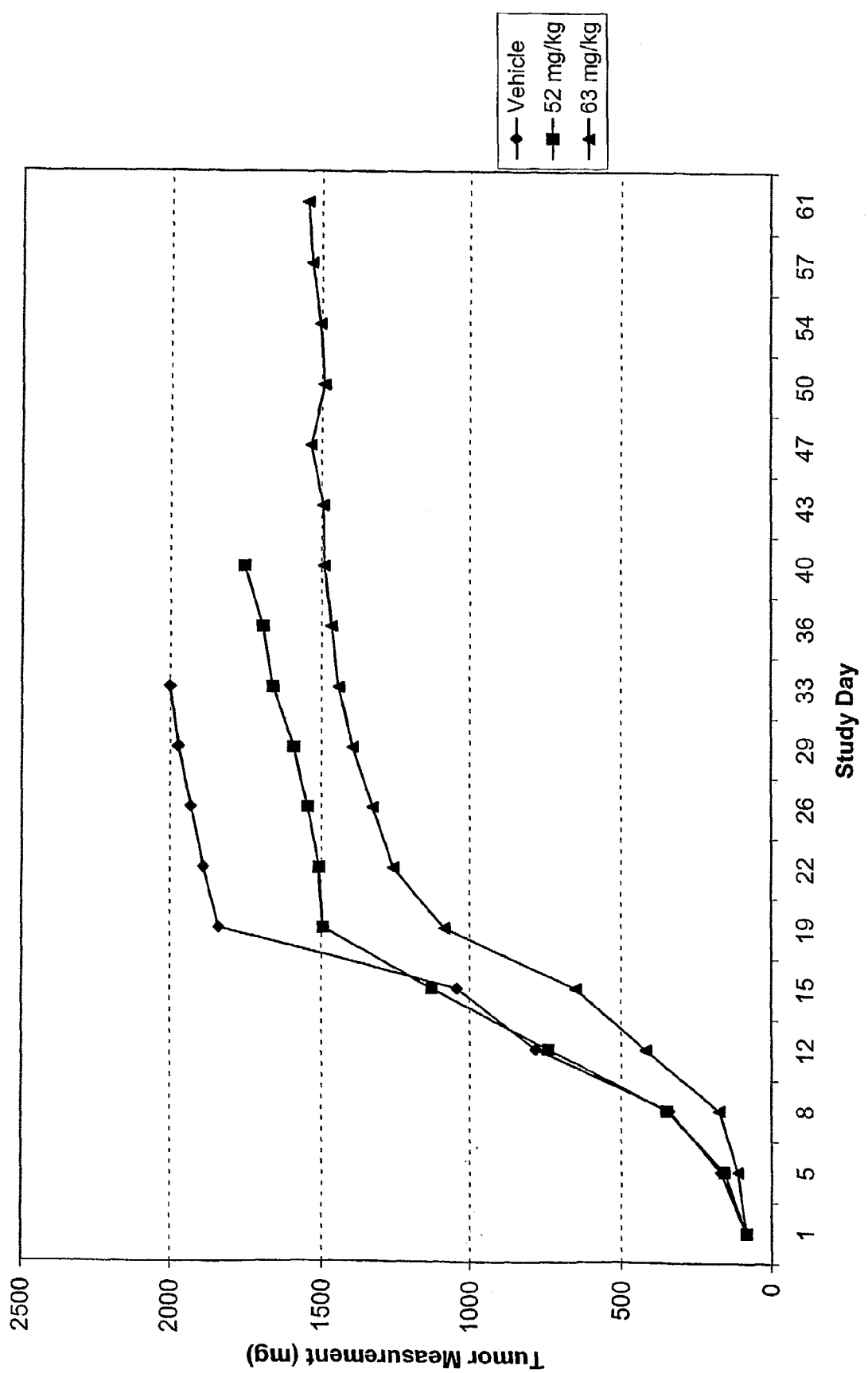
FIG. 16 is a graph of the rate of tumor growth in LS174T xenografted mice either treated with Suc-Leu-Ala-Leu-Dox or given the vehicle control.

A dose-dependent increase in survival of the mice was observed. The Mean Day of Survival was increased to 20 and 32 days in the treated groups, compared with 18 days in the vehicle control group (FIG. 15). Suc-Leu-Ala-Leu-Dox decreased the rate of tumor growth considerably over the vehicle control group (FIG. 16). In a greater number of cases than the untreated control, the tumors of the treated animals appeared to stop growing or regress. The compound was well tolerated, suggesting that the administered doses were both below the repeat-dose MTD.

In tumor efficacy studies, Suc-Leu-Ala-Leu-Dox exhibited dose-dependent efficacy, delaying tumor growth and increasing survival, and was very well tolerated. It was significantly more efficacious in this doxorubicin-insensitive xenograft model than doxorubicin alone. Despite rapid excretion of the parent compound, Suc-Leu-Ala-Leu-Dox, in tumor-bearing mice it has surprisingly strong anti-tumor activity, delivering high dose-levels of doxorubicin while sparing systemic toxicity. Thus it is an effective prodrug, which is able to extend survival and delay tumor growth in a doxorubicin-insensitive model, in which doxorubicin alone is virtually inactive.

However, post-analysis of the compounds showed that they contained about 47% active compound due to water content and impurity. So the doses mentioned in the above paragraph overestimated the amount of compound administered. Recalculation of the data showed that Suc-Leu-Ala-Leu-Dox decreased the rate of tumor growth over the vehicle control group. In tumor efficacy studies, Suc-Leu-Ala-Leu-Dox exhibited dose-dependent efficacy, delaying tumor growth and increasing survival, and was well tolerated. It was more efficacious in this doxorubicin-insensitive xenograft model than doxorubicin alone.

Example 13

Suc-Leu-Ala-Gly-Dox is Effective in Tumor Xenograft Models

A mouse xenograft study demonstrated the efficacy of Suc-Leu-Ala-Gly-Dox on the growth of human colon carcinoma (HT-29), and the outcome in terms of long-term survival. Healthy young male nude mice were subcutaneously injected with 5 million of HT-29 cells. When the tumors reached approximately 100 mg in weight, treatment every 7 days for 5 doses, of group of 8, 10, or 12 mice with vehicle, 4 mg/kg doxorubicin, 40 or 67 mg/kg Suc-Leu-Ala-Gly-Dox was initiated. Tumor size and body weights were measured twice weekly for up to 60 days.

A dose-dependent increase in survival of the mice was observed. Suc-Leu-Ala-Gly-Dox, given at 40 mg/kg and 67 mg/kg (42 mg/kg and 70 mg/kg doxorubicin equivalent concentration) was very well tolerated and greatly prolonged survival of tumor bearing mice. The doxorubicin treated mice had a MDS of 30 days. The Mean Day of Survival was increased to 39 and 41 days in the treated groups with Suc-Leu-Ala-Gly-Dox, compared with 26 days in the vehicle control group. (TABLE 10). The high does of Suc-Leu-Ala-Gly-Dox decreased the rate of tumor growth significantly over the vehicle control group (TABLE 10). The compound was very well tolerated, suggesting that the administered doses were both below the repeat-dose MTD.

TABLE 10

| Compound | Dose (mg/kg) | Mean Tumor Weight at Day 14 (mg) | % TGI (Day 14, mean) | Median Tumor Weight at Day 25 (mg) | % TGI (Day 25, median) | Calculated Mean Day of Survival (day) | Extension of Mean Day of Survival over controls | Number of Long Term Survivors | Toxicity (Weight Loss > 20%) |
|---|---|---|---|---|---|---|---|---|---|
| saline | — | 733 ± 72 (n = 12) | 0% | 1515 | 0% | 25.7 ± 2.6 (n = 11) | 0% | 0/11 | 0/11 |
| Doxorubicin | 4.0 | 665 ± 103 (n = 10) | 9.3% | 1046 | 30.9% | 30.0 ± 3.7 (n = 9) | 16.7% | 0/10 | 1/10 |
| Suc-Leu-Ala-Gly-Dox | 40 | 704 ± 92 (n = 8) | 4.0% | 952 | 37.2% | 38.8 ± 6.6 (n = 7) | 51.0% | 1/7 | 0/7 |
| Suc-Leu-Ala-Gly-Dox | 67 | 490 ± 124 (n = 7) | 33.2%* | 857 | 43.5% | 41.3 ± 7.2 (n = 7) | 60.7%* | 3/7 | 0/7 |

*Statistically different from the control at the p level of 0.10 (two-tailed)
: Some mice were excluded from tumor growth/survival analyses due to ulceration of tumors.
TGI: Tumor Growth Inhibition over control

Example 14

Advantages of Prodrugs over the Unconjugated Therapeutic Agent

The prodrugs of the invention provide treatment advantages over the therapeutic agent in its unconjugated form.

In the single dose Maximum Tolerated Dose (SD-MTD) studies, groups of normal mice were administered intravenous bolus doses of the prodrug. The mice were observed daily for 60 days and body weights measured twice weekly. The SD-MTD was estimated to be equal to the highest dose that produced no death in mice after 60 days. As shown in Table 11, the single-dose MTD of the prodrugs range from 10-fold to at least 16-fold higher than that of doxorubicin alone.

TABLE 11

| Compound | SD MTD* (mg/kg) | Optimal Efficacy Repeat Dose (mg/kg) | Optimal Efficacy Dose Frequency | Relative Rate of Cleavage |
|---|---|---|---|---|
| Suc-Met-Ala-Leu-Dox | 70 (42) | n.d. | n.d. | 49 |
| Suc-Leu-Tyr-Leu-Dox | >128 (70) | n.d. | n.d. | 14 |
| Suc-Leu-Ala-Leu-Dox | >117 (70) | 63 (38) | Q 5 days × 5 | 62 |
| Suc-βAla-Leu-Ala-Leu-Dox | 75 (42) | 71.2 (40) | Q 1 week × 5 | 100 |
| Doxorubicin | 4 (4) | 4 (4) | Q 1 week × 5 | n.a. | n.d. = not determined;
n.a. = not applicable

In repeat-dose studies in tumor bearing mice, groups of ten mice were dosed with various amounts of prodrug for a total of five doses at either five day or 1 week intervals. After frequent observation over 60 days, the dose which proved to be within acceptable toxicity limits and produced a decrease in tumor size was identified as the optimal efficacy repeat dose. As seen in Table 11, optimal efficacy repeat dose of the prodrugs are approximately 9-fold higher than that of doxorubicin alone. Thus, the prodrugs permit a much greater amount of therapeutic agent to be delivered to the body as a whole and thus to the vicinity of the target cell.

Surprisingly, the tripeptide prodrug, Suc-Leu-Ala-Leu-Dox, which is cleaved less completely than Suc-βAla-Leu-Ala-Leu-Dox in in vitro enzyme assays (see, e.g., Examples 1 and 2), is significantly better tolerated and more efficacious when administered in vivo at an equivalent dose. Under these conditions, Suc-Leu-Ala-Leu-Dox was well tolerated, and below its MTD threshold, when given repeatedly on a 5-day dosing schedule, compared with a 7-day dosing schedule for Suc-βAla-Leu-Ala-Leu-Dox, which was close to its MTD. The lower toxicity of Suc-Leu-Ala-Leu-Dox is consistent with the results of the metabolism studies. The predominant plasma metabolites of Suc-Ala-Leu-Dox are Ala-Leu-Dox and Leu-Dox. This is the same metabolite pattern as Suc-βAla-Leu-Ala-Leu-Dox, which is cleaved by trouase. The relative amounts of the metabolites detected in plasma, however, are less with the tripeptide.

A similar pattern of an upward shift in MTD value was observed with another tripeptide, Suc-Leu-Tyr-Leu-Dox, which was also well-tolerated at relatively high doses and was poorly cleaved by trouase.

The substantially higher MTD value of Suc-Leu-Ala-Leu-Dox is consistent with the in vitro evidence that tripeptides are not as good substrates for enzymatic cleavage as compared with the tetrapeptide, Suc-βAla-Leu-Ala-Leu-Dox. The resultant slower cleavage rates yield lower levels of systemic doxorubicin and hence less toxicity. The unexpectedly good efficacy results for Suc-Leu-Ala-Leu-Dox indicate that in the vicinity of a tumor, cleavage of tripeptides appears to be more effective than the background level of systemic cleavage. Based on the good therapeutic window observed with Suc-Leu-Ala-Leu-Dox, it appears that there is marked selectivity of the tripeptides for tumor tissue over the rest of the body. Considering this and the improved therapeutic window of the Suc-Leu-Ala-Leu-Dox compared with doxorubicin, is can be extrapolated that the Suc-Leu-Ala-Leu-Dox should be particularly useful for clinical treatment of tumors.

However, post-analysis of the compounds showed that they contained about 47% active compound due to water content and impurity. So the doses mentioned in the above paragraphs overestimated the amount of compound administered. The results from the experiment described above was re-analyzed. The re-analyzed data and new data for Suc-Leu-Ala-Gly-Dox is presented in TABLE 12.

TABLE 12

| Compound | SD MTD (mg/kg)* | Repeat Dose MTD (mg/kg)* | Repeat Dose Frequency | Relative Rate of Cleavage |
|---|---|---|---|---|
| Suc-Mer-Ala-Leu-Dox | 70 (42) | n.d. | n.d. | 49 |

TABLE 12-continued

| Compound | SD MTD (mg/kg)* | Repeat Dose MTD (mg/kg)* | Repeat Dose Frequency | Relative Rate of Cleavage |
|---|---|---|---|---|
| Suc-Leu-Tyr-Leu-Dox | >128 (70) (56) | n.d. | n.d. | 14 |
| Suc-βAla-Leu-Ala-Leu-Dox | 50 (28) | 57 (32) | Q 7 D × 5 | 100 |
| Suc-Leu-Ala-Leu-Dox | 59 (35) | 52 (31) | Q 5 D × 5 | 62 |
| Suc-Leu-Ala-Gly-Dox | >220 (141) | >110 (70) | Q 7 D × 5 | 40 |
| Doxorubicin | 16 (16) | 4 (4) | Q 7 D × 5 | n.a. | n.d. = not determined;
n.a. = not applicable
*values in parentheses are the doxorubicin equivalent dose Recalculation of the data showed that the single-dose MTD of the prodrugs range from 0.8-fold to at least 7.8-fold higher than that of doxorubicin alone. After frequent observation over 60 days, the dose which proved to be within acceptable toxicity limits was identified as the maximum tolerated repeat dose. As seen in TABLE 12, RD-MTD of the prodrugs are approximately 6.8-fold higher than that of doxorubicin alone. Repeat dosing of the prodrugs at or lower than their RD-MTD significantly prolong survival of LS174t or HT-29 tumor bearing mice, whereas that of doxorubicin is ineffective. As seen in TABLE 12, optimal efficacy repeat dose of the prodrugs are approximately 6-fold higher than that of doxorubicin alone.

A similar pattern of an upward shift in MTD value was observed with tripeptides, Suc-Leu-Ala-Gly-Dox and Suc-Leu-Tyr-Leu-Dox, which were also well tolerated at relatively high doses and was poorly cleaved by trouase.

The higher MTD value of Suc-Leu-Ala-Leu-Dox and Suc-Leu-Ala-Gly-Dox are consistent with the in vitro evidence that tripeptides are not as good substrates for enzymatic cleavage as compared with the tetrapeptide, Suc-βAla-Leu-Ala-Leu-Dox. The resultant slower cleavage rates yield lower levels of systemic doxorubicin and hence less toxicity. The unexpectedly good efficacy results for Suc-Leu-Ala-Leu-Dox and Suc-Leu-Ala-Gly-Dox indicate that in the vicinity of a tumor, cleavage of tripeptides appears to be more effective than the background level of systemic cleavage. Based on the good therapeutic window observed with Suc-Leu-Ala-Leu-Dox and Suc-Leu-Ala-Gly-Dox, it appears that there is marked selectivity of the tripeptides for tumor tissue over the rest of the body. Considering this and the improved therapeutic window of the Suc-Leu-Ala-Leu-Dox and Suc-Leu-Ala-Gly-Dox compared with doxorubicin, is can be extrapolated that the Suc-Leu-Ala-Leu-Dox and Suc-Leu-Ala-Gly-Dox should be particularly useful for clinical treatment of tumors.

Example 15

Hydrolysis by Purified CD10

Equal amounts of purified Porcine Kidney CD10 (Elastin Products Company) were incubated with 12.5 μg/mL of various peptidyl doxorubicin compounds for up to 10 hr at 37° C. in pH 7.4 50 mM TrisHCl, 150 mM NaCl, 0.1% Triton X-100. Reaction products were analyzed by HPLC with fluorescence detection. Rates were essentially linear over the incubation period. The observed product was Leu-doxorubicin. Table 13 provides the percent of each test compound that was hydrolyzed over the ten hour period. Further these results are expressed relative to a standard test compound, Suc-βAla-Leu-Ala-Leu-Dox.

TABLE 13

Hydrolysis by CD10

| Substrate | % hydrolysis/10 hr | Fraction hydrolyzed relative to standard |
|---|---|---|
| Suc-βAla-Leu-Ala-Leu-Dox (Standard) | 10.9 | 1.0 |
| Suc-Leu-Ala-Leu-Dox | 8.3 | 0.75 |
| Suc-Leu-Ala-Gly-Dox | 0 | 0 |

Example 16

Tumor-Activated Prodrug Activity on Ball-1, Ramos and Namalwa Cells

In addition to LNCaP, a number of B-cell lines, such as Ramos and Namalwa cells express CD10 (CD10$^{pos}$ cells). However, another B-cell line, BALL-1 cells, do not express CD10 and serve as a CD10 negative cell line (CD10$^{neg}$ cells).

Suspension cells, BALL-1, Ramos and Namalwa cells were cultured in RPMI media containing 10% heat inactivated fetal calf serum (FCS). On the day of the study, the cells were collected, washed and resuspended at a concentration of $0.5 \times 10^6$ cells/ml in RPMI containing 10% FCS. 100 μl of cell suspension was added to 96 well plates. Serial dilutions (3-fold increments) of doxorubicin or test compounds were made and 100 μl of compounds were added per well. Finally 10 μl of a 100 μCi/ml $^3$H-thymidine was added per well and the plates were incubated for 24 hours. The plates were harvested using a 96 well Harvester (Packard Instruments) and counted on a Packard Top Count counter. Four parameter logistic curves were fitted to the $^3$H-thymidine incorporation as a function of drug molarity using Prism software to determine IC$_{50}$ values.

The most selective analog was Suc-Leu-Ala-Leu-Dox (Table 14) with an ~30-35 fold difference between CD10$^{pos}$ and CD10$^{neg}$ cells.

TABLE 14

Activity on BALL (CD10$^{neg}$)-1, Ramos (CD10$^{pos}$) & Namalwa (CD10$^{pos}$) cells

| | IC50 (μM) | | | Ratio | |
|---|---|---|---|---|---|
| Compound | Ball-1 | Ramos | Namalwa | Ball-1: Ramos | Ball-1: Namalwa |
| DOX | 0.02 | 0.01 | 0.01 | 1 | 2 |
| Suc-Leu-Ala-Leu-Dox | 78.67 | 2.63 | 2.27 | 30 | 35 |
| Suc-Leu-Ala-Gly-Dox | 23.33 | 22.67 | 17.33 | 1 | 1 |

Thus, Suc-Leu-Ala-Leu-Dox is cleaved by CD10 but Suc-Leu-Ala-Gly-Dox is not.

Analytical Methods for the Remaining Examples

The peptide sequences, synthesized using either solid or solution phase approaches, were used without further purification if the analytical HPLC (methods A, B & D) showed the crude product to be greater than 80% pure. If not, the material was purified using preparative HPLC Method C.

HPLC Method A

Analytical HPLC analyses were performed on a Waters 2690 using a C-18 column (4 μm, 3.9×150 mm ID, flow rate 1 mL/min) eluting with a gradient of solvent A (0.1% TFA/H$_2$O) and solvent B (0.1% TFA/ACN) and the data was processed at λ254 nm using the Waters Millennium system. Analytical HPLC gradient started with 90% of solvent A and ended with 100% of solvent B over a period of 14 minutes (linear). Purity of the compounds for this method and the following ones was assessed as the relative percentage area under the curve of the peaks.

HPLC Method B

Analytical HPLC analyses were performed on a Waters 2690 using a C-8 column (3.5 μm, 4.6×150 mm ID, flow rate 1 mL/min) eluting with a gradient of solvent A (80% 20 mM ammonium formate and 20% acetonitrile) and solvent B (20% 20 mM ammonium formate and 80% acetonitrile) and the data was processed at λ254 nm using the Waters Millennium system. Analytical HPLC gradient started with 100% of solvent A to 100% of solvent B over a period of 30 minutes (linear).

HPLC Method C

Preparative purification of crude products was achieved using a Waters Delta Prep 4000 system using a C-4 column (15 μm, 40×100 mm ID, flow rate 30 mL/min) eluting with a gradient of solvent A (H$_2$O), and solvent B (MeOH). The preparatory HPLC gradient started with 80% of solvent A and goes to 100% of solvent B over a period of 70 minutes (linear). The data was processed at λ254 nm using the Waters Millennium System.

HPLC Method D

Analytical HPLC was accomplished on a Hewlett Packard instrument using a TSK superODS column (TosoHaas); solvent A (TFA 0.1% in water); solvent B (TFA 0.1% in acetonitrile); gradient: 30 to 36% of B in 2 minutes, 36 to 41% of B in 10 minutes, 41 to 90% of B in 3 minutes, 5 minutes at 90% B, detection wavelength λ254 nm.

NMR and MS

Additional structural determinations were done by NMR and MS techniques and the results supported the claimed compounds.

TLC Method

TLC analysis was carried out on silica gel 60F-254 nm-0.25 mm plates (Merck) with DCM/MeOH/H$_2$O/Formic acid 88% 85/15/1/2 for elution.

Ninhydrin Test

A few milligrams of product were introduced in a test tube, and two drops of Solution A (50 mg/mL ninhydrin in ethanol), two drops of Solution B (4 mg/mL phenol in ethanol), then two drops of Solution C (2 mL 0.01M KSCN, aqueous in 100 mL pyridine) were added. The mixture was left in a boiling water bath for five minutes. In the presence of a free amine the solution becomes purple.

Specific Oligopeptide Synthetic Examples

Sources of Commercially Available Reagents

Doxorubicin and Daunorubicin were supplied by Meiji (Japan), Pd(PPh$_3$)$_4$ by Strem chem (Newburyport, Mass.), PEG by Shearwater(Huntsville, Ala.), solvents, HATU by Aldrich (Milwaukee, Wis.); all resins and amino acids were supplied by ABI (Foster City, Calif.), Novabiochem (San Diego, Calif.), Advanced ChemTech (Louisville, Ky.), Peptide International (Louisville, Ky.), or SynPep (Dublin, Calif.).

Example 17

Synthesis of Fmoc-Leu-Ala-Leu-OH

Tripeptide (Fmoc-Leu-Ala-Leu-OH) was synthesized using solid-phase approach with standard Emoc chemistry. A typical synthesis used Wang's alkoxy resin (0.60 mmol/gm loading). Fmoc-protected amino acids were used for solid-phase peptide synthesis.

For a scale of 1 mM peptide on resin, 3 equivalents of amino acid was preactivated with HBTU as the activating agent for 5 minutes before being added to the resin together with 2 equivalents of DIEA. The coupling reaction was carried out for 2 h and then washed with DMF (25 mL×3) and DCM (25 mL×3). The coupling reaction was repeated using 2 equivalents of amino acid using similar conditions. The reaction progress was monitored using ninhydrin test and if the ninhydrin test indicated incomplete reaction after 2 h then the coupling step was repeated for a third time. Deprotection was accomplished using 20% piperidine in DMF for 15–20 minutes. The coupling step was repeated with the next amino acid until the desired peptide was assembled on resin. The final cleavage of peptide from the resin was accomplished by treating the resin with a solution of 95% TFA and 5% water. After stirring the reaction mixture for 2 h at rt, the resin was filtered under reduced pressure and washed twice with TFA. Filtrates were combined and the peptide was precipitated by adding 400 mL of cold ether. The peptide was filtered under reduced pressure and dried to yield Fmoc-Leu-Ala-Leu-OH (92% HPLC purity by method A). Crude peptide was characterized by LC/MS and used for the next step without any further purification.

Example 18

Synthesis of Fmoc-Met-Ala-Leu-OH

Tripeptide (Fmoc-Met-Ala-Leu-OH) was synthesized using solid-phase approach with standard Fmoc chemistry. A typical synthesis used Wang's alkoxy resin (0.60 mmol/gm loading). Fmoc-protected amino acids were used for solid-phase peptide synthesis. For a scale of 1 mM peptide on resin, 3 equivalents of amino acid were preactivated with HBTU as the activating agent for 5 minutes before being added to the resin together with 2 equivalents of DIEA. The coupling reaction was carried out for 2 h and then washed with DMF (25 mL×3) and DCM (25 mL×3). The coupling reaction was repeated using 2 equivalents of amino acid under similar conditions. The reaction progress was monitored using ninhydrin test and if the ninhydrin test indicated incomplete reaction after 2 h then the coupling step was repeated for a third time. Deprotection was accomplished using 20% piperidine in DMF for 15–20 minutes. The coupling step was repeated with the next amino acid until the desired peptide was assembled on resin. The final cleavage of peptide from the resin was accomplished by treating the resin with a solution of 95% TFA and 5% water. After stirring the reaction mixture for 2 h at rt, the resin-was filtered under reduced pressure and washed twice with TFA. Filtrates were combined and the peptide was precipitated by adding 400 mL of cold ether. The peptide was filtered under reduced pressure and dried to yield Fmoc-Met-Ala-Leu-OH (90% HPLC purity by method A). Crude peptide was characterized by LC/MS and used for the next step without any further purification.

Example 19

Synthesis of Fmoc-Leu-Ala-Leu-Dox

Doxorubicin.HCl (2.34 g, 4.03 mmol) and Fmoc-Leu-Ala-Leu-OH (2.4 g, 4.48 mmol) were dissolved at room temperature in anhydrous DMF (150 mL). To this rapidly stirred solution, DIEA (1.56 mL, 8.96 mmol) was added in one portion and the reaction mixture was stirred for 15 minutes at room temperature. The reaction mixture was cooled to 0° C. using an ice bath and 1.87 g (4.92 mmol) of HATU was added slowly over 10 minutes. The reaction mixture was stirred for another 60 minutes at room temperature. Ice cold water (200 mL) was added to the reaction mixture, which resulted in the formation of a red precipitate. The precipitate was collected over a coarse frit, washed with 3×50 mL water and 3×50 diethyl ether and dried under reduced pressure to yield Fmoc-Leu-Ala-Leu-Dox (89% yield, 94% HPLC purity by method A). This product was characterized by MS and used for the next step without any further purification.

Example 20

Synthesis of Fmoc-Met-Ala-Leu-Dox

Doxorubicin.HCl (2.26 g, 3.89 mmol) and Fmoc-Met-Ala-Leu-OH (2.4 g, 4.33 mmol) were dissolved at room temperature in anhydrous DMF (150 mL). To this rapidly stirred solution, DIEA (1.5 mL, 8.66 mmol) was added in one portion and the reaction mixture was stirred for 15 minutes at room temperature. The reaction mixture was cooled to 0° C. using an ice bath and 1 g (2.64 mmol) of HATU was added slowly over 10 minutes. The reaction mixture was stirred for another 60 minutes at room temperature. Ice cold water (200 mL) was added to the reaction mixture, which resulted in the formation of a red precipitate. The precipitate was collected over a coarse frit, washed with 3×50 mL water and 3×50 diethyl ether and dried under reduced pressure to yield Fmoc-Met-Ala-Leu-Dox (86% yield, 93% HPLC purity by method A). This product was characterized by MS and used for the next step without any further purification.

Example 21

Synthesis of Suc-Leu-Ala-Leu-Dox

To a solution of Fmoc-Leu-Ala-Leu-Dox (4.4 g, 4.13 mmol) in 20 mL of dry DMF, piperidine (20.4 mL, 206 mmol) was added in one portion resulting in a color change from red to purple. The reaction mixture was stirred for 5 minutes at room temperature and then cooled to −20° C. using dry ice/acetone bath. 21.2 g (210 mmol) of succinic anhydride was then added to the cooled reaction mixture in one portion. The reaction was stirred rapidly at −5° C. for 5 minutes then at room temperature for another 90 minutes. 750 mL of anhydrous diethyl ether was added to the reaction mixture, which resulted in the formation of a red precipitate. This precipitate was isolated on a medium glass frit, washed with 2×50 mL of diethyl ether and dried under reduced pressure to yield Suc-Leu-Ala-Leu-Dox (80% yield, 88% HPLC purity by method B). The final product was purified using prep HPLC method C and characterized by LC/MS which gave a molecular weight of 939 (expected molecular weight 940).

Example 22

Synthesis of Suc-Met-Ala-Leu-Dox

To a solution of Fmoc-Met-Ala-Leu-Dox (4 g, 3.7 mmol) in 50 mL of dry DMF, piperidine (18.72 mL, 185 mmol) was added in one portion resulting in a color change from red to purple. The reaction mixture was stirred for 5 minutes at room temperature and then cooled to −20° C. using dry ice/acetone bath. 19 g (189 mmol) of succinic anhydride was then added to the cooled reaction mixture in one portion. The reaction was stirred rapidly at −5° C. for 5 minutes then at room temperature for another 90 minutes. 750 mL of anhydrous diethyl ether was added to the reaction mixture, which resulted in the formation of a red precipitate. This precipitate was isolated on a medium glass frit, washed with 2×50 mL of diethyl ether and dried under reduced pressure to yield Suc-Met-Ala-Leu-Dox (78% yield, 89% HPLC purity by method B). The final product was purified using prep HPLC method C and characterized by LC/MS which gave a molecular weight of 939 (expected molecular weight 940).

Example 23

Synthesis of Fmoc-Met-Ala-Leu-OBn

The Fmoc-Met-Ala-Leu is added into a round bottom flask with DMF and a magnetic stirrer. After the tripeptide is dissolved, benzyl bromide, followed by cesium carbonate, is added to the solution with stirring. The reaction mixture is stirred at room temperature for 1.5 hrs. Then, the reaction mixture is slowly poured into a flask with iced water. The precipitate is collected by suction filtration. The product, Fmoc-Met-Ala-Leu-OBn, is washed with water and placed in a vacuum desiccator.

Example 24

Synthesis of Met-Ala-Leu-OBn

In a round bottom flask (25 mL), Fmoc-Met-Ala-Leu-OBn is dissolved in 5 mL of anhydrous DMF. Piperidine is added to the solution and the mixture is stirred at room temperature for 25 minutes. The reaction is quenched with water and extracted with ethyl acetate. The combined organic layer is further washed by water, brine and dried over sodium sulfate. Solid Met-Ala-Leu-OBn is obtained after removal of solvent.

Example 25

Synthesis of MeOSuc-Met-Ala-Leu-OBn

In a round bottom flask, methyl hemisuccinate is dissolved in anhydrous DMF. DIEA followed by HBTU are added into the solution. The mixture is stirred at room temperature for 45 minutes. To this mixture is added a solution of Met-Ala-Leu-OBn (crude) in anhydrous DMF. The mixture is continually stirred at room temperature for 2.5 hrs. Then, the reaction mixture is slowly poured into a flask with iced water while stirring. A large amount of white solid precipitates out which is extracted by ethyl acetate. The combined organic layer is further washed by water, brine and dried over sodium sulfate. Solid MeOSuc-Met-Ala-Leu-OBn is obtained after removal of solvent.

Example 26

Synthesis of MeOSuc-Met-Ala-Leu

MeOSuc-Met-Ala-Leu-OBn is added into an Erlenmeyer flask with 100 mL of methanol. 50 mL of methanol is added. The solution is transferred into a hydrogenation reaction vessel. To this vessel, Pd—C is added. After hydrogenation for 2 hours at room temperature, the reaction is stopped and the catalyst was filtered. Solid MeOSuc-Met-Ala-Leu is yielded after removal of solvents.

Example 27

Coupling of MeOSuc-Met-Ala-Leu and Doxorubicin Using the "Urea Method"

Under dry nitrogen atmosphere MeOSuc-Met-Ala-Leu and doxorubicin hydrochloride are suspended/dissolved in 800 mL dry, urea-saturated (~30% w/v) DMF and DIEA. This mixture is cooled to 0–3° C. over ~25 minutes. At this point HATU is added as a solution in ~100 mL urea saturated DMF over 10 minutes (the volume of this solution should be kept minimal). The reaction mixture is stirred for 10 minutes at −2 to 2° C. and poured into 4000 mL ice cold brine, containing 2% v/v acetic acid over approximately five minutes with vigorous stirring. The product is filtered off on a medium porosity fritted glass filter, washed generously with water and dried under reduced pressure.

Example 28

Synthesis of MeOSuc-Met-Ala-Leu-Dox Therapeutic Agent

In a round bottom flask, MeOSuc-Met-Ala-Leu and doxorubicin are dissolved in anhydrous DMF. After the mixture is stirred for 5 minutes, DIEA followed by HBTU is added into the solution. The mixture is stirred at room temperature for 4 hrs. DMF is removed by a rotary evaporator and the residue is taken up in 4.0 mL 1:1 methylenechloride:methanol. To this solution, 40 mL of ether is slowly added while stirring. The precipitate is collected by suction filtration. The solid MeOSuc-Met-Ala-Leu-Dox is washed with ether (2×10 mL) and dried in a vacuum desiccator.

Example 29

Removal of Free Doxorubicin from MeOSuc-Met-Ala-Leu-Dox

MeOSuc-Met-Ala-Leu-Dox, DIEA and anhydrous DMF are placed in a 50 ml flask equipped with a magnetic stir bar. When the MeOSuc-Met-Ala-Leu-Dox has completely dissolved, isocyanate resin (pre-swollen in 5 mL of dichloromethane for 5 minutes) is added and the resulting solution is stirred for 2 h at room temperature with periodic HPLC monitoring. When HPLC traces indicate that the Dox is completely removed, the reaction mixture is filtered through a frit to remove the resin. The resin is washed with 10 ml DMF and the DMF washes are combined with the filtered reaction mixture. The filtered reaction mixture washes are then concentrated on a rotary evaporator equipped with a high vacuum pump and a 30° C. water bath. The residue is suspended in 5 ml of DMF and the solution is then slowly added into a rapidly stirred anhydrous diethylether solution. The product is then filtered over a frit, washed with diethylether, and dried under reduced pressure to give MeOSuc-Met-Ala-Leu-Dox.

Example 30

Hydrolysis of MeOSuc-Met-Ala-Leu-Dox Via Use of Cross Linked Enzyme

MeOSuc-Met-Ala-Leu-Dox therapeutic agent and 100 mL DMF are placed in a 500 mL flask. The suspension is vigorously agitated with a magnetic stirrer. When the MeOSuc-Met-Ala-Leu-Dox therapeutic agent has completely dissolved, 400 mL deionized water is added and the resulting solution stirred at 35° C. A slurry of 1 g washed CLEC-PC (Altus Biologics) the immobilized enzyme is rinsed in three aliquots of deionized water then resuspended in 10 mL 20% aqueous DMF prior to use. The resulting suspension is stirred at 35° C. with periodic HPLC monitoring. When all of the MeOSuc-Met-Ala-Leu-Dox therapeutic agent has been consumed, the reaction mixture is filtered through a 0.45 µM nylon membrane filter to remove the CLEC-PC enzyme. The CLEC-PC cake is washed with 3×10 mL methanol and the methanol washes are combined with the filtered reaction mixture. The filtered reaction mixture plus methanol washes are then concentrated on a rotary evaporator equipped with a high vacuum pump and a 30° C. water bath. The concentrate is then suspended in 50 mL deionized water at room temperature and rapidly stirred via mechanical stirrer. To this suspension a solution of 77.8 mg sodium bicarbonate (0.926 mmol, 0.95 eq.) in 100 mL deionized water is added over 2 minutes. The suspension is stirred at room temperature 20 minutes. The reaction mixture is filtered through a 0.45 µM nylon membrane filter and the Suc-Met-Ala-Leu-Dox is lyophilized.

Example 31

Hydrolysis of MeOSuc-Met-Ala-Leu-Dox Via Use of Soluble Enzyme

MeOSuc-Met-Ala-Leu-Dox therapeutic agent is suspended in 800 mL HPLC-grade water and homogenized for 60 minutes with an Ultraturrax T8 homogenizer to yield a finely divided suspension. This suspension is stirred (500 rpm) at 35° C. and adjusted to pH=6.05 with aq. 76 mM NaHCO$_3$. 1.0 g *C. Antarctica* "B" lipase (Altus Biologics) is then added and the reaction mixture stirred at 35° C. for 48 hours. During the 48 hr reaction time, pH is maintained between 5.3 and 6.2 by periodic addition of 76 mM NaHCO$_3$ and the reaction is periodically monitored by HPLC. After the reaction is nearly complete, the reaction mixture is then adjusted to pH=7 with aq. 76 mM NaHCO$_3$ and filtered through a pad of Celite 521. The clarified reaction mixture is then acidified to ca. pH 3 with 5 mL glacial acetic acid. The precipitate is isolated by Celite 521 filtration, subsequently rinsing the Celite pad with methanol. The methanol solution is filtered through a 10–20 µM fritted glass filter and is dried by rotary evaporation. This product is converted to the sodium salt by dissolution in 70 mL 76 mM NaHCO$_3$ (0.95 eq.) and lyophilized. The product is identical to that of example 24.

Example 32

Immobilized *Candida Antarctica* "B" Lipase Hydrolysis of MeOSuc-Met-Ala-Leu-Dox 30.0 g *Candida Antarctica* "B" lipase (Altus Biologics) is dissolved in 300 mL water and dialyzed against 3×4l of 50 mM aq. NaHCO$_3$ (pH=6.4). 360 mL of Pharmacia NHS- Activated Sepharose 4 Fast Flow is placed in a coarse glass fritted funnel and rinsed with 5×450 mL ice-cold 1 mM aq. HCl. The rinsed NHS-Activated Sepharose is then combined with the dialyzed enzyme solution. The resulting suspension is stirred at ambient temperature (~22° C.) for 2.0 hours. The Sepharose/enzyme conjugate is then isolated on a coarse fritted glass filter and then stirred in 1000 mL 100 mM aq. TRIS (pH=7.45) for 15 minutes. This suspension is filtered and incubated with another 1000 mL of 100 mM aqueous TRIS buffer (pH=7.45) at 4° C., overnight. In the morning, the immobilized enzyme is filtered off and after washing with water, is placed into a 2000 mL three-necked, round-bottomed flask. 43 g MeOSuc-Met-Ala-Leu-Dox therapeutic agent is added and the solids are suspended in 800 mL deionized water. The flask is fitted with an overhead stirrer, and a pH-stat set to keep the pH of the reaction mixture between 5.9–6.2 by controlling a syringe pump. The syringe pump is charged 0.1 M $NaHCO_3$. Progress of the reaction is followed by HPLC. After the reaction is nearly complete, the immobilized enzyme is filtered off and the liquid phase is lyophilized. The dry solids are then suspended in ~11 mL dry THF and filtered off.

Example 33

Synthesis of N-Cap Allyl-Hemisuccinate

This molecule was prepared according the procedure of Casimir, J. R., et.al. *Tet. Lett.* 36(19):3409, (1995). 10.07 g (0.1 mol) succinic anhydride and 5.808 g (0.1 mol) allyl-alcohol were refluxed in 100 mL toluene for 6 hours. The reaction mixture was concentrated under reduced pressure. 15.5 g; 98%. The resulting material was pure enough to use in subsequent reactions. The purity and identity of the semi-solid product was confirmed by $^1$HNMR and $^{13}$CNMR, by LC/MS.

Example 34

Synthesis of Allyl-Succinyl-Met-Ala-Leu-Dox.

In a round bottom flask N-Cap-Allylhemisuccinyl form of Met-Ala-Leu and doxorubicin are dissolved in anhydrous DMF. After the mixture is stirred for 5 minutes, DIEA followed by HATU is added into the solution. The mixture is stirred at room temperature for 2 hours. DMF is removed by a rotary evaporator and the residue taken up in 4.0 ml 1:1 DCM: MeOH. To this solution, 100 ml of ether is slowly added while stirring. A red precipitate forms and is collected by suction filtration. The solid is washed with ether (2×2 ml) and dried in a vacuum desiccator to give the Allyl-Succinyl-Met-Ala-Leu-Dox therapeutic agent.

Example 35

Preparation of Suc-Met-Ala-Leu-Dox from allyl-succinyl-Met-Ala-Leu-Dox

To a stirred solution of allyl-succinyl-Met-Ala-Leu-Dox in 2 mL THF, under nitrogen atmosphere, tetrakis(triphenylphosphine) palladium is added as a solid. After 10 minutes the precipitate formed during the reaction is filtered off and washed with THF. The solids are Suc-Met-Ala-Leu-Dox.

Example 36

Synthesis of Sodium Salt of Gl-Met-Ala-Leu-Dox

Piperidine (436 µL, 4.413 mmol) was added to a solution of Fmoc form of Met-Ala-Leu-Dox (95 mg, 0.088 mmol) in DMF (4.5 mL). After stirring for 5 minutes at room temperature, the reaction mixture was cooled to −5° C. and glutaric anhydride (624 mg, 5.472 mmol) was quickly added. The cold bath was removed as soon as the color changed and the mixture was stirred at room temperature for another 10 min. The DMF was removed by rotary evaporation and the residue dissolved in chloroform (2.5 mL). Diethyl ether (14 mL) was added and the resulting precipitate filtered. The filter cake was washed with diethyl ether, air dried and then resuspended in water (14 mL). The sodium salt was formed by addition of 0.025 M NaOH (4 mL, 0.10 mmol) dropwise to the suspension until complete dissolution of the solid. This solution was then lyophilized to give the sodium salt of glutaryl N-cap forn of Oligopeptide 38-Dox therapeutic agent in 97% yield with an HPLC purity of 87% by method D.

Example 37

Large Scale Synthesis of Methyl Succinyl-N-Cap form of Leu-Ala-Leu-Dox Therapeutic Agent 120 mmol Doxorubicin.HCl and 199 mmol MeOSuc-Leu-Ala-Leu are dissolved in anhydrous DMF (10 L) under nitrogen. 76 mL DIEA (434 mmol) is added to the reaction mixture and the reaction mixture is stirred for 10 minutes at room temperature under nitrogen. The reaction mixture is then cooled to 0° C. over 10 minutes. In a separate flask a solution of 864 g HATU (220 mmol) in DMF (500 mL) is prepared. The HATU solution is added slowly over 20 minutes to the reaction mixture while the reaction mixture is maintained at 0° C. The reaction mixture is stirred at 0° C. for 30 minutes.

A solution of NaCl (7.5 Kg, at least 30% w/v) in water (25 L) is prepared and cooled to 0° C. The reaction mixture is then slowly added to the cooled brine solution with vigorous stirring over 120 minutes. The color of the solution must remain red, a blue solution indicates that the pH needs adjustment immediately to between 5.8–6.0 by adding acetic acid. The temperature is maintained at approximately 5° C. The red precipitate is filtered off on a medium porosity fritted glass filter, washed with water and dried under vacuum pressure over $P_2O_5$ to yield MeOSuc-Leu-Ala-Leu-Dox.

Example 38

Treatment of MeOSuc-Leu-Ala-Leu-Dox with Ps-isocyanate Beads to Remove Traces of Doxorubicin 146.4 g PS-isocyanate beads (240 mmol; supplied by Argonaut Lab, San Carlos, Calif.) are dissolved in 1.5 L of anhydrous DMF and allowed to swell for 5–10 minutes at room temperature. The swelled beads are filtered through a glass-fritted funnel and washed with additional 500 mL of anhydrous DMF. 112 mmol MeOSuc-Leu-Ala-Leu-Dox is dissolved in 1000 mL of anhydrous DMF and 12 mmol mL DIEA is added followed by the swelled PS-isocyanate beads. The reaction mixture is stirred at room temperature and is monitored using HPLC till the amount of doxorubicin peak is less than 0.1%. Analytical HPLC analyses are performed using Water 2690 Column: Waters Symmetry Shield C$_8$ 3.5 μM 4.6×140 mm (cat #WAT094269), solvent: A-80% aqueous 20 mM ammonium formate (pH=4.5) 20% acetonitrile, solvent: B-20% aqueous 20 mM ammonium formate (pH=4.5) 80% acetonitrile. Column temperature: controlled room temperature, sample Temperature 4° C., Run time: 37.5 minutes, detector: 254 nm, Flow rate: 1.0 mL/min, Injection amount 10 μg (0.5 mg/mL×0.02 mL), Mobile Phase A and B. Gradient: 37.5 minute linear gradient from 100% mobile phase A to 100% mobile phase B with a 7.5 minute equilibration delay.

When the doxorubicin peak is less than 0.1%, the reaction mixture is filtered through a coarse sintered glass funnel to remove the beads. A brine solution (at least 30% w/v) of 1.1 kg NaCl in 3.5 L water is prepared and cooled to 0° C. The filtered reaction mixture is then slowly added to the cooled brine solution with vigorous stirring over 45 minutes. The color of the solution must remain red, a blue solution indicates that the pH needs adjustment immediately to between 5.8–6.0 by adding acetic acid. The red precipitate is filtered through a medium sintered glass funnel, washed with water and dried under vacuum pressure over P$_2$O$_5$ to yield MeOSuc-Leu-Ala-Leu-Dox free of any residual doxorubicin.

MeOSuc-Leu-Ala-Leu-Dox is dissolved in 1 L MeOH and the methanol solution is then slowly added to 14 L of cooled ethyl ether with vigorous stirring over 60 minutes. The red precipitate is filtered through a medium sintered glass funnel, washed with ether (1 L) and dried under vacuum pressure to yield MeOSuc-Leu-Ala-Leu-Dox. The purity is determined by HPLC, as described in Example 44.

Example 39

Enzymatic Hydrolysis of MeOSuc-Leu-Ala-Leu-Dox to Yield Suc-Leu-Ala-Leu-Dox

The CLEC-CAB (*Candida Antartica* "B" Lipase) enzyme is purchased (from Altus Biologics., Boston, Mass.) in solution form, where the concentration of the enzyme is defined by the weight of dry enzyme per milliliter of solution. The crude enzyme suspension is shaken for few minutes to obtain a homogenous solution. 504 mL (328 mmol) of this homogenous solution is aliquoted into a flask. 2.5 L of deionized water is added and the slurry is stirred for 10 minutes using a magnetic stirrer. The enzyme solution is filtered using a coarse glass fritted funnel, without taking the enzyme to dryness. The enzyme is transferred back into a flask. The enzyme is suspended in water and filtered three more times.

The enzyme cake is resuspended into 550 mL of deionized water and transferred into a RB flask. To this suspension, MeOSuc-Leu-Ala-Leu-Dox (106 mmol) is added and the reaction mixture is stirred at room temperature (25° C). The pH of the reaction mixture is maintained between 5.8 and 6.1 by a pH-stat equipped with a syringe pump charged with 1 N NaHCO$_3$ solution. Progress of the reaction is followed with periodic HPLC monitoring, as described in Example 44. The reaction is continued until the reaction seems to be complete, as determined by HPLC.

To speed up the reaction, additional CLEC enzyme is required when the reaction is complete. Additional CLEC enzyme (homogenous solution) is washed in a column format as described above. The enzyme cake is resuspended into 1.1 L of deionized water and added to the reaction mixture. The reaction mixture is stirred at room temperature with periodic HPLC monitoring and the pH is maintained between 5.8 and 6.1.

Once the reaction is complete, the CLEC enzyme is removed from the reaction mixture by filtration through a 0.2 μM filter and rinsed with 500 mL of deionized water. The filtrate is then lyophilized to yield Suc-Leu-Ala-Leu-Dox.Na.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A compound comprising:
   (1) a therapeutic agent capable of entering a target cell,
   (2) an oligopeptide of the formula AA$^3$-AA$^2$-AA$^1$ wherein the oligopeptide is selected from the group consisting of: Leu-Ala-Gly (SEQ ID NO: 10), and Leu-Tyr-Leu (SEQ ID NO: 13);
   (3) a stabilizing group;
   (4) optionally, a linker group not cleavable by TOP,
   wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
   wherein the stabilizing group hinders cleavage of the oligopeptide by enzymes present in whole blood, and
   wherein the compound is cleavable by TOP.

2. The compound of claim 1 wherein the stabilizing group is a dicarboxylic or higher order carboxylic acid.

3. The compound of claim 1 wherein the stabilizing group is selected from the group consisting of: succinic acid, adipic acid, glutaric acid, phthalic acid, diglycolic acid, fumaric acid, naphthalene dicarboxylic acid, pyroglutamic acid, acetic acid, 1-naphthylcarboxylic acid, 2-naphthylcarboxylic acid, 1,8-naphthyl dicarboxylic acid, aconitic acid, carboxycinnamic acid, triazole dicarboxylic acid, gluconic acid, 4-carboxyphenyl boronic acid, polyethylene glycolic acid, butane disulfonic acid, nipecotic acid, isonipecotic acid, and maleic acid.

4. The compound of claim 1 wherein the stabilizing group is a non-genetically encoded amino acid having four or more carbons.

5. The compound of claim 1 wherein the stabilizing group is one of aspartic acid linked to the oligopeptide at the β-carboxy group of the aspartic acid or glutamic acid linked to the oligopeptide at the γ-carboxy group of the glutamic acid.

6. The compound of claim 1 wherein the stabilizing group is negatively charged or neutral.

7. The compound of claim 1 wherein the stabilizing group reduces interaction between the compound and endothelial cells that line blood vessels when administered to the patient.

8. The compound of claim 1 wherein TOP cleaves the linkage between AA$^3$ and AA$^2$ of the oligopeptide.

9. The compound of claim 1 wherein the compound is cleaved by TOP under an experimental condition at a test rate of cleavage of 10–80% of a standard rate of cleavage, the standard rate of cleavage tested on a test standard by TOP under the experimental condition, the test standard consisting of a conjugate of Suc-βAla-Leu-Ala-Leu and the therapeutic agent.

10. The compound of claim 9 wherein the test rate of cleavage is 30–65% of the standard rate of cleavage.

11. The compound of claim 1 wherein the therapeutic agent is selected from the group consisting of the group consisting of Alkylating Agents, Antiproliferative agents, Tubulin Binding agents, Vinca Alkaloids, Enediynes, Podophyllotoxins or Podophyllotoxin derivatives, the Pteridine family of drugs, Taxanes, Anthracyclines, Dolastatins, Topoiosomerase inhibitors, Maytanisoids and Platinum coordination complex chemotherapeutic agents, derivatives of the foregoing and analogs of the foregoing.

12. The compound of claim 1 wherein the therapeutic agent is selected from the group consisting of Doxorubicin, Daunorubicin, Vinblastine, Vincristine, Calicheamicin, Etoposide, Etoposide phosphate, CC-1065, Duocarmycin, KW-2189, Methotrexate, Methopterin, Aminopterin, Dichloromethotrexate, Docetaxel, Paclitaxel, Epithiolone, Combretastatin, Combretastatin A4 Phosphate, Dolastatin 10, Dolastatin 11, Dolastatin 15, Topotecan, Camptothecin, Mitomycin C, Porfiromycin, 5-Fluorouracil, 6-Mercaptopurine, Fludarabine, Tamoxifen, Cytosine arabinoside, Adenosine Arabinoside, Colchicine, Carboplatin, cis-Platin, Mitomycin C, Bleomycin, Melphalan, Chloroquine, Cyclosporin A, Maytansine, and derivatives of the foregoing, and analogs of the foregoing.

13. The compound of claim 1 wherein the target cell is a tumor or inflammatory cell.

14. The compound of claim 1 being a prodrug having an active portion, wherein the active portion of the prodrug is more capable of entering the target cell after cleavage by TOP than prior to cleavage by TOP, the active portion including at least the therapeutic agent.

15. The compound of claim 14 wherein the active portion of the prodrug consists of the therapeutic agent.

16. The compound of claim 14 wherein the active portion of the prodrug includes the therapeutic agent and at least the linker group.

17. The compound of claim 14 wherein the active portion of the prodrug includes the therapeutic agent and $AA^1$ of the oligopeptide.

18. The compound of claim 17 wherein the active portion of the prodrug further comprises $AA^2$ of the oligopeptide linked to $AA^1$.

19. The compound of claim 1 wherein the oligopeptide is directly linked to the therapeutic agent.

20. The compound of claim 1 wherein the oligopeptide sequence is indirectly linked to the therapeutic agent at the second attachment site of the oligopeptide via a linker group, the linker group selected from the group consisting of amino caproic acid, hydrazide group, an ester group, an ether group, and a sulphydryl group.

21. The compound of claim 1 wherein the compound is selected from the group consisting of, Suc-Leu-Ala-Gly-Dox, Suc-Leu-Tyr-Leu-Dox.

22. The compound of claim 1 wherein the compound is resistant to cleavage by CD10.

23. A compound comprising:
(1) a therapeutic agent capable of entering a target cell,
(2) an oligopeptide peptide selected from the group consisting of: Leu-Ala-Gly (SEQ ID NO: 10), and Leu-Tyr-Leu (SEQ ID NO: 13);
3) a stabilizing group, the stabilizing group selected from:
  (a) a dicarboxylic or higher order carboxylic acid,
  (b) a non-genetically encoded amino acid having four or more carbons, or
  (c) one of aspartic acid linked to the oligopeptide at the β-carboxy group of the aspartic acid or glutamic acid linked to the oligopeptide at the γ-carboxy group of the glutamic acid, and
(4) optionally, a linker group not cleavable by TOP,
  wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
  wherein the stabilizing group hinders cleavage of the oligopeptide by enzymes present in whole blood, and
  wherein the compound is cleavable by TOP.

24. The compound of claim 23 wherein the stabilizing group is selected from the group consisting of: succinic acid, adipic acid, glutaric acid, phthalic acid, diglycolic acid, fumaric acid, naphthalene dicarboxylic acid, pyroglutamic acid, acetic acid, 1-naphthylcarboxylic acid, 2-naphthylcarboxylic acid, 1,8-naphthyl dicarboxylic acid, aconitic acid, carboxycinnamic acid, triazole dicarboxylic acid, gluconic acid, 4-carboxyphenyl boronic acid, polyethylene glycolic acid, butane disulfonic acid, nipecotic acid, isonipecotic acid, and maleic acid.

25. The compound of claim 23 wherein the compound is resistant to cleavage by CD10.

26. A pharmaceutical composition comprising:
(1) a compound comprising:
  (a) a therapeutic agent capable of entering a target cell,
  (b) an oligopeptide peptide selected from the group consisting of: Leu-Ala-Gly (SEQ ID NO: 10), and Leu-Tyr-Leu (SEQ ID NO: 13);
  (c) a stabilizing group, the stabilizing group selected from:
  (d) optionally, a linker group not cleavable by TOP,
  wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide, wherein the stabilizing group hinders cleavage of the oligopeptide by enzymes present in whole blood, and wherein the compound is cleavable by TOP, and
(2) a pharmaceutically acceptable carrier.

* * * * *